US008575172B2

(12) United States Patent
Wilding et al.

(10) Patent No.: US 8,575,172 B2
(45) Date of Patent: Nov. 5, 2013

(54) PHARMACEUTICAL COMPOSITIONS OF ARIPIPRAZOLE

(75) Inventors: Ian Wilding, Nottingham (GB); Russell Pendleton, London (GB)

(73) Assignee: Zysis Limited, Beeston, Nottingham (GB)

( * ) Notice: Subject to any disclaimer, the term of this patent is extended or adjusted under 35 U.S.C. 154(b) by 366 days.

(21) Appl. No.: 12/443,036

(22) PCT Filed: Sep. 26, 2007

(86) PCT No.: PCT/GB2007/003677
§ 371 (c)(1),
(2), (4) Date: Mar. 26, 2009

(87) PCT Pub. No.: WO2008/038003
PCT Pub. Date: Apr. 3, 2008

(65) Prior Publication Data
US 2010/0004262 A1  Jan. 7, 2010

(30) Foreign Application Priority Data
Sep. 26, 2006 (GB) .................................. 0618879.1

(51) Int. Cl.
*A61K 31/497* (2006.01)
*A61P 25/00* (2006.01)

(52) U.S. Cl.
USPC .................................................. 514/253.07

(58) Field of Classification Search
None
See application file for complete search history.

(56) References Cited

U.S. PATENT DOCUMENTS

| | | | |
|---|---|---|---|
| 5,178,878 A | 1/1993 | Wehling et al. | |
| 6,221,392 B1 | 4/2001 | Khankari et al. | |
| 2005/0032836 A1 | 2/2005 | Greco et al. | |
| 2005/0158383 A1* | 7/2005 | Boehm et al. ................. | 424/468 |
| 2005/0202088 A1 | 9/2005 | Hanshermann et al. | |
| 2005/0245539 A1 | 11/2005 | Mendla et al. | |
| 2006/0073516 A1* | 4/2006 | Ito et al. ......................... | 435/7.1 |
| 2007/0042045 A1 | 2/2007 | Lizio et al. | |

FOREIGN PATENT DOCUMENTS

| | | |
|---|---|---|
| EP | 2066325 B1 | 6/2009 |
| WO | 9745124 A1 | 12/1997 |
| WO | 02053140 A2 | 7/2002 |
| WO | 02085366 A1 | 10/2002 |
| WO | 02102297 A2 | 12/2002 |
| WO | 03017983 A1 | 3/2003 |
| WO | 03026659 A1 | 4/2003 |
| WO | 03055464 A1 | 7/2003 |
| WO | 03066039 A1 | 8/2003 |
| WO | 03101428 A1 | 12/2003 |
| WO | 2004010932 A2 | 2/2004 |
| WO | 2004011031 A1 | 2/2004 |
| WO | 2004017897 A2 | 3/2004 |
| WO | 2004039320 A2 | 5/2004 |
| WO | 2004083183 A1 | 9/2004 |
| WO | 2005016261 A2 | 2/2005 |
| WO | 2005016262 A2 | 2/2005 |
| WO | 2005041935 A1 | 5/2005 |
| WO | 2005046561 A2 | 5/2005 |
| WO | WO 2005/041937 * | 5/2005 |
| WO | 2005048979 A2 | 6/2005 |
| WO | 2005053796 A1 | 6/2005 |
| WO | 2005058835 A2 | 6/2005 |
| WO | 2005082370 A1 | 9/2005 |
| WO | 2005102342 A1 | 11/2005 |
| WO | 2005107808 A2 | 11/2005 |
| WO | 2005113009 A1 | 12/2005 |
| WO | 2006000222 A2 | 1/2006 |
| WO | 2006012237 A2 | 2/2006 |
| WO | 2006016192 A2 | 2/2006 |
| WO | 2006053780 A1 | 5/2006 |
| WO | 2006069030 A1 | 6/2006 |
| WO | 2006096439 A2 | 9/2006 |
| WO | 2006097344 A1 | 9/2006 |
| WO | 2007004061 A1 | 1/2007 |
| WO | 2007007132 A1 | 1/2007 |
| WO | 2007035348 A2 | 3/2007 |
| WO | 2007081366 A1 | 7/2007 |
| WO | 2007081367 A1 | 7/2007 |

OTHER PUBLICATIONS

Jordan et al. The antipsychotic aripiprazole is a potent, partial agonist at the human 5-HT1A receptor. European Journal of Pharmacology, 441, 2002, 137-140.*
Miller. Atypical Antipsychotics: Sleep, Sedation and Efficacy. Prim. Care. Companion, J. Clin. Psychiatry, 2004; 6 (Suppl. 2).*
Elizabeth Winans. Aripiprazole. Am. J. Health Syst Pharm. 60: 2437-45, 2003.*
PCT/GB2007/003677, Written Opinion of the International Searching Authority, dated Apr. 23, 2008, 8 pages.
Abilify® Otsuka Pharmaceutical Co., Ltd., Tokyo, 101-8535, Jun. 2006, 6 pgs.
Masanori Kubo et al., Influence of Itraconazole Co-administration and CYP2D6 Genotype on the Pharmacokinetics of the New Antipsychotic Aripiprazole, Drug Metab. Pharmacokinet., 20 (1): 2005, pp. 55-64.
Tracy Swainston Harrison et al., Aripiprazole a Review of its Use in Schizophrenia and Schizoaffective Disorder, Adis Drug Evaluation, Drugs 2004: vol. 64 (15), pp. 1715-1736.
Suresh Mallikaarjun et al., "Pharmacokinetics, Tolerability, and Safety of Aripiprazole following Multiple Oral Dosing in Normal Healthy Volunteers," 2004 American College of Clinical Pharmacology, pp. 179-187.

(Continued)

*Primary Examiner* — Anna Pagonakis
(74) *Attorney, Agent, or Firm* — Panitch Schwarze Belisario & Nadel LLP

(57) ABSTRACT

An orally deliverable pharmaceutical composition provides controlled release of aripiprazole. The composition includes a therapeutically effective amount of aripiprazole and at least one pharmaceutically acceptable excipient. The compositions of the invention may exhibit one or more of the release profiles defined in the specification.

13 Claims, 18 Drawing Sheets

(56) References Cited

OTHER PUBLICATIONS

Espen Molden et al., "Pharmacokinetic Variability of Aripiprazole and the Active Metabolite Dehydroaripiprazole in Psychiatric Patients," Ther Drug Monit, vol. 28, No. 6, Dec. 2006, pp. 744-749.
Dieter Naber et al., "Aripiprazole: a new atypical antipsychotic with a different pharmacological mechanism," Progress in Neuro-Psychopharmacology & Biological Psychiatry 28, 2004, pp. 1213-1219.
J.W. Kasckow et al., "The Use of Novel Antipsychotics in the Older Patient With Neurodegenerative Disorders in the Long-Term Care Setting," Journal of American Medical Directors Association, Jul./Aug. 2004, vol. 5, pp. 242-248.
Clinical Pharmacology and Biopharmaceutics Review(s), NDA 21-436, Aripiprazole (BMS-337039, OPC-14597), pp. 1-30.
T. Kikuchi, "Antischizophrenic drug Abilify (aripiprazole). Dopamine system stabilizer," Farumashia (2007) vol. 43 (2), pp. 139-141 (abstract only).
C. Mitsonis et al., "Aripiprazole augmentation in the management of residual symptoms," Progress in Neuro-psychopharmacology & Biological Psychiatry, 2007, vol. 31, pp. 373-377 (abstract only).
A. Riga et al. "New concept in drug delivery detection by thermal mechanical analysis," Proceedings of the NATAS Annual Conference on Thermal Analysis and Applications, 2006, 34th pp. 153.10.948/1-153.10.948/6 (abstract only).
T. Owashi et al., "Aripiprazole," Nippon Byoin Yakuzaishikai Zasshi 2006, vol. 42(12), pp. 1639-1641 (abstract only).
R. Bridler, "[Aripiprazole in the treatment of schizophrenia]," Schweizerische Rundschau fur Medizin Praxis = Revue Suisse de Medecine Praxis, 2005, vol. 94(23), pp. 975-977 (abstract only).
W. Kinghorn et al., "Aripiprazole: pharmacology, efficacy, safety and tolerability," Expert Review of Neurotherapeutics, 2005, vol. 5(3): pp. 297-307 (abstract only).
M. Launer, "Partial dopamine agonists in schizophrenia," Hospital Medicine, 2005, vol. 66(5), pp. 300-303 (abstract only).
K. Chengappa et al., "Dosage and administration issues of antipsychotic agents (and adjunctive medicines) in the acute stabilization of psychoses," CNS Spectrums 2004, vol. 9(9), pp. 6-10 (abstract only).
M. Davies et al., "Aripiprazole: a novel atypical antipsychotic drug with a uniquely robust pharmacology," CNS Drug Reviews, 2004, vol. 10(4), pp. 317-336 (abstract only).
B. Green, "Focus on aripiprazole," Current Medical Research and Opinion, 2004, 20(2), pp. 207-213 (abstract only).
Anonymous, "Aripiprazole (Abilify) for schizophrenia," The Medical Letter on Drugs and Therapeutics, 2003, vol. 45 (1150), pp. 15-16 (abstract only).
E. Winans, "Aripiprazole," American Journal of Health-System Pharmacy, 2003, vol. 60(23), pp. 2437-2445 (abstract only).
J. Kelleher et al., "Advances in atypical antipsychotics for the treatment of schizophrenia: new formulations and new agents," CNX Drugs, 2002, vol. 16(4), pp. 249-261 (abstract only).
Anonymous, "Aripiprazole. Abilitat, OPC 14597," Drugs in R&D, 2002, vol. 3(1): pp. 25-27 (abstract only).
K. Scott et al., "Bioequivalence of an orally disintegrating tablet compared to the oral tablet formulation of the antipsychotic aripiprazole," European Neuropsychopharmacology, 2004, vol. 14, (Suppl. 3), p. S273.
S. Dutta et al., "Newer dopamine-serotonin system stabilising atypical antipsychotic agent," Indian J. Pharmacol, 2004, vol. 36(4), p. 267.
European Public Assessment Report (EPAR) for Abilify, European Medicines Agency, 2008, pp. 1-3.
T. Hirose et al., "The antipsychotic drug aripirazole (Abilify)," Nippon Yakurigaku Zashi, 2006, vol. 128(5), pp. 331-345 (abstract only).
Opposition Statement pursuant to Art. 99 EPC dated Jun. 1, 2012, against EP Patent No. 2 066 325 (EP Application No. 07823939.9), 14 pages.
Dow Chemical Company, (2005) "Using Methocel Cellulose Ethers for Controlled Release of Drugs in Hydrophilic Matrix Systems," 36 pages (Opposition Statement Exhibit D3).
Laihanen, et al., (1996) "Solubility and Intrinsic Dissolution Rate of Alprazolam Crystal Modifications", Pharmaceutical Development and Technology, 1(4), 373-380 (Opposition Statement Exhibit D5).
Opposition Statement filed Oct. 10, 2012 against EP Patent No. 2 066 325 B1 (based on EP Application No. 07823939.9).
Remington, The Science and Practice of Pharmacy, 21st Ed. (2006), 6 pages (Opposition Statement Exhibit D4).
English translation of an Office Action issued Nov. 27, 2012 in JP Application No. 2009-529761.
Fountoulakis et al, "Aripiprazole monotherapy in the treatment of bipolar disorder: A meta-analysis", Journal of Affective Disorders, vol. 133, pp. 361-370 (2011).
Stip et al, "Aripiprazole in Schizophrenia and Schizoaffective Disorder: A Review", Clinical Therapeutics, vol. 32, Supp. A, pp. S3-S20 (2010).
Keefe et al, "The Effects of Atypical Antipsychotic Drugs on Neurocognitive Impairment in Schizophrenia: A Review and Meta-ana.lysis", Schizophrenia Bulletin, vol. 25, No. 2, pp. 201-222 (1999).
Haffejee et al, "Treatment of alternating hemiplegia of childhood with aripiprazole", Developmental Medicine & Child Neurology, vol. 51, pp. 74-77 (2009).
Umene-Nakano et al, "Aripiprazole improves various cognitive and behavioral impairments after traumatic brain injury: a case report", General Hospital Psychiatry, vol. xx, pp. xx (published online Jun. 15, 2012).
López-Meza et al, "Aripiprazole in Psychosis Associated With Parkinson's Disease", Journal of Neuropsychiatry and Clinical Neurosciences, vol. 17, No. 3, pp. 421-422 (2005).
Ciammola et al, "Aripiprazole in the treatment of Huntington's disease: a case series", Neuropsychiatric Disease and Treatment, vol. 5, pp. 1-4 (2009).
Mintzer et al, "Aripiprazole for the Treatment of Psychoses in Institutionalized Patients With Alzheimer Dementia: A Multicenter, Randomized, Double-Blind, Placebo-Controlled Assessment of Three Fixed Doses", American Journal of Geriatric Psychiatry, vol. 15, No. 11, pp. 918-931 (Nov. 2007).
Brauser, "Atypical Antipsychotic Shows Promise for Cocaine Dependence", Medscape, downloaded from the internet at http://www.medscape.com/viewarticle/755247_print (Dec. 12, 2011).
Trunko et al, "Aripiprazole in Anorexia Nervosa and Low-Weight Bulimia Nervosa: Case Reports", International Journal of Eating Disorders, vol. 44, No. 3, pp. 269-275 (2011).
Greenaway et al, "Focus on Aripiprazole: A Review of its use in Child and Adolescent Psychiatry", Journal of the Canadian Academy of Child and Adolescent Psychiatry, vol. 18, No. 3, pp. 250-260 (Aug. 2009).
Nelson et al, "Augmentation treatment in major depressive disorder: focus on aripiprazole", Neuropsychiatric Disease and Treatment, vol. 4, No. 5, pp. 937-948 (2008).
Nickel et al, "Aripiprazole in the Treatment of Patients With Borderline Personality Disorder: A Double-Blind, Placebo-Controlled Study", American Journal of Psychiatry, vol. 163, No. 5, pp. 833-838 (May 2006).
AstraZeneca, Seroquel XR, quetiapine fumarate, Product Information (Feb. 11, 2013).
Pfizer, Xanax XR CIV (alpraxolam) extended-release tablets, Product Information (Aug. 2011).
Srinivasa Rao et al, "Analytical Method Development Report for Aripiprazole Tablets 2mg, 5mg, 10mg, 15mg, 20mg and 30mg," International Journal of Advances in Pharmacy, Biology and Chemistry, vol. 1, No. 3, pp. 377-380 (Jul.-Sep. 2012).
Norman et al, "New Formulations of Existing Antidepressants, Advantages in the Management of Depression," CNS Drugs, vol. 18, No. 8, pp. 505-520 (2004).
Van Harten, "Clinical Pharmacokinetics of Selective Serotonin Reuptake Inhibitors," Clinical Pharmacokinetics, vol. 24, No. 3, pp. 203-220 (1993).
Montgomery et al, "Plasma-Level Response Relationships with Fluoxetine and Zimelidine," Clinical Neuropharmacology, vol. 13, Suppl. 1, pp. S71-S75 (1990).
Liston et al, "Differential Time Course of Cytochrome P450 2D6 Enzyme Inhibition by Fluoxetine, Sertraline, and Paroxetine in

(56) References Cited

OTHER PUBLICATIONS

Healthy Volunteers," Journal of Clinical Psychopharmacology, vol. 22, No. 2, pp. 169-173 (Apr. 2002).

Colombo et al, "Swellable matrices for controlled drug delivery: gel-layer behaviour, mechanisms and optimal performance," Pharm. Sci. Technol. Today, vol. 3, No. 6, pp. 198-204 (Jun. 2000).

Abilify® U.S. Prescribing Information (Feb. 2012).

National Alliance on Mental Illness—Depression printout from http://www.nami.org/PrinterTemplate.cfm? Section=depression (Jul. 18, 2013).

Supplemental Opposition Statement dated Aug. 20, 2012 in the Opposition Proceeding to EP Patent No. 2 066 325.

Keith, "Advances in psychotropic formulations", Progress in Neuro-Psychopharmacology & Biological Psychiatry, vol. 30, pp. 996-1008 (May 6, 2006).

Seifert et al, "Aripiprazole (Ability™) Overdose in a Child", Clinical Toxicology, vol. 43, pp. 193-195 (2005).

Corrigan, "The Biopharmaceutic Drug Classification and Drugs Administered in Extended Release (ER) Formulations", Advances in experimental medicine and biology, vol. 423, pp. 111-128 (1997).

\* cited by examiner

Figure 1: Aripiprazole release percentages over 23 hours from the direct compression tablet of Example 1 in pH 4.0 phosphate buffer.
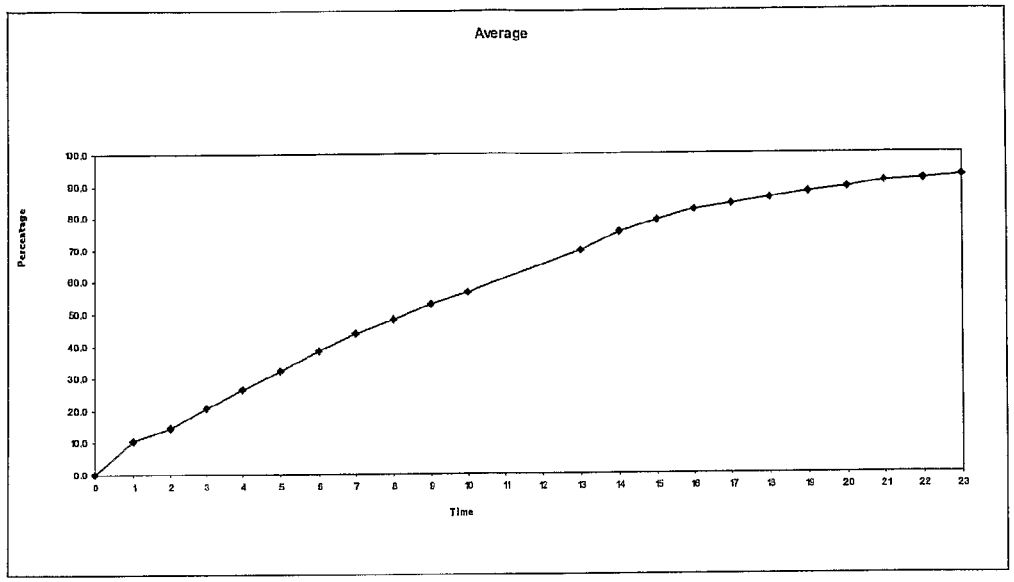
Figure 2: Aripiprazole release percentages over 20 hours from the direct compression tablet of Example 1 in 0.1M HCl.
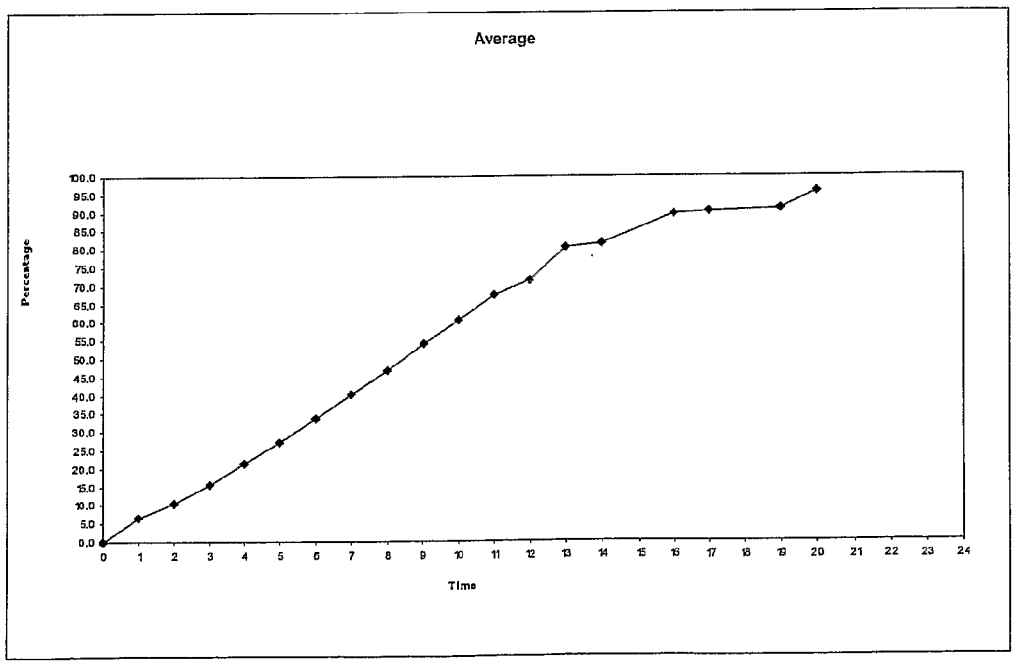

Figure 3    Aripiprazole release percentages over 23 hours from the wet granulation tablet of Example 1 in 0.1M HCl.
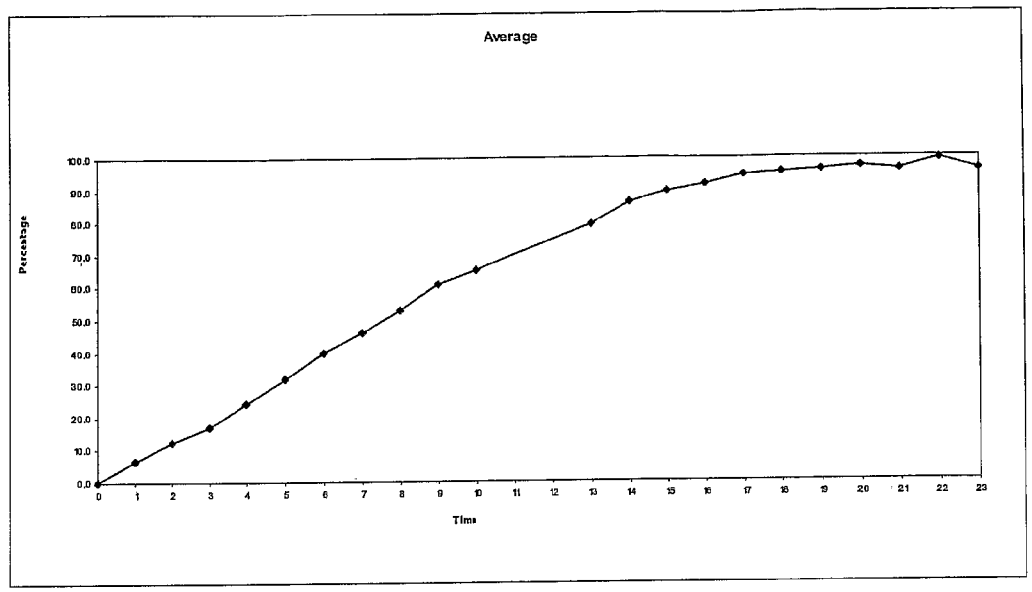
Figure 4:    Aripiprazole release percentages over 15 hours from the wet granulation tablet of Example 1 in pH 4.0 phosphate buffer.
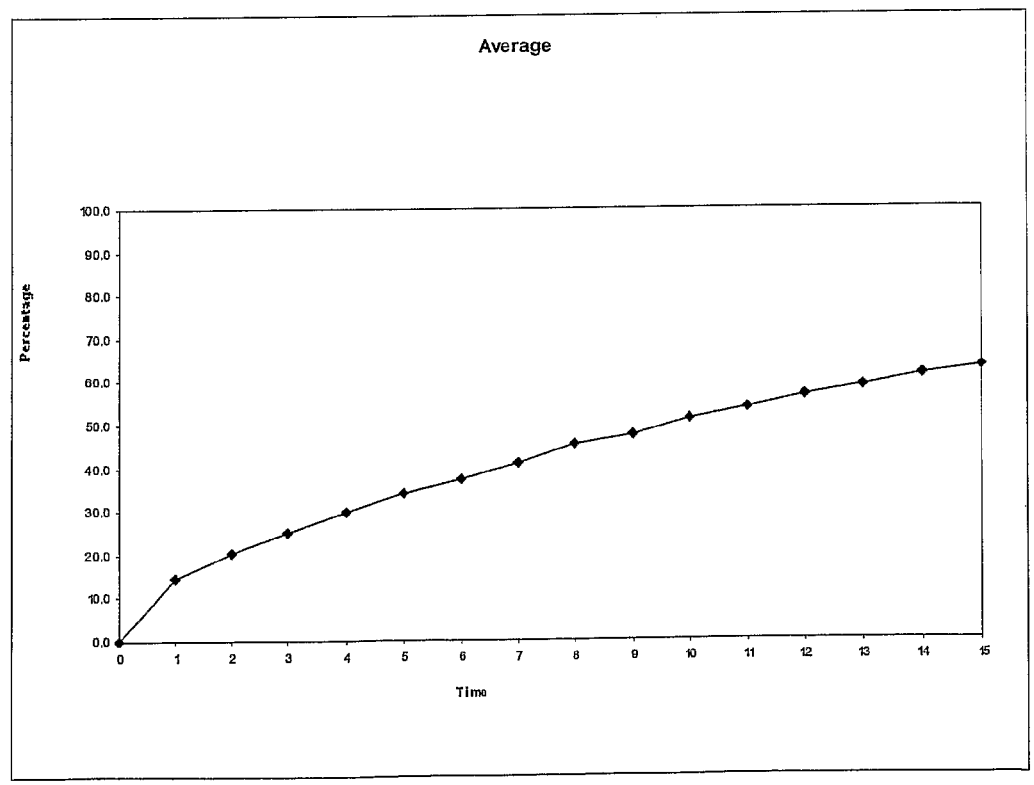

Figure 5: Simulated plasma concentrations of aripiprazole following repeated once daily oral doses of 5, 10, 15 and 20 mg aripiprazole (IR)
Day 14 profile (as published - Mallikaarjun *et al*) above and full 14-day profile below.
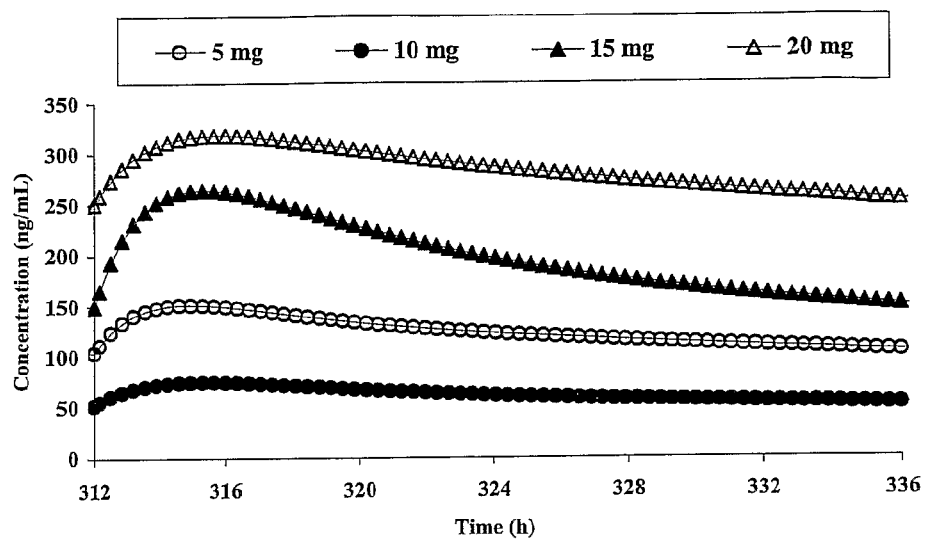
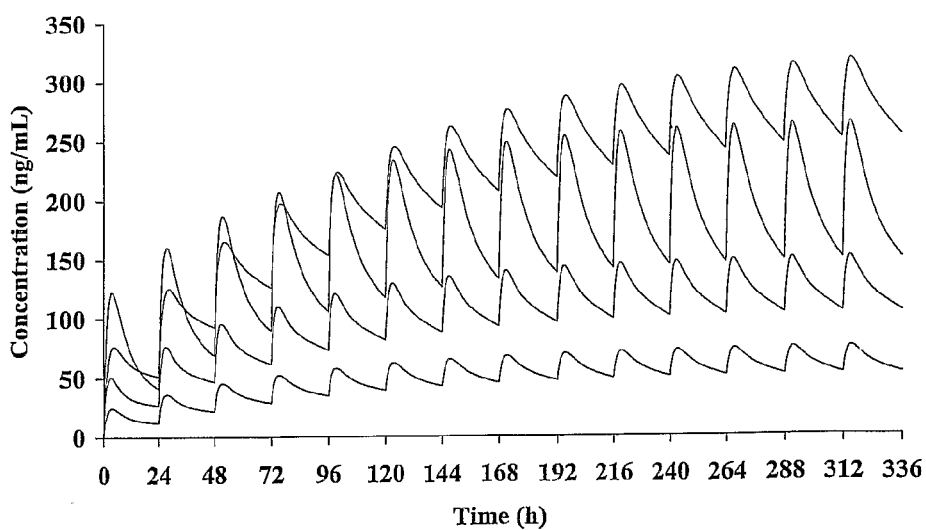

Figure 6: Simulated plasma concentrations of aripiprazole following repeated oral doses of 30 mg aripiprazole (IR) administered every other day and 15 mg (IR) administered once daily
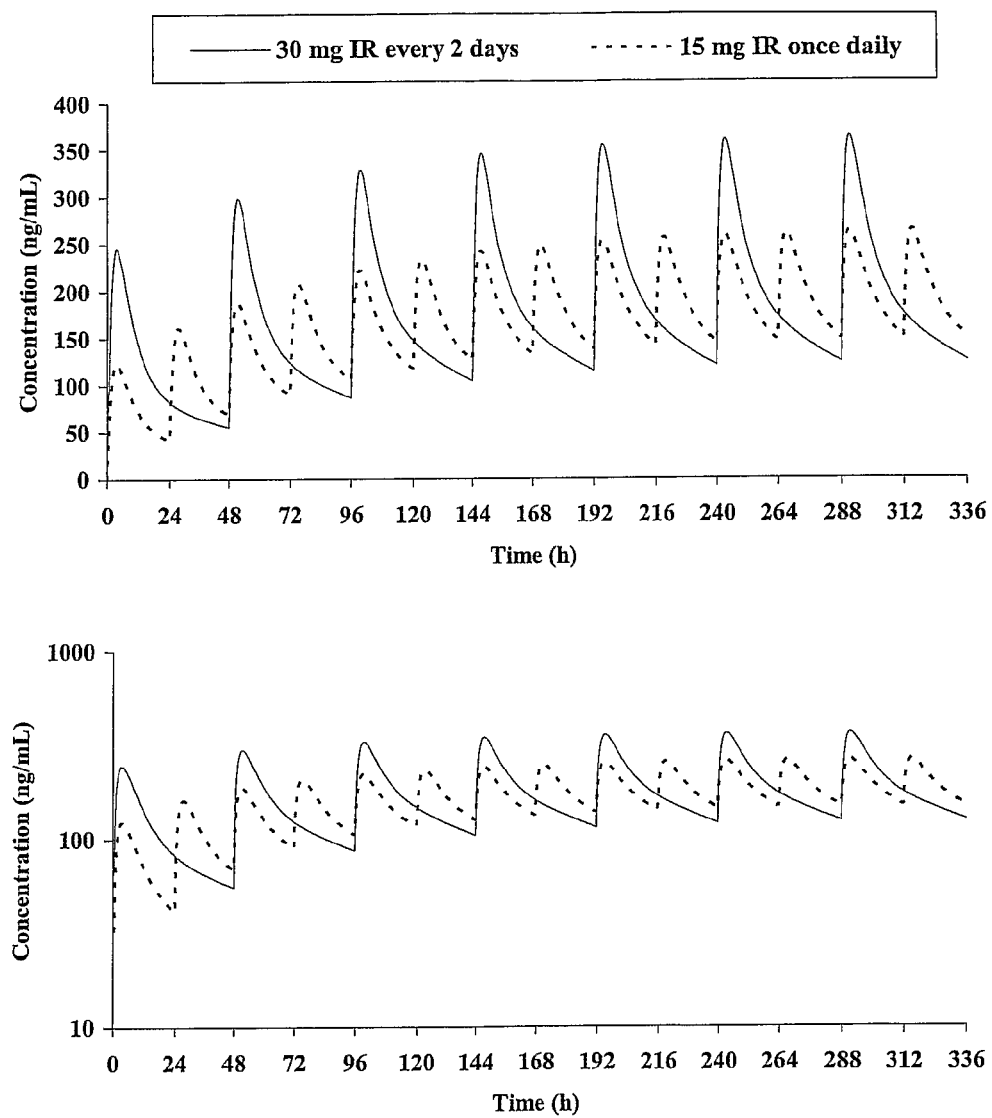

Figure 7: Simulated plasma concentrations of aripiprazole following repeated oral doses of 15 mg aripiprazole (IR) administered every other day and 15 mg (IR) administered once daily
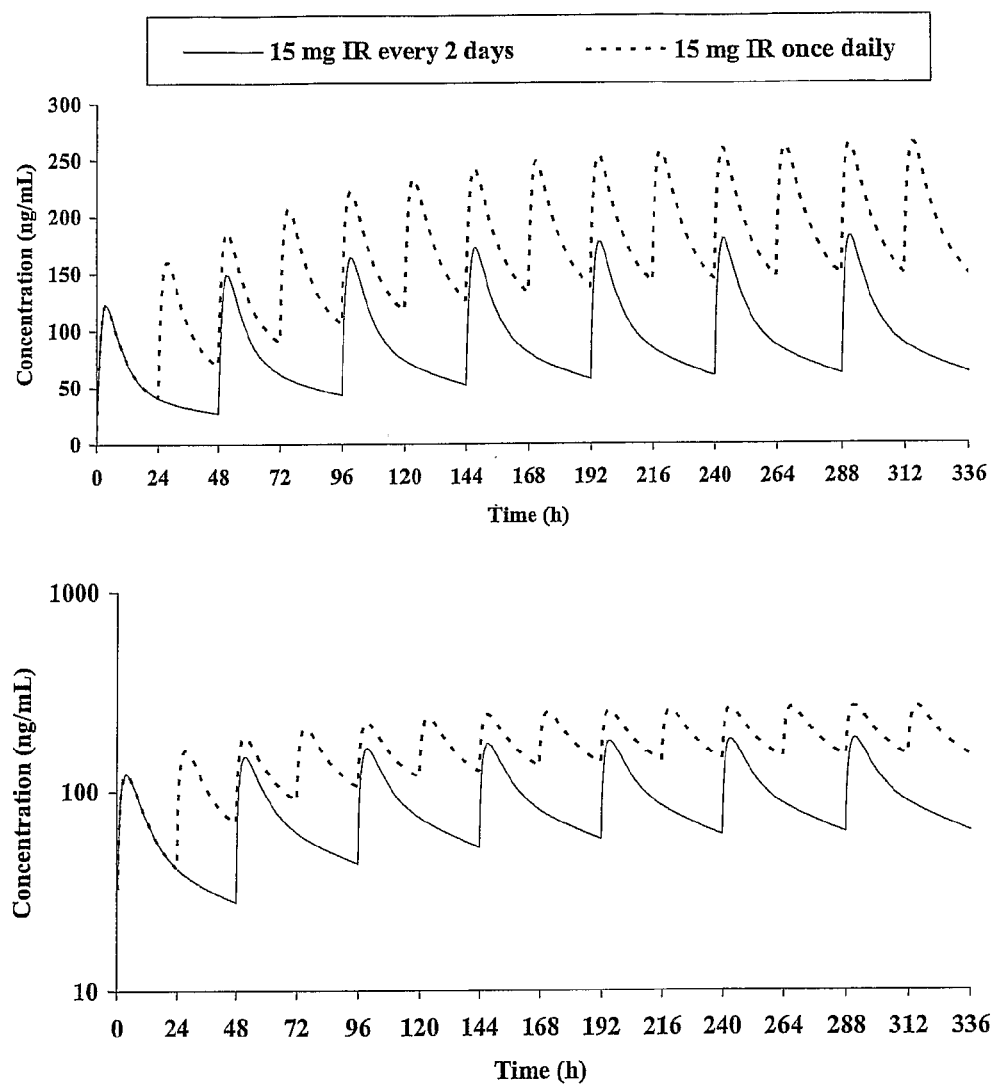

Figure 8: Simulated plasma concentrations of aripiprazole following repeated oral doses of 30 mg aripiprazole (14-h SR) administered every other day and 15 mg (IR) administered once daily
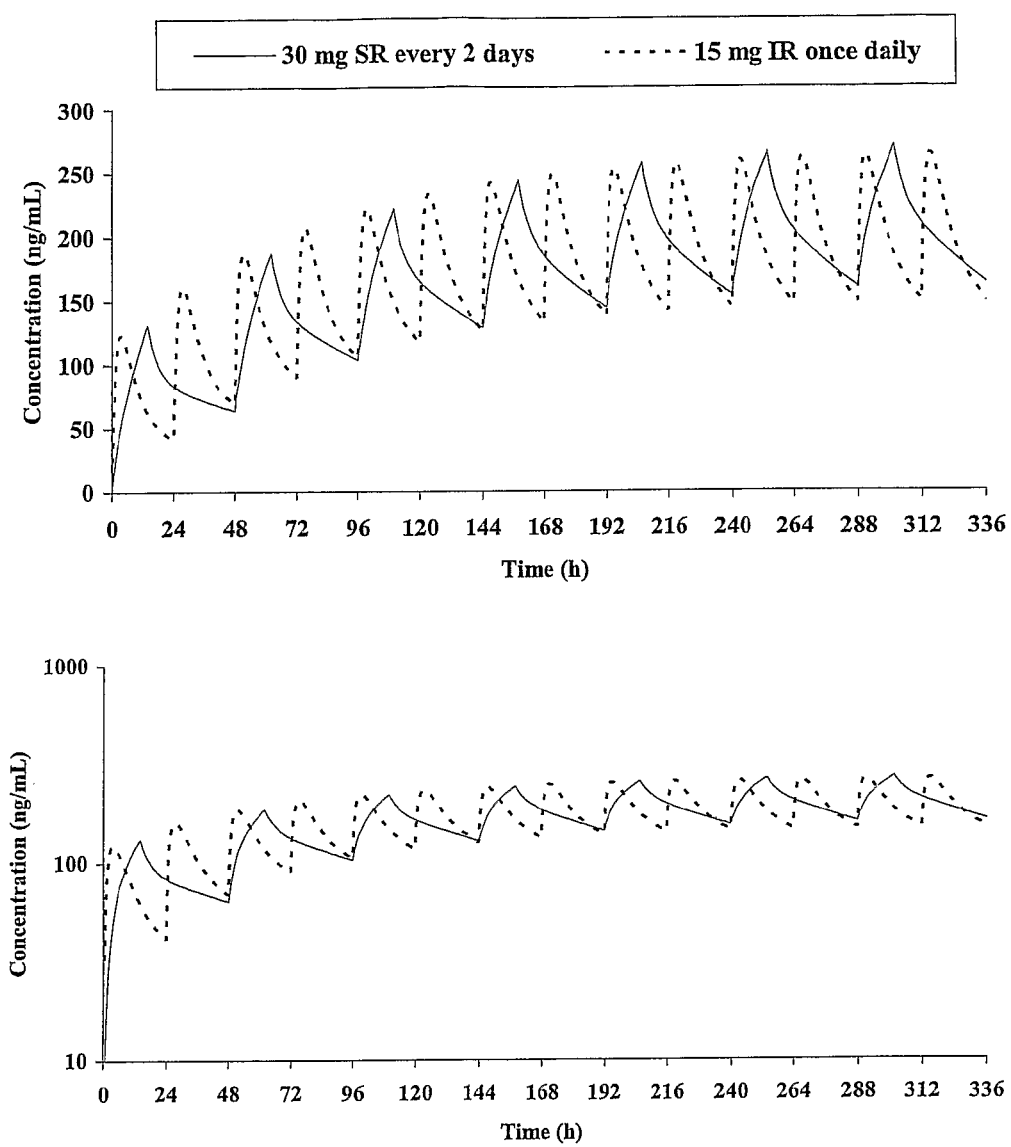

Figure 9: Simulated plasma concentrations of aripiprazole following repeated oral doses of 60 mg aripiprazole (14-h SR) administered weekly and 15 mg (IR) administered once daily
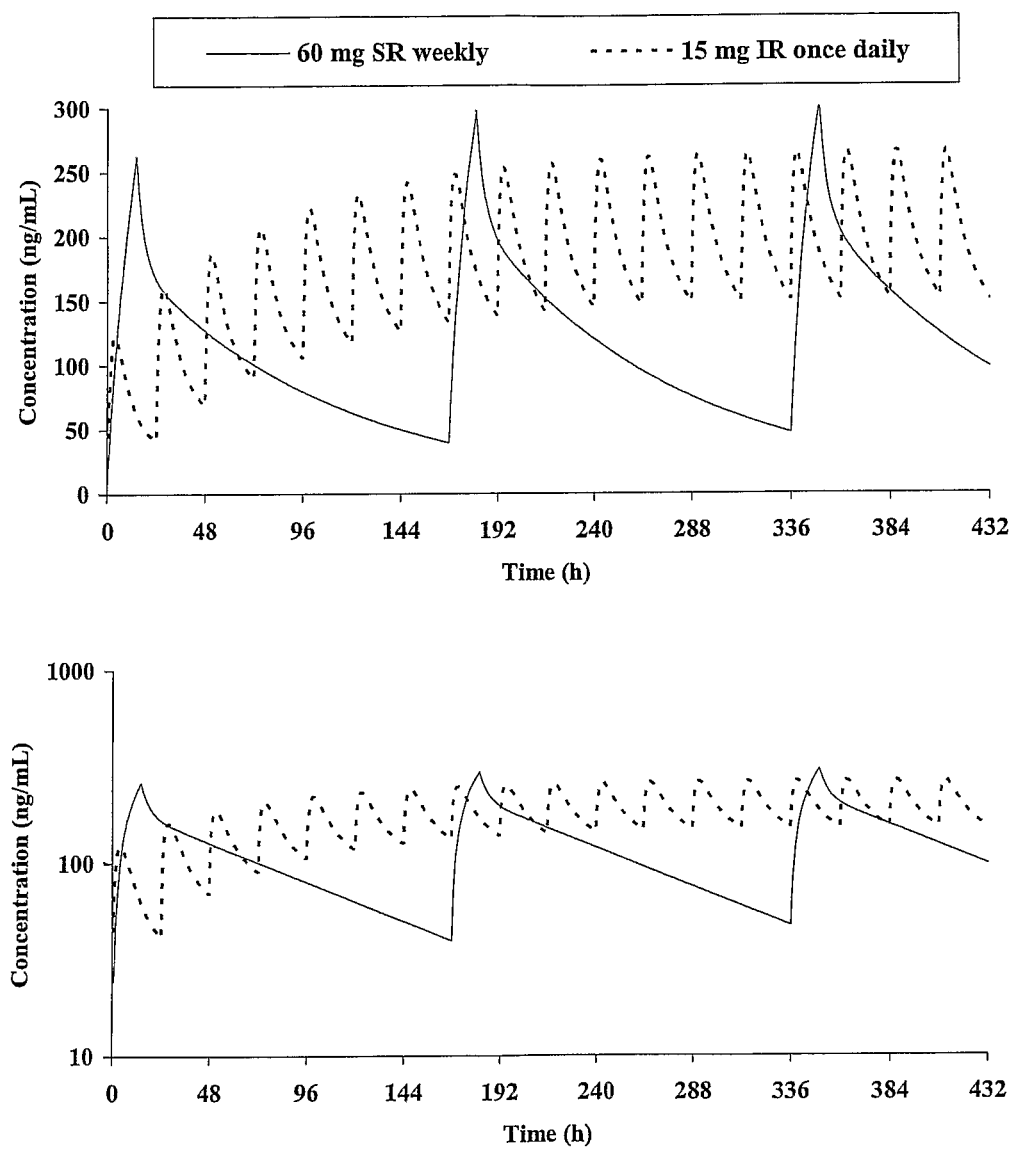

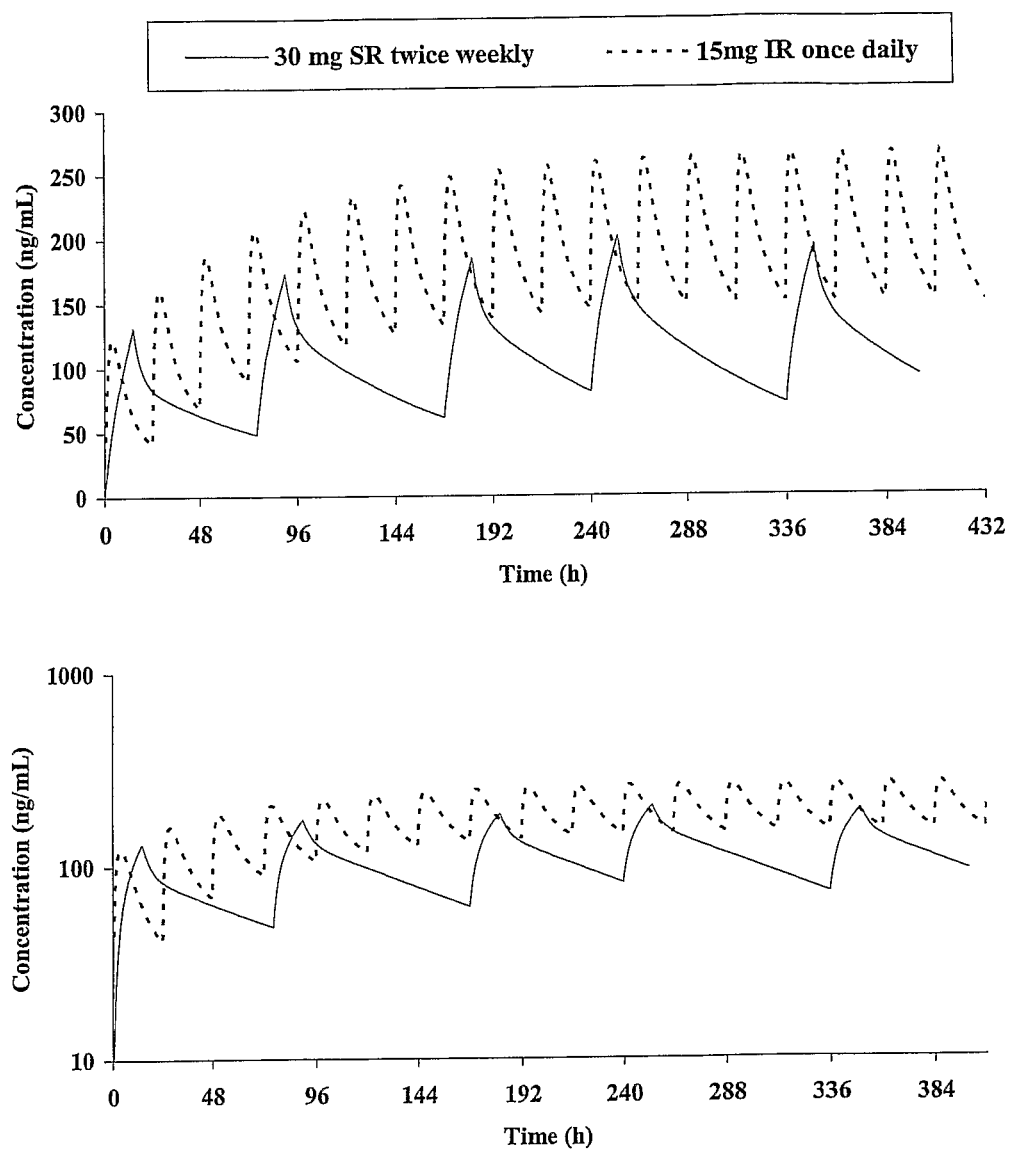
Figure 10: Simulated plasma concentrations of aripiprazole following repeated oral doses of 30 mg aripiprazole (14-h SR) administered twice weekly and 15 mg (IR) administered once daily Figure 11: Simulated plasma concentrations of aripiprazole following repeated oral doses of 45 mg aripiprazole (14-h SR) administered twice weekly and 15 mg (IR) administered once daily
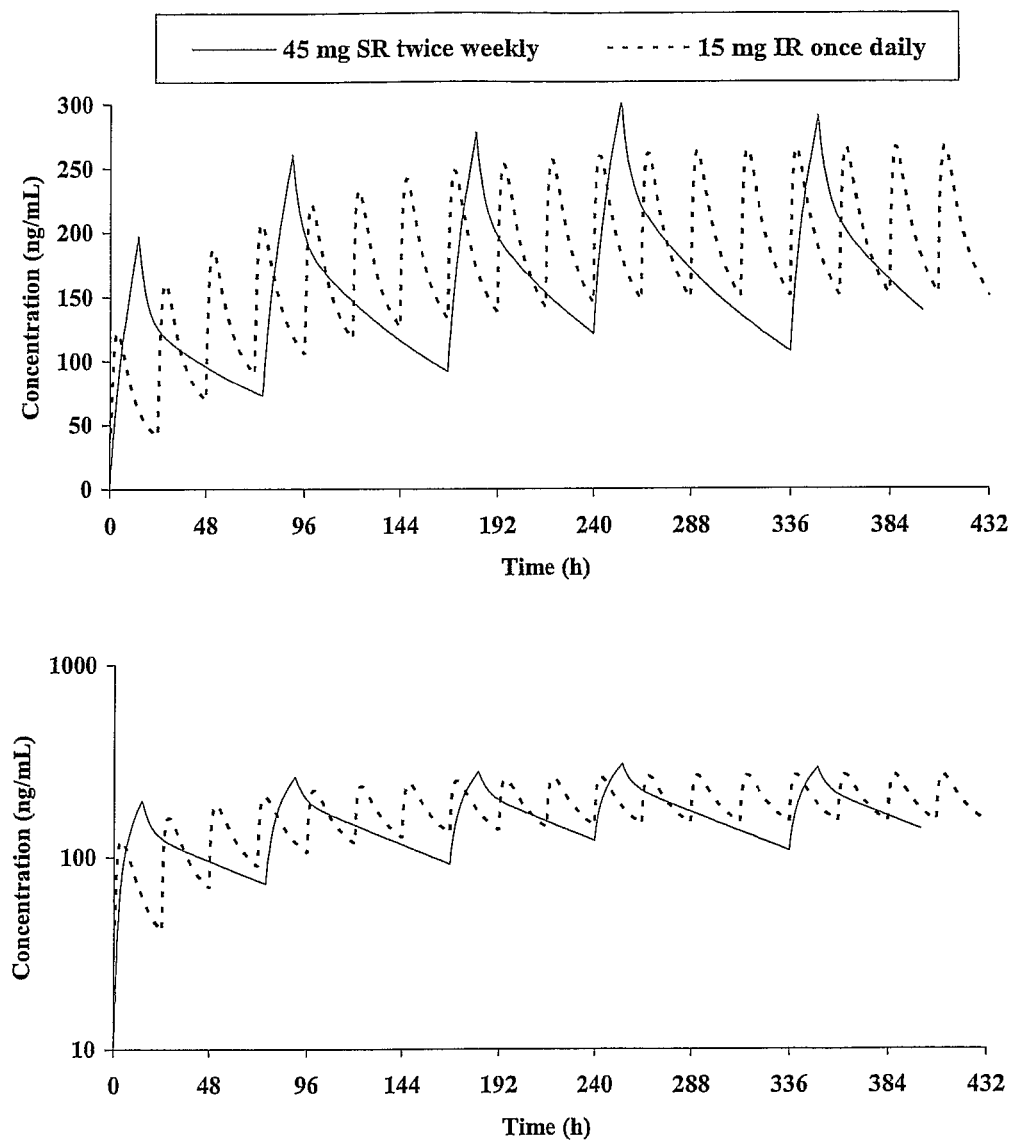

Figure 12: Simulated plasma concentrations of aripiprazole following repeated oral doses of 60 mg aripiprazole (14-h SR) administered twice weekly and 15 mg (IR) administered once daily
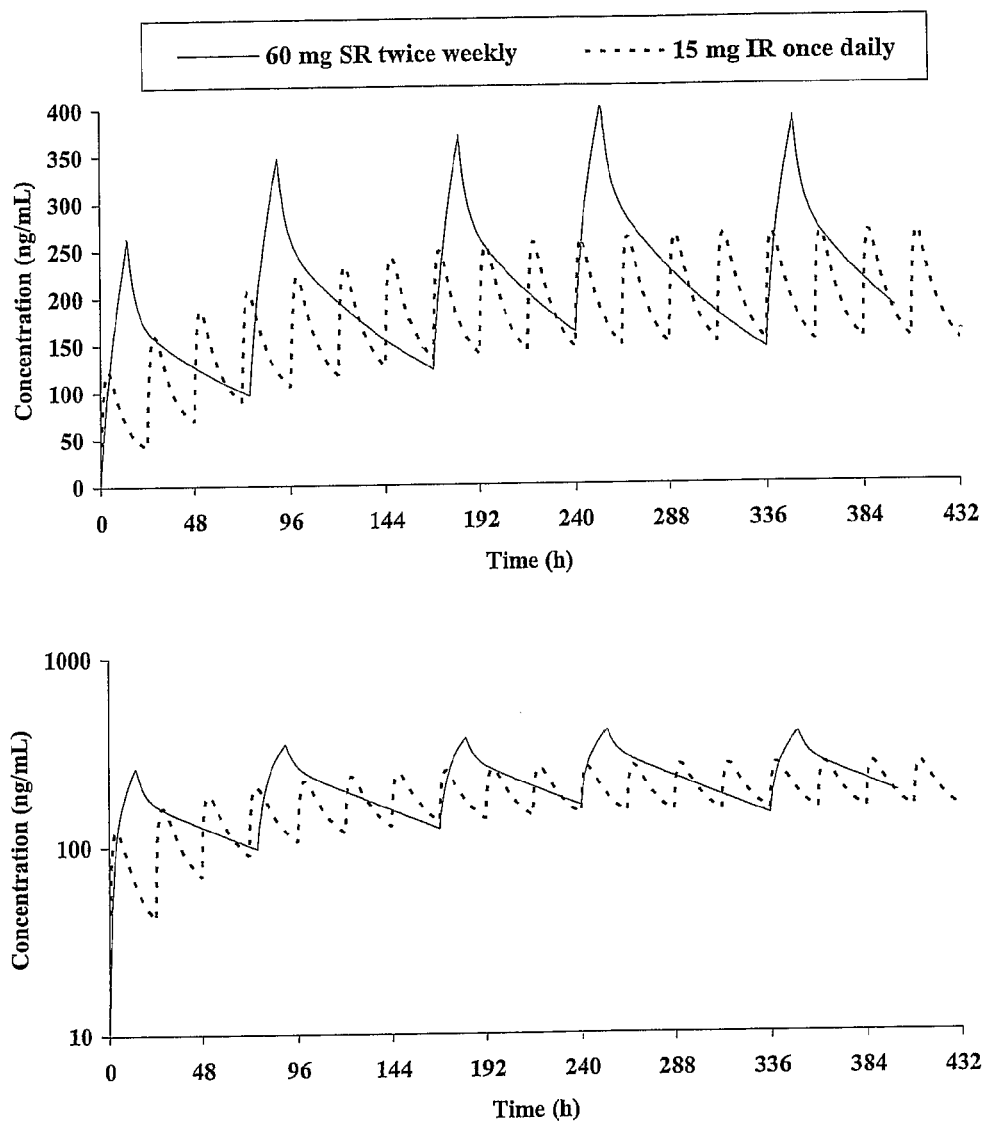

Figure 13: Simulated plasma concentrations of aripiprazole following repeated oral doses of 30 mg aripiprazole (10-h SR) administered every other day and 15 mg (IR) administered once daily
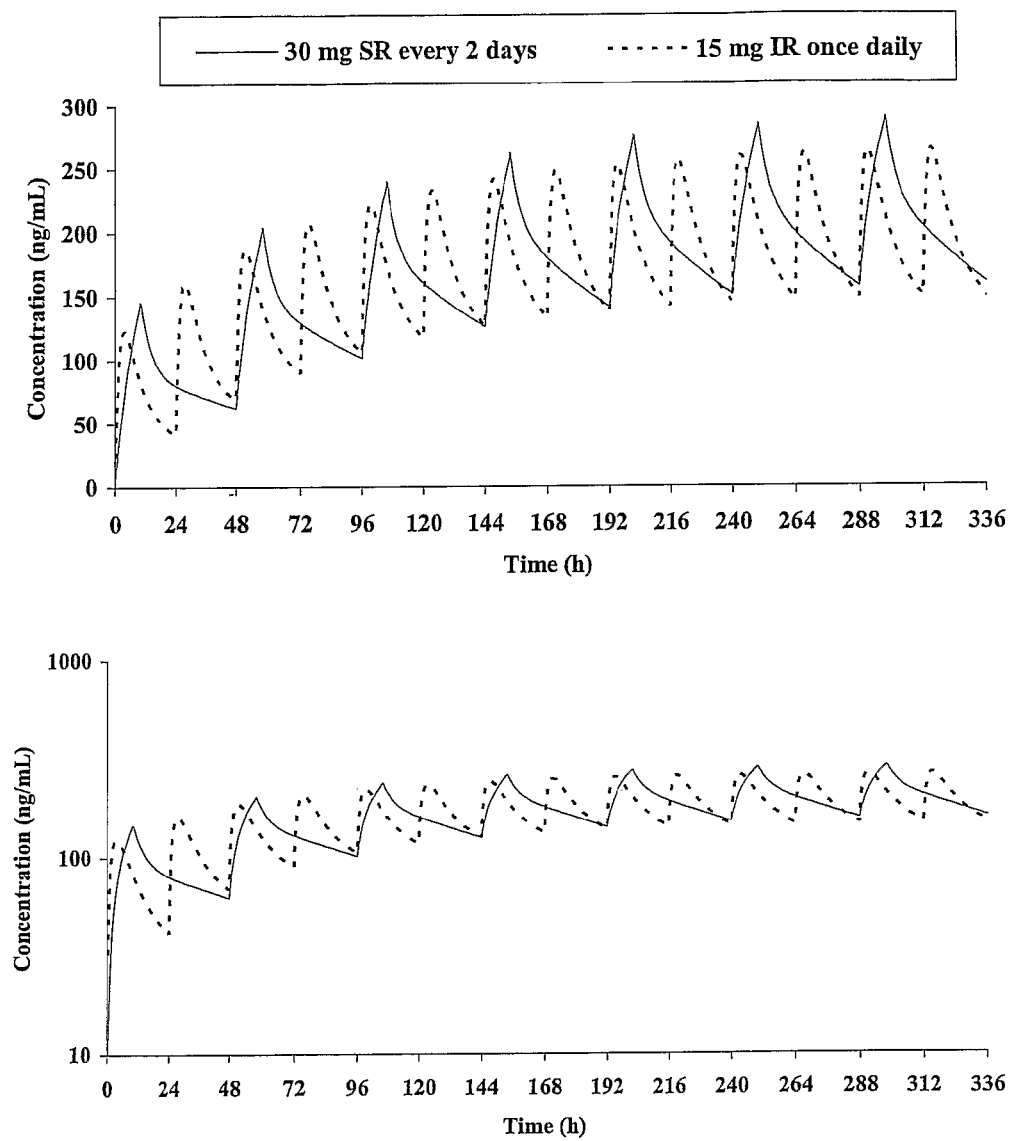

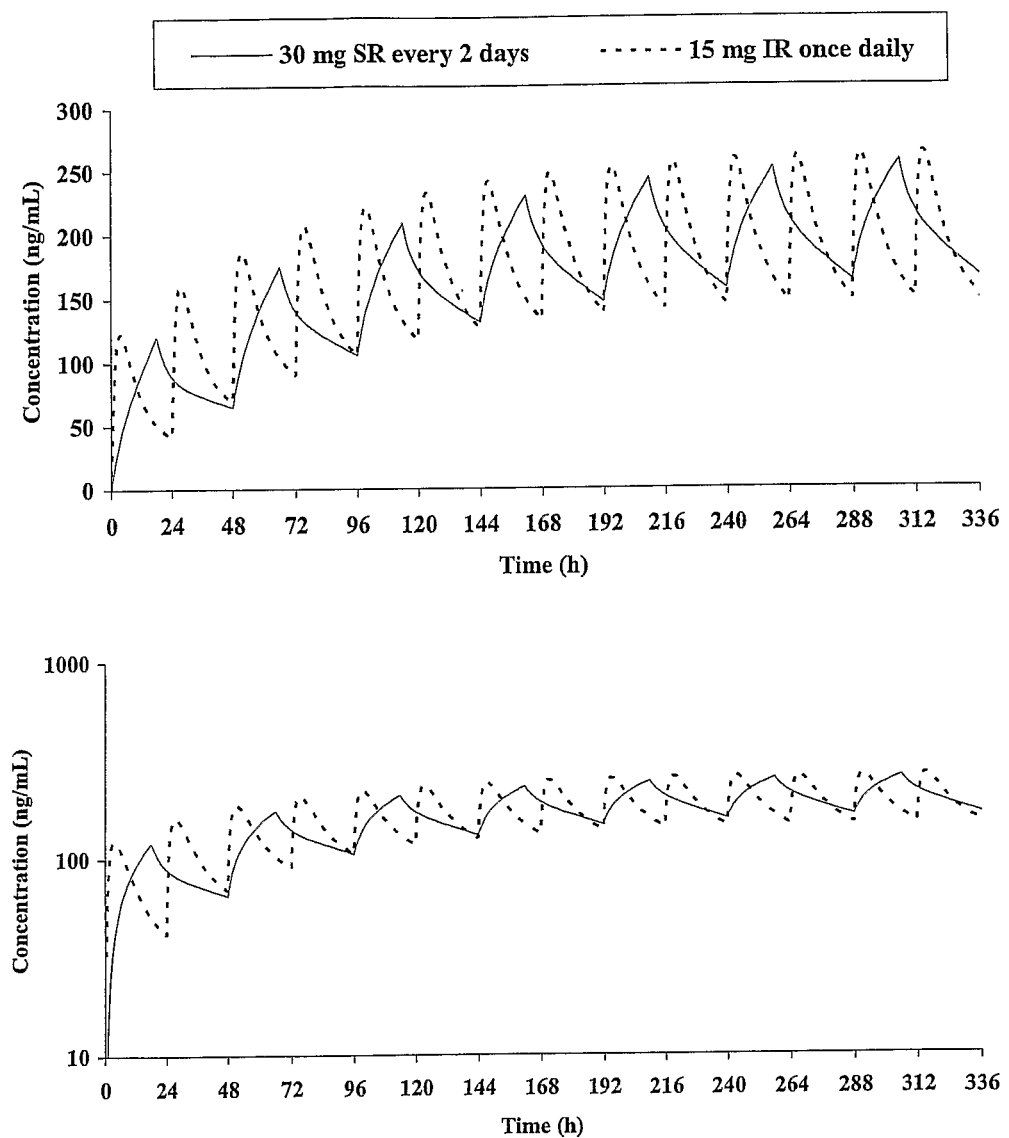
Figure 14: Simulated plasma concentrations of aripiprazole following repeated oral doses of 30 mg aripiprazole (18-h SR) administered every other day and 15 mg (IR) administered once daily Figure 15: Simulated plasma concentrations of aripiprazole following repeated oral doses of 60 mg aripiprazole (10-h SR) administered weekly and 15 mg (IR) administered once daily
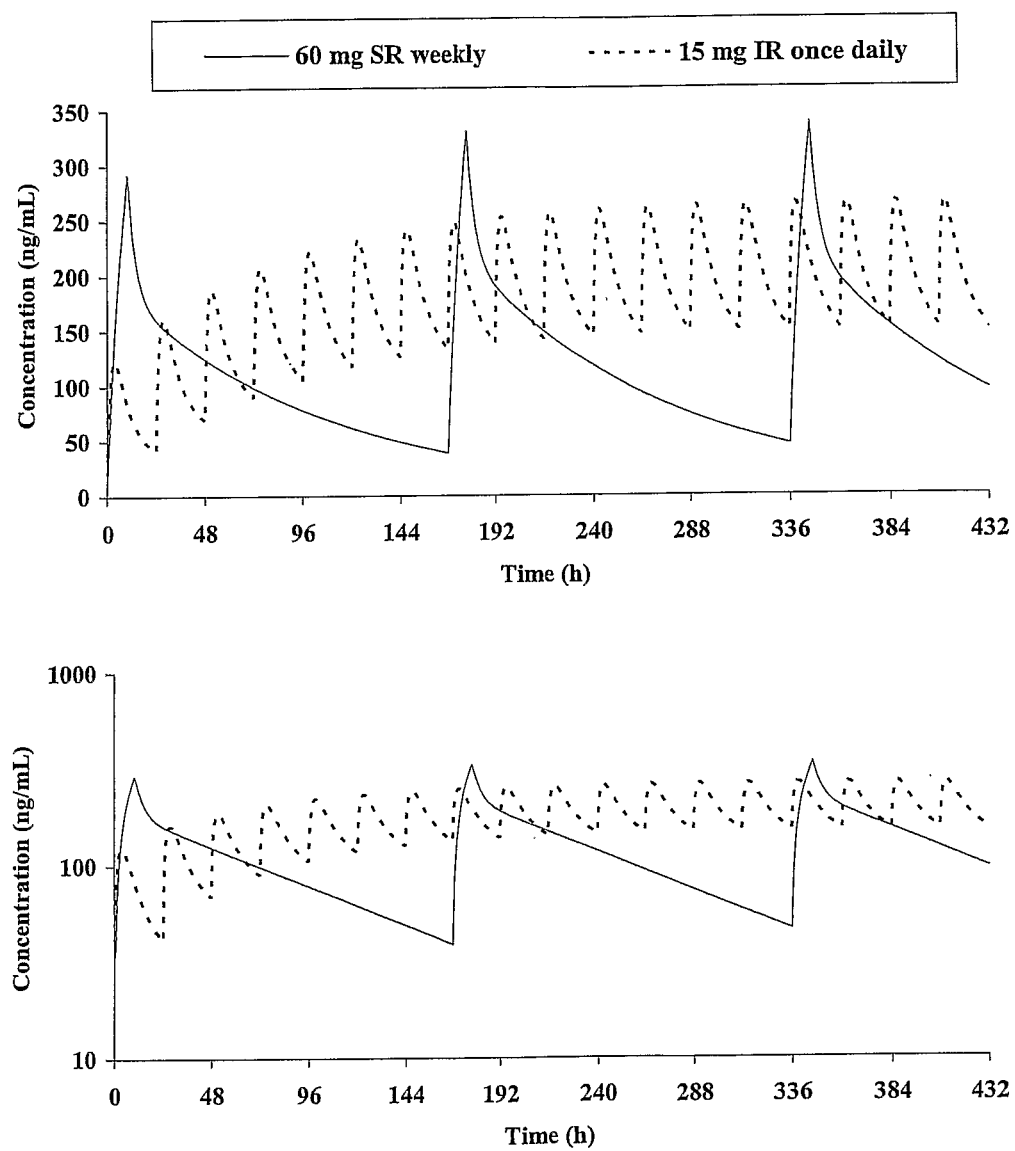

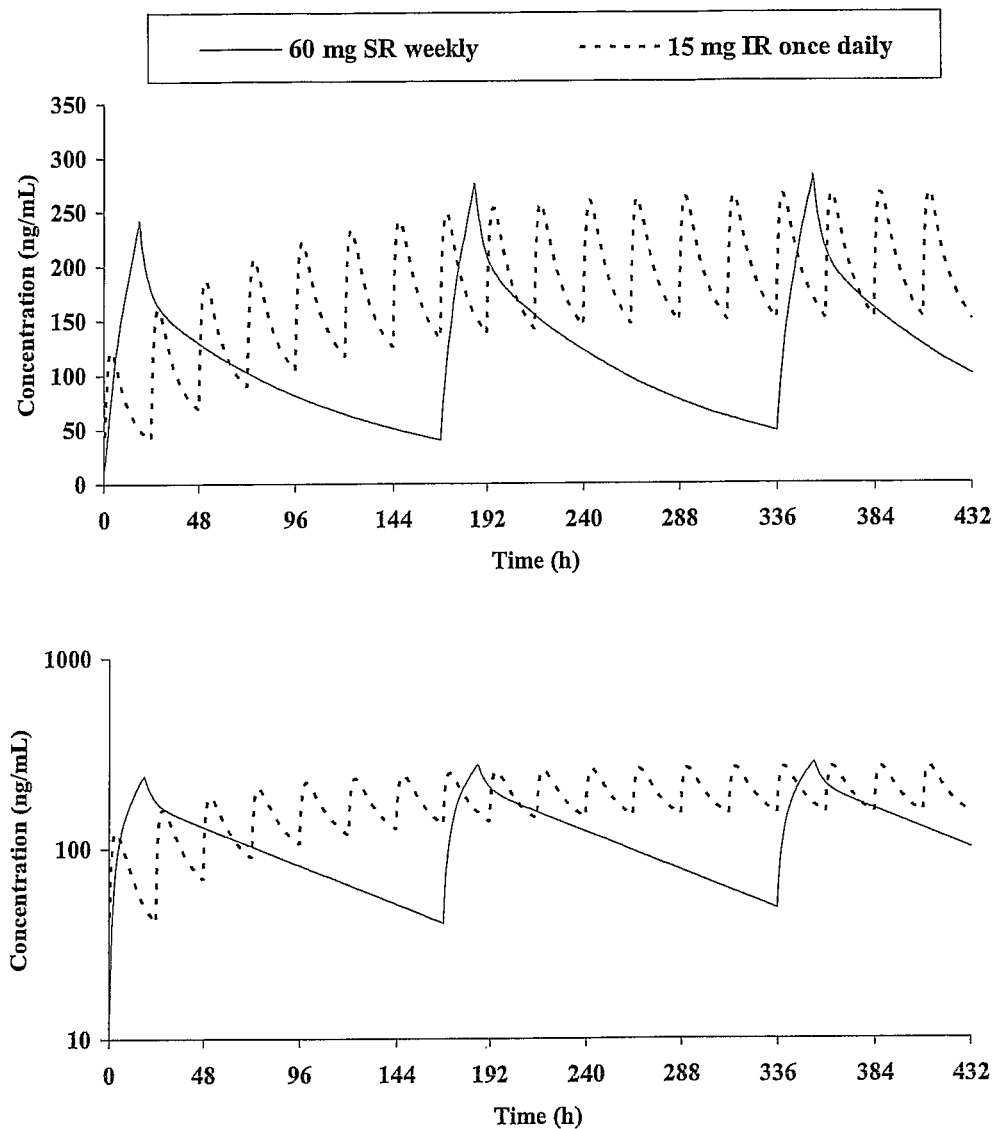
Figure 16: Simulated plasma concentrations of aripiprazole following repeated oral doses of 60 mg aripiprazole (18-h SR) administered weekly and 15 mg (IR) administered once daily Figure 17: Simulated plasma concentrations of aripiprazole following repeated oral doses of 45 mg aripiprazole (10-h SR) administered twice weekly and 15 mg (IR) administered once daily
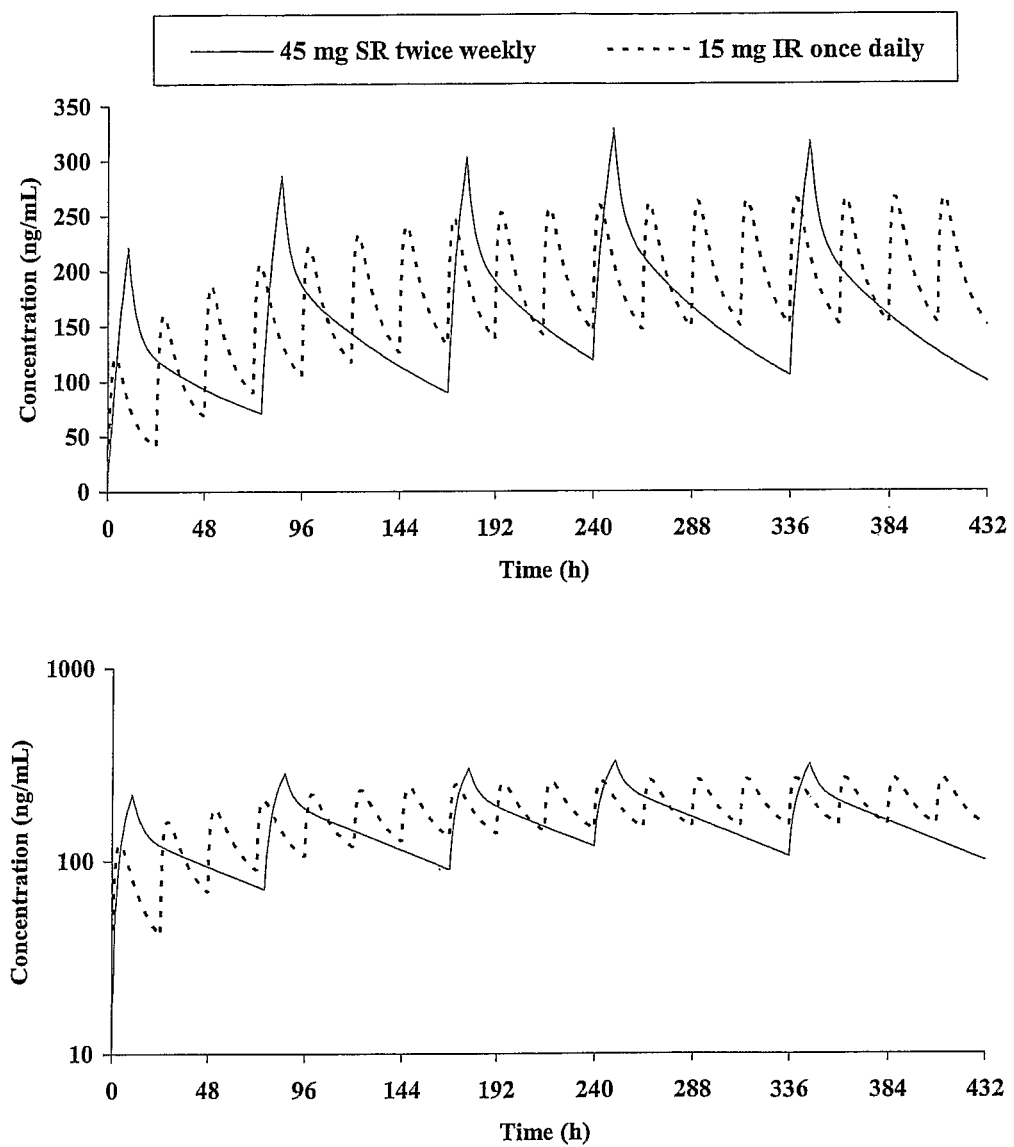

Figure 18: Simulated plasma concentrations of aripiprazole following repeated oral doses of 45 mg aripiprazole (18-h SR) administered twice weekly and 15 mg (IR) administered once daily
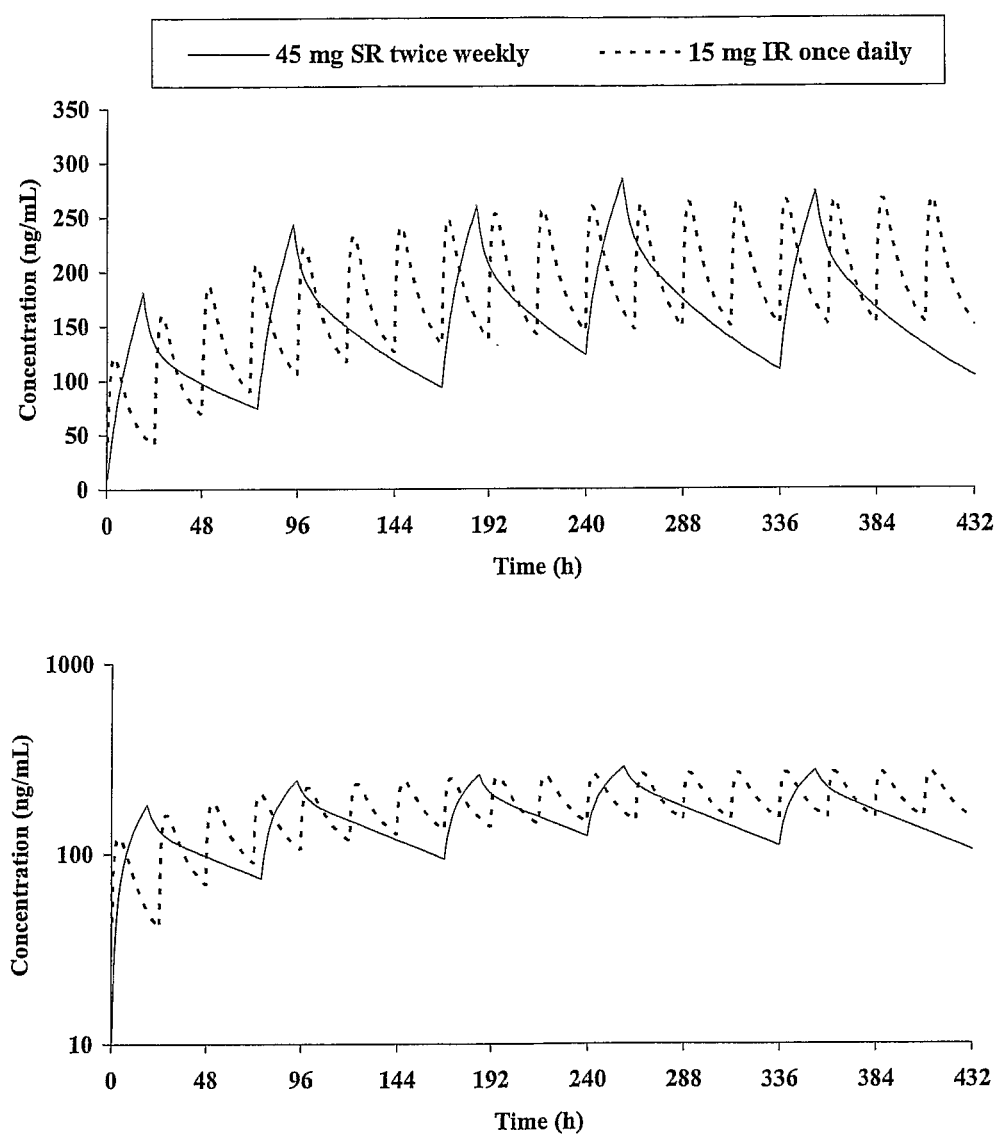

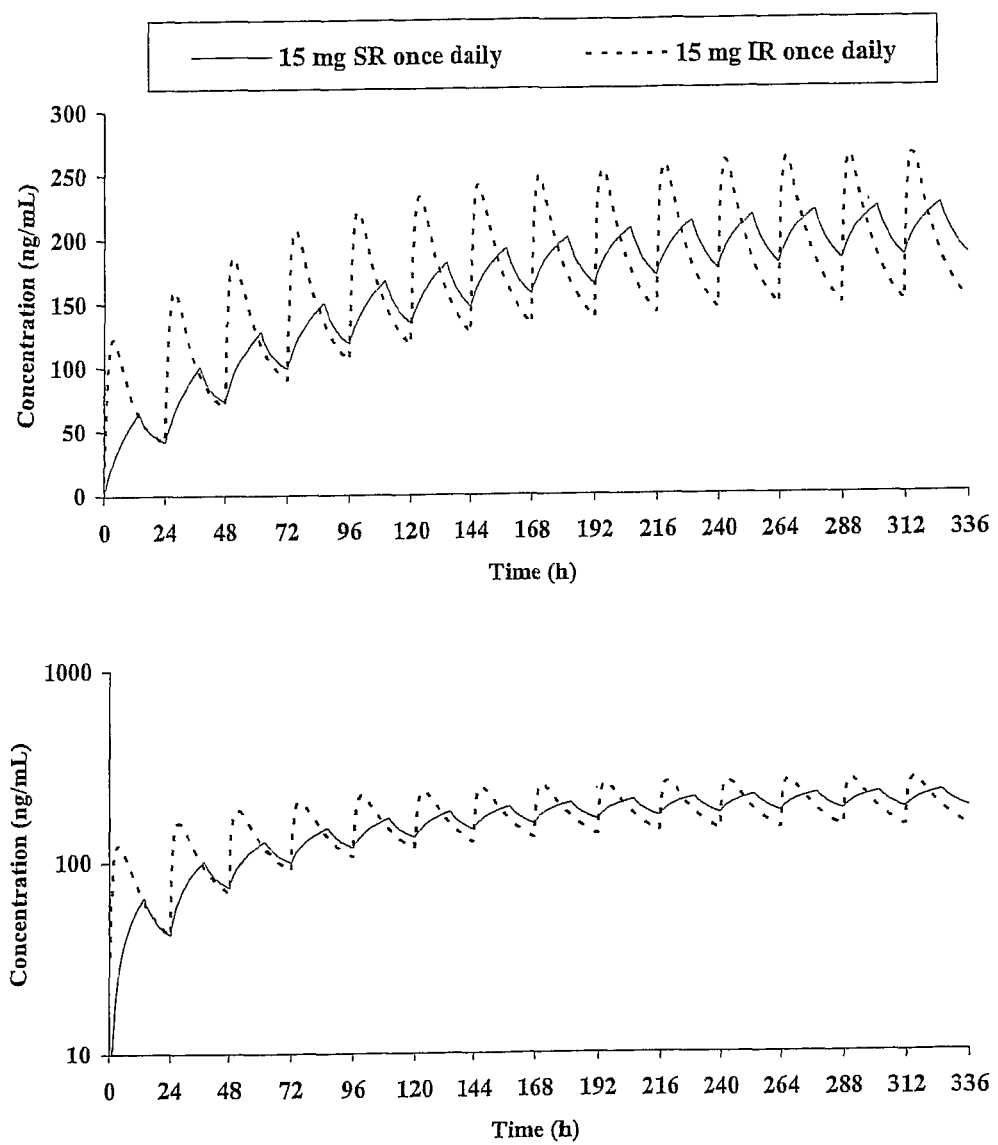
Figure 19: Simulated plasma concentrations of aripiprazole following repeated oral doses of 15 mg aripiprazole (14-h SR) administered once-daily and 15 mg (IR) administered once daily

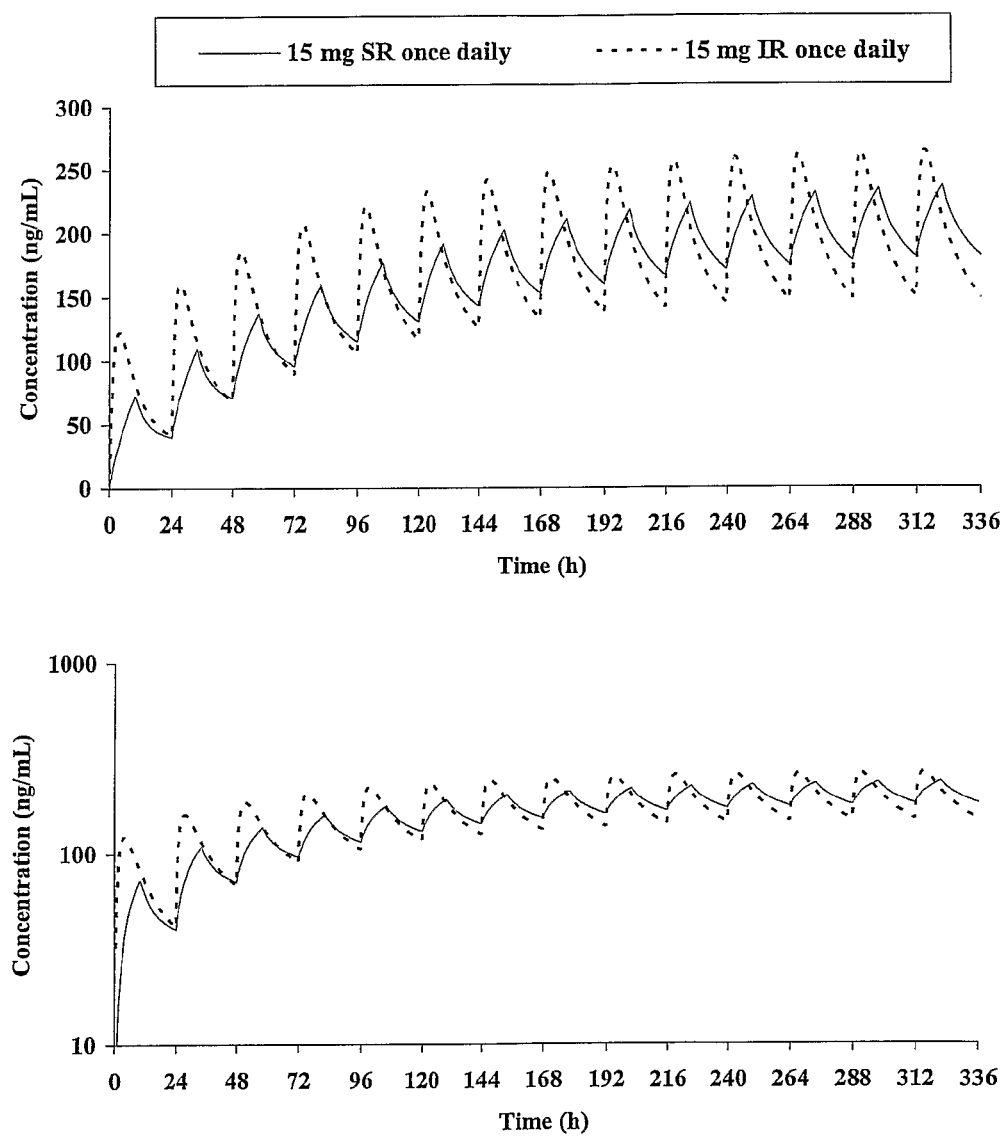
Figure 20: Simulated plasma concentrations of aripiprazole following repeated oral doses of 15 mg aripiprazole (10-h SR) administered once-daily and 15 mg (IR) administered once daily

PHARMACEUTICAL COMPOSITIONS OF ARIPIPRAZOLE

CROSS-REFERENCE TO RELATED APPLICATION

This application is a Section 371 of International Application No. PCT/GB2007/003677, filed Sep. 26, 2007, which was published in the English language on Apr. 3, 2008 under International Publication No. WO 2008/038003 A3, and the entire disclosure of which is incorporated herein by reference.

The invention relates to pharmaceutical formulations comprising aripiprazole. More particularly, the invention relates to orally deliverable pharmaceutical compositions for the controlled release of aripiprazole.

Aripiprazole is 7-[4-[4-(2,3-dichlorophenyl)piperazin-1-yl]butoxy]-3,4-dihydro-1H-quinolin-2-one and has the following structure:

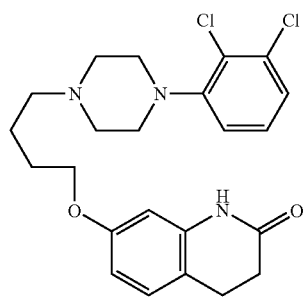 [SMILES: O=C1CCc2ccc(OCCCCN3CCN(c4cccc(Cl)c4Cl)CC3)cc2N1]

Aripiprazole appears to mediate its antipsychotic effects primarily by partial agonism at the D2 receptor. Partial agonism at D2 receptors has been shown to modulate dopaminergic activity in areas where dopamine activity may be high or low, such as the mesolimbic and mesocortical areas of the schizophrenic brain, respectively. In addition to partial agonist activity at the D2 receptor, aripiprazole is also a partial agonist at the 5-HT1A receptor, and like the other atypical antipsychotics, aripiprazole displays an antagonist profile at the 5-HT2A receptor. Aripiprazole has moderate affinity for histamine and alpha adrenergic receptors, and no appreciable affinity for cholinergic muscarinic receptors. Aripiprazole is currently used for the treatment of schizophrenia and acute manic/mixed episodes associated with Bipolar I Disorder.

Clinical activity is thought to be primarily due to the parent drug, aripiprazole, and to a lesser extent, to its major metabolite, dehydro-aripiprazole, which has been shown to have affinities for D2 receptors similar to the parent drug and represents 40% of the parent drug exposure in plasma (see ABILIFY® (aripiprazole) prescribing information, Otsuka Pharmaceutical Co., Ltd, Tokyo, 101-8535, June 2006). The mean elimination half-lives are about 75 hours and 94 hours for aripiprazole and dehydro-aripiprazole, respectively. Steady-state concentrations are attained within 14 days of initial dosing for both active moieties. Aripiprazole accumulation is predictable from single-dose pharmacokinetics. At steady state, the pharmacokinetics of aripiprazole are dose-proportional. Elimination of aripiprazole is mainly through hepatic metabolism involving two Cytochrome P450 isozymes, CYP2D6 and CYP3A4 (Kubo M et al Influence of itraconazole co-administration and CYP2D6 genotype on the pharmacokinetics of the new antipsychotic ARIPIPRAZOLE. Drug Metab Pharmacokinet. February 2005; 20(1): 55-64).

Aripiprazole is well absorbed after administration of the immediate release (IR) tablet, with peak plasma concentrations occurring within 3 to 5 hours after dosing; the absolute oral bioavailability of the IR tablet formulation is 87%. Administration of a 15-mg aripiprazole IR tablet with a standard high-fat meal does not significantly affect the Cmax or AUC of aripiprazole or its active metabolite, dehydro-aripiprazole, but delays Tmax by 3 hours for aripiprazole and 12 hours for dehydro-aripiprazole. Aripiprazole is also well absorbed when administered orally as the solution. At equivalent doses, the plasma concentrations of aripiprazole from the solution were higher than that from an IR tablet formulation.

In a relative bioavailability study comparing the pharmacokinetics of 30 mg aripiprazole as an oral solution to 30 mg aripiprazole IR tablets in healthy subjects, the solution to tablet ratios of geometric mean Cmax and AUC values were 122% and 114%, respectively. The steady-state volume of distribution of aripiprazole following intravenous administration is high (404 L or 4.9 L/kg), indicating extensive extravascular distribution. At therapeutic concentrations, aripiprazole and its major metabolite are greater than 99% bound to serum proteins, primarily to albumin. In healthy human volunteers administered 0.5 to 30 mg/day aripiprazole for 14 days, there was dose-dependent D2 receptor occupancy indicating brain penetration of aripiprazole in humans (Swainston Harrison T and Perry C M. Aripiprazole: a review of its use in schizophrenia and schizoaffective disorder. Drugs. 2004; 64(15): 1715-36).

Aripiprazole is metabolized primarily by three biotransformation pathways: dehydrogenation, hydroxylation, and N-dealkylation. Based on in vitro studies, CYP3A4 and CYP2D6 enzymes are responsible for dehydrogenation and hydroxylation of aripiprazole, and N-dealkylation is catalyzed by CYP3A4. Aripiprazole is the predominant drug moiety in the systemic circulation. At steady state, dehydro-aripiprazole, the active metabolite, represents about 40% of aripiprazole AUC in plasma.

Approximately 8% of Caucasians lack the capacity to metabolize CYP2D6 substrates and are classified as poor metabolizers (PM), whereas the rest are extensive metabolizers (EM). PMs have about an 80% increase in aripiprazole exposure and about a 30% decrease in exposure to the active metabolite compared to EMS, resulting in about a 60% higher exposure to the total active moieties from a given dose of aripiprazole compared to Ems. The mean elimination half-lives are about 75 hours and 146 hours for aripiprazole in EMs and PMs, respectively. Aripiprazole does not inhibit or induce the CYP2D6 pathway.

Following a single oral dose of [$^{14}$C]-labeled aripiprazole, approximately 25% and 55% of the administered radioactivity was recovered in the urine and feces, respectively. Less than 1% of unchanged aripiprazole was excreted in the urine and approximately 18% of the oral dose was recovered unchanged in the feces.

The recommended starting and target dose for aripiprazole in schizophrenia is 10 or 15 mg/day administered on a once-a-day schedule without regard to meals. If an increased dosage is required it is recommended that this should not be made before 2 weeks; the time needed to achieve steady state. In bipolar disease, the starting dose is 30 mg given once a day. However, in a phase III clinical trials, approximately. 15% of patients had their dose decreased to 15 mg based on assessment of tolerability (Drugs at FDA; Abilify (NDA#021436 Tablet Oral)).

The listing or discussion of a prior-published document in this specification should not necessarily be taken as an acknowledgement that that document is part of the state of the art or is common general knowledge.

There are a number of disadvantages associated with the dosage regimen for aripiprazole described above for treating schizophrenia, bipolar disease and other CNS conditions. Market research suggests that patients much prefer oral medications that can be taken as infrequently as possible and that are well tolerated. The once daily oral administration dosage regime may be considered too frequent for many patients. In addition, a significant subset of the target population for aripiprazole is likely to be patients that are both elderly and forgetful. Such patients often require time consuming and expensive supervised administration.

The subject invention seeks to address one or more of the above-mentioned deficiencies by the provision of an orally deliverable pharmaceutical composition for the controlled release of aripiprazole. The composition comprises a therapeutically effective amount of aripiprazole and at least one pharmaceutically acceptable excipient. These compositions (hereinafter denoted "the compositions of the invention" unless otherwise stated) may be used for the treatment of schizophrenia, bipolar disease and a number of other medical indications as described later in this specification.

The compositions of the invention are believed to have advantages such as (but not limited to) one or more of the following advantages.

Typically, the compositions of the invention control (e.g. delay, prolong or sustain) the release of an aripiprazole dose so that after administration, the adverse event profile is reduced, or at least not significantly increased, compared to the current dosage regimen.

Put another way, the compositions of the invention allow greater quantities of aripiprazole to be administered in one dose without significantly increasing adverse events compared to the current once daily conventional IR dosing regimen. Any reduction in dosing frequency is thought to bring material improvements in patient convenience and compliance.

Reduction in dosing frequency offers significant pharmacoeconomic advantages over the current dosing regimen by reducing the indirect human cost of drug treatment (e.g. by reducing medical practitioners' time required for supervised drug administration).

The compositions of the invention also provide a once daily dosage regimen in which the release of aripiprazole is controlled. It is thought that this could reduce the adverse event profile compared to currently available once daily dosage regimens and/or provide a more efficient once daily dose regimen.

Unless otherwise indicated herein, the term "aripiprazole" refers to 7-[4-[4-(2,3-dichlorophenyl)piperazin-1-yl]butoxy]-3,4-dihydro-1H-quinolin-2-one, its pharmaceutically acceptable salts, and mixtures thereof. "Pharmaceutically acceptable salts" includes derivatives of aripiprazole, wherein aripiprazole is modified by making non-toxic acid or base salts thereof, and further refers to pharmaceutically acceptable solvates (including hydrates) of such salts. Examples of pharmaceutically acceptable salts include, but are not limited to, mineral or organic acid salts of the amine functionality of aripiprazole. The pharmaceutically acceptable salts include non-toxic salts and the quaternary ammonium salts of aripiprazole formed, for example, from organic and inorganic acids. Such salts include those derived from inorganic acid such hydrochloric, hydrobromic, hydroiodic, sulphuric, phosphoric, nitric, metal salts such as sodium salt, potassium salt and cesium salt, alkaline earth metal salts such as calcium salt and magnesium salt and combinations of the foregoing. Pharmaceutically acceptable organic salts include salts prepared from organic acids such as acetic, trifluoroacetic propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethanedisulfonic, oxalic, isethionic, $HO_2C-(CH_2)_n-CO_2H$ (where n=0-4) and salts prepared from amino acids such as arginate, asparginate and glutamate. Preferred pharmaceutically acceptable organic salts include salts prepared from organic acids such as acetic, trifluoroacetic propionic, succinic, glycolic, stearic, lactic, malic, tartaric, citric, ascorbic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethanedisulfonic, oxalic, isethionic, $HO_2C-(CH_2)_n-CO_2H$ (where n=0-4) and salts prepared from amino acids such as arginate, asparginate and glutamate. The term "pharmaceutically acceptable salts" also includes mixtures of any of the foregoing derivatives of aripiprazole.

By the term "orally deliverable", we include the meaning suitable for oral, including peroral and intra-oral (e.g. sublingual or buccal) administration. Preferably, the compositions of the invention are designed for peroral administration to a patient, i.e. by swallowing (e.g. eating or drinking).

By the term "controlled release", we include the meaning that after administration, release of the aripiprazole is controlled so that a dosage regimen in which aripiprazole can be administered less frequently than the current dosage regimen, for example less frequently than once daily can be provided (however, improved release profiles for once daily administration are also included in this regard). This may include delaying and/or prolonging and/or sustaining the release of aripiprazole so that the time between doses of aripiprazole can be increased. Such delayed/prolonged/sustained release may also be accompanied by a higher single dose of aripiprazole in the compositions of the invention compared to the currently used once daily IR formulations.

The compositions of the invention are suitable for a controlled release once daily (OD) dose regimen, and dose regimens less frequent than OD. By dose regimens less frequent than OD, we include once every 2, 3, 4, 5 or 6 days, thrice weekly, twice weekly (TW), once weekly (OW) and combinations thereof. A preferred group of dose regimens are OD, once every 2 days (i.e. every other day), TW and OW, for example once every 2 days, TW and OW.

The controlled release characteristics of the compositions of the invention may be defined in relation to their in vitro or in vivo release profile or related values such as $C_{max}$, $T_{max}$ and AUC, as described in more detail below.

For example, the compositions of the invention may exhibit an in vitro release profile wherein on average no more than about 60% of the aripiprazole, preferably no more than about 50%, more preferably no more than about 40% is dissolved within 3 hours after placement in a standard dissolution test.

Unless otherwise indicated, as used herein, the term "standard dissolution test", means a test conducted according to the "Paddle Method" at 100 rpm in 900 ml of a dissolution medium of aqueous physiological pH range between 1 and 7 at 37° C., as described in the United States Pharmacopoeia, or other test conditions substantially equivalent thereto, e.g. 0.1 M hydrochloric acid and pH 4.0 phosphate buffer.

As noted above, the subject invention is concerned with providing dosage regimens with either less frequent dosing than the current once daily dosage regimen or controlled delivery of the daily dose. Compositions having the in vitro release profile defined above may be suitable for both OD administration and dose regimens requiring even less frequent administration of the drug containing composition than OD, as explained in more detail below.

For the avoidance of doubt, by the phrase "dose regimens requiring even less frequent administration of the drug containing composition than OD", as used herein in relation to the compositions of the invention having the controlled release characteristics described herein (e.g. in vitro release profile), we include once every 2, 3, 4, 5 or 6 days, thrice weekly, twice weekly (TW), once weekly (OW) and combinations thereof.

The compositions of the invention which may be suitable for OD administration may typically exhibit an in vitro release profile wherein on average from about 10 to about 50%, such as from about 15 to about 45%, for example from about 15 to about 30% of the aripiprazole is dissolved within 3 hours after placement in a standard dissolution test.

The compositions of the invention which may be suitable for dose regimens requiring even less frequent administration of the drug containing composition than OD may typically exhibit an in vitro release profile wherein on average from about 2 to about 40% (e.g. about 2 to about 30 or 35%), such as from about 5 to about 25%, for example from about 10 to about 20% of the aripiprazole is dissolved within 3 hours after placement in a standard dissolution test.

The compositions of the invention which may be suitable for OD administration may typically exhibit an in vitro release profile wherein on average from about 25 to about 100%, such as from about 30 to about 100%, for example from about 40 to about 100% or about 50 to about 100% of the aripiprazole is dissolved within 8 hours after placement in a standard dissolution test.

The compositions of the invention which may be suitable for dose regimens requiring even less frequent administration of the drug containing composition than OD may typically exhibit an in vitro release profile wherein on average no more than about 70% of the aripiprazole, preferably no more than about 60%, more preferably no more than about 50%, for example no more than about 40% is dissolved within 8 hours after placement in a standard dissolution test. Typically, such compositions exhibit an in vitro release profile wherein on average from about 10 to about 65%, such as from about 15 to about 55%, for example from about 20 to about 45% of the aripiprazole is dissolved within 8 hours after placement in a standard dissolution test.

The compositions of the invention may exhibit an in vitro dissolution rate after placement in a standard dissolution test wherein:
from about 2 to about 50% of the aripiprazole is released after 2 hours;
from about 5 to about 80% of the of the aripiprazole is released after 4 hours;
25% or more of the aripiprazole is released after 8 hours; and
40% or more of the aripiprazole is released after 12 hours.

Preferably, the in vitro release rate is independent of pH between 1 and 7.

Compositions having the in vitro release profile defined above may be suitable for both OD administration and dose regimens requiring even less frequent administration of the drug containing composition than OD, as explained in more detail below.

The compositions of the invention which may be suitable for OD administration may typically exhibit an in vitro dissolution rate after placement in a standard dissolution test wherein:
from about 5 to about 40% (e.g. from 10 to 30%) of the aripiprazole is released after 2 hours;
from about 15 to about 70% (e.g. from 20 to 50%) of the aripiprazole is released after 4 hours; and
50% or more (e.g. 60% or more) of the aripiprazole is released after 8 hours.

Preferably, the in vitro release rate is independent of pH between 1 and 7.

The compositions of the invention which may be suitable for dose regimens requiring even less frequent administration of the drug containing composition than OD may typically exhibit an in vitro dissolution rate after placement in a standard dissolution test wherein:
from about 2 to about 35%, such from about 2 to about 25% (e.g. from 5 to 15%) of the aripiprazole is released after 2 hours;
from about 5 to about 50% (e.g. from 10 to 40) of the aripiprazole is released after 4 hours;
from about 25 to about 80% (e.g. from 30 to 60) of the aripiprazole is released after 8 hours; and
40% or more (e.g. 50% or more) of the aripiprazole is released after 12 hours.

Preferably, the in vitro release rate is independent of pH between 1 and 7.

The compositions of the invention may exhibit an in vivo aripiprazole plasma absorption profile following single dose oral administration wherein the time for 50% of the aripiprazole to be absorbed into the plasma (of a human or animal patient) is at least 2 hours, preferably at least 3 hours, more preferably at least 4 hours (e.g. at least about 5 or 6 hours).

The phrase "aripiprazole plasma absorption profile" is intended to refer to the plasma concentration of aripiprazole over time following administration to a human or animal patient. As known to those skilled in the art, the plasma absorption profile may be measured by deconvolution of continuous release pharmacokinetics versus an immediate release reference.

Compositions having the in vivo release profile defined above may be suitable for both OD administration and dose regimens requiring even less frequent administration of the drug containing composition than OD, as explained in more detail below.

The compositions of the invention which may be suitable for OD administration may typically exhibit an in vivo aripiprazole plasma absorption profile following single dose oral administration wherein the time for 50% of the aripiprazole to be absorbed into the plasma is from about 2 to about 12 hours, such as from about 3 to about 10 hours, for example from about 4 to about 9 hours or from about 5 to about 7 hours (e.g. about 6 hours).

The compositions of the invention which may be suitable for dose regimens requiring even less frequent administration of the drug containing composition than OD may typically exhibit an in vivo aripiprazole plasma absorption profile following single dose oral administration wherein the time for 50% of the aripiprazole to be absorbed into the plasma is from about 6 to about 24 hours, such as from about 7 to about 20 hours, for example from about 8 to about 18 hours or from about 10 to about 16 hours.

The compositions of the invention may also be defined in terms of the amount of aripiprazole which is released from the compositions in vivo at specified periods of time following oral administration. For example, compositions of the invention may typically exhibit a release profile wherein:
from about 2 to about 50% of the aripiprazole is released within 2 hours following administration;

from about 5 to about 80% of the aripiprazole is released within 4 hours following administration;

25% or more of the aripiprazole is released within 8 hours following administration; and 40% or more of the aripiprazole is released within 12 hours following administration.

Compositions having the in vivo release profile defined above may be suitable for both OD administration and dose regimens requiring even less frequent administration of the drug containing composition than OD, as explained in more detail below.

The compositions of the invention which may be suitable for OD administration may typically exhibit an in vivo aripiprazole plasma absorption profile wherein:

from about 5 to about 40% (e.g. from 10 to 30%) of the aripiprazole is released within 2 hours following administration;

from about 15 to about 70% (e.g. from 20 to 50%) of the aripiprazole is released within 4 hours following administration; and 50% or more (e.g. 60% or more) of the aripiprazole is released within 8 hours following administration.

The compositions of the invention which may be suitable for dose regimens requiring even less frequent administration of the drug containing composition than OD typically exhibit an in vivo aripiprazole plasma absorption profile wherein:

from about 2 to about 35%, such from about 2 to about 25% (e.g. from 5 to 15%) of the aripiprazole is released within 2 hours following administration;

from about 5 to about 50% (e.g. from 10 to 40%) by weight of the aripiprazole is released within 4 hours following administration;

from about 25 to about 80% (e.g. from 30 to 60%) of the aripiprazole is released within 8 hours following administration; and 40% or more (e.g. 50% or more) of the aripiprazole is released within 12 hours following administration.

The controlled release characteristics of the compositions of the invention which may be suitable for OD administration may be defined in relation to the peak plasma concentration ($C_{max}$) value of aripiprazole when administered to human or animal patients. For example, the compositions of the invention which may be suitable for OD administration typically exhibit a aripiprazole $C_{max}$ value following oral administration of from about 10 to about 99%, such as from about 20 to about 80%, for example from about 25 to about 70% (e.g. from about 30 to about 60%) of the $C_{max}$ value achieved using a conventional immediate release (IR) dosage form of aripiprazole when administered orally at an identical dose.

The phrase "conventional immediate release (IR) dosage form of aripiprazole" includes the meaning that the dosage form releases substantially all of the aripiprazole contained therein immediately, for example within 30 minutes of administration. In other words, such IR dosage forms typically have substantially no component which acts to delay and/or prolong and/or sustain the release of aripiprazole. This definition is intended to include the compositions of aripiprazole described in the introductory pages of this specification which are currently typically used for the treatment of schizophrenia and bipolar disease The controlled release characteristics of the compositions of the invention which may be suitable for OD administration may be defined by the ratio of the peak plasma concentration ($C_{max}$) of aripiprazole to the plasma concentration of aripiprazole 24 hours following administration ($C_{24}$) when administered to human or animal patients and prior to the administration of any further doses. The compositions of the invention typically exhibit a $C_{max}$ to $C_{24}$ ratio, preferably under steady state conditions, that is less than about 3:1, preferably less than about 2:1, more preferably less than about 1.5:1, such as from 1.1:1 to about 1.5:1 (e.g. about 1:1).

The compositions of the invention may exhibit one or more of the controlled release profiles defined above.

The compositions of the invention comprise a therapeutically effective amount of aripiprazole and at least one pharmaceutically acceptable excipient. In order to achieve one or more of the controlled release profiles described above, the therapeutically effective amount of aripiprazole may be formulated in numerous different ways, including, but not limited to diffusion-controlled formulations (such as wax matrices or pellets), dissolution-controlled formulations (such as press-coated formulations), dissolution/diffusion-controlled formulations, easily administrable formulations (such as chewable, fast dissolving, sprinkle or taste-masked formulations), enteric-coated formulations, osmotic pump technology formulations, tamper-resistant formulations, erosion-controlled formulations, ion exchange resins and combinations of the foregoing. The above formulations will be described in more detail below.

The formulations described herein for the compositions of the invention are designed primarily for oral administration. Suitable oral dosage forms include, but are not limited to capsules, tablets, liquids, powders, granules, suspensions, matrices, microspheres, seeds, pellets and/or beads of the foregoing formulations. Combinations of these dosage forms may also be used in the invention. For example, an oral dosage form containing aripiprazole may be in the form of microtablets enclosed inside a capsule, e.g. a hydroxypropylmethylcellulose (HPMC) capsule or a gelatin capsule. Any suitable gelatin capsule may be used, for example the hard gelatin capsule known as CAPSUGEL.

The solid oral dosage forms described above may typically utilize drug substance which may have an average particle size of greater than 100 nm, preferably greater than 500 nm, 1000 nm or 2000 nm (e.g. greater than 2500 nm).

The compositions of the invention may be diffusion controlled formulations. By the term "diffusion controlled formulations", we include formulations in which diffusion of dissolved aripiprazole from the formulation has a significant role in the rate of controlled release of aripiprazole from that formulation. However, dissolution processes may also be involved. Typical diffusion controlled formulations include so-called "reservoir systems", in which a core of aripiprazole is coated with a polymer (typically a water-insoluble polymer), and so-called "matrix systems", in which the aripiprazole is dispersed throughout a matrix (e.g. a swellable matrix), which may optionally be coated. In either system, flow and egress of the dissolved drug is controlled so as to achieve one or more of the release profiles defined above.

The compositions of the invention may be based on matrix technology. In this technology, aripiprazole is embedded in an excipient that makes a non-disintegrating core called a matrix. Diffusion of (dissolved) aripiprazole occurs through the core.

Preferably, the controlled release compositions of the invention are formulated so there is at least some time-delay before significant plasma concentrations of aripiprazole are achieved. In other words, the compositions of the invention may have a delayed and/or sustained and/or prolonged release component. Such compositions may avoid an initial burst of aripiprazole, or may be formulated so that release of aripiprazole in a particular part of the gastrointestinal tract (e.g. the stomach) is retarded. This may be useful for minimizing the adverse event profiles associated with aripiprazole.

Enteric coated formulations, which may protect the stomach against any irritant effects of aripiprazole, are also desirable. Such formulations can be coated with a composition that is non-toxic and includes a pharmaceutically acceptable enteric polymer, which is predominantly soluble in the intestinal fluid, but substantially insoluble in the gastric juices.

Typically, the compositions of the invention extend the aripiprazole release, e.g. by several hours, compared to aripiprazole release in the known immediate release dosage form.

The compositions of the invention may comprise a release-retarding material. The release-retarding material can be, for example, in the form of a matrix or a coating. The compositions of the invention may comprise, for example, a particle of aripiprazole that is combined with a release-retarding material. The release-retarding material is typically a material that permits release of aripiprazole at a sustained rate in an aqueous medium. The release-retarding material can be selectively chosen so as to achieve, in combination with the other stated properties, a desired release rate.

Release-retarding materials may be hydrophilic and/or hydrophobic polymers and/or materials. Suitable release-retarding materials include but are not limited to acrylic polymers, alkylcellulose, shellac, zein, hydrogenated vegetable oil, hydrogenated caster oil, and combinations comprising one or more of the foregoing materials. The compositions of the invention typically may contain between about 1% and about 80% (by weight) of the release-retarding material.

Suitable acrylic polymers include, for example, acrylic and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers.

Suitable alklylcelluloses include, for example, ethylcellulose. Those skilled in the art will appreciate that other cellulosic polymers, including other alkyl cellulosic polymers, can be substituted for part or all of the ethylcellulose.

Other suitable hydrophobic materials are typically water-insoluble and may have a melting point from about 30° C. to about 200° C., preferably from about 45° C. to about 90° C. The hydrophobic material may include neutral or synthetic waxes, fatty alcohols (such as lauryl, myristyl, stearyl, cetyl or preferably cetostearyl alcohol), fatty acids, including fatty acid esters, fatty acid glycerides (mono-, di-, and tri-glycerides), hydrogenated fats, hydrocarbons, hardened oils or fats (e.g. hardened rapeseed oil, caster oil, beef tallow, palm oil, soya bean oil) waxes, stearic acid, stearic acid, stearyl alcohol, polyethylene glycol, hydrophobic and hydrophilic materials having hydrocarbon backbones, and combinations comprising one or more of the foregoing materials.

Suitable waxes include beeswax, glycowax, castor wax, carnauba wax and wax-like substances, e.g. materials which are normally solid at room temperature and have a melting point of from about 30° C. to about 100° C., and combinations comprising two or more of the foregoing waxes.

The release-retarding material also may comprise digestible, long chain (e.g., $C_8$-$C_{50}$, preferably $C_{12}$-$C_{40}$), substituted or unsubstituted hydrocarbons, such as fatty acids, fatty alcohols, glyceryl esters of fatty acids, mineral and vegetable oils, waxes, and combinations comprising one or more of the foregoing materials. Hydrocarbons having a melting point of from about 25° C. to about 90° C. may be used. The compositions of the invention may contain up to about 60% by weight of at least one digestible, long chain hydrocarbon and/or up to 60% by weight of at least one polyalkylene glycol.

The release-retarding material also may comprise polylactic acid, polyglycolic acid, or a co-polymer of lactic acid and glycolic acid. The release-retarding material optionally includes other additives such as an erosion-promoting agent (e.g. starch and gums) and/or a semi-permeable polymer.

Release-modifying agents, which affect the release properties of the composition, may optionally be used in the compositions of the invention. The release-modifying agent may, for example, function as a pore-former. Typically, a pore-former creates channels which facilitate (e.g., accelerate) drug release. The pore former can be organic or inorganic, and may include materials that can be dissolved, extracted or leached from the coating in the environment of use. The pore-former can comprise one or more hydrophilic polymers, such as hydroxypropylmethylcellulose, lactose, metal stearates (e.g. alkali metal stearates such as magnesium stearate), polycarbonates (linear polyesters of carbonic acid in which carbonate groups reoccur in the polymer chain), and combinations comprising two or more of the foregoing release-modifying agents.

The release-retarding material can also include an exit means comprising at least one passageway, orifice, or the like. The passageway can have any shape, such as round, triangular, square or elliptical. Such exit means may be used in osmotic pump formulations, which are described in more detail herein.

In addition to the above ingredients, the compositions of the invention may also contain suitable quantities of other materials, e.g. diluents, lubricants, binders, granulating aids, colorants, flavorants and glidants that are conventional in the pharmaceutical art.

Examples of suitable lubricants include stearic acid, magnesium stearate, glyceryl behenate, talc, mineral oil (in PEG). Examples of suitable binders include water-soluble polymers, such as modified starch, gelatine, polyvinylpyrrolidone, polyvinyl alcohol, etc. Examples of suitable fillers include lactose, microcrystalline cellulose. An example of a glidant is silicon dioxide.

The compositions of the invention may include one or more substrates comprising aripiprazole. Such substrates may be coated with a sustained and/or delayed and/or prolonged release coating comprising a release-retarding material. Such compositions may be used in a multiparticulate system, such as beads, ion-exchange resin beads, spheroids, microspheres, seeds, pellets, matrices, granules, and other multiparticulate systems in order to obtain the desired controlled release of aripiprazole. The multiparticulate system can be presented in a capsule or other suitable unit dosage form, such as a tablet or a sachet.

In certain cases, more than one multiparticulate system may be used, each exhibiting different characteristics, such as pH dependence of release, time for release in various media (e.g. acid, base simulated intestinal fluid), release in vivo, size and composition.

In some cases, excipients to encourage spheronization may be used together with the active ingredient to form spheroids. Microcrystalline cellulose and hydrous lactose impalpable are examples of such spheronizing agents. Additionally (or alternatively), the spheroids may contain a water insoluble polymer, preferably an acrylic polymer, an acrylic copolymer, such as a methacrylic acid-ethyl acrylate copolymer, or ethyl cellulose. In such a formulation, any sustained release coating present may include a water insoluble material such as a wax, either alone or in admixture with a fatty alcohol, or shellac or zein.

Spheroids or beads, coated with an active ingredient may be prepared, for example, by dissolving the aripiprazole in water and then spraying the solution onto a substrate such as sugar spheres. Optionally, additional ingredients may be added prior to coating the beads in order to assist the active ingredient binding to the substrates, and/or to colour the solution, etc. The resulting substrate-active material may be overcoated with a barrier material, to separate the aripiprazole from the next coat of material, e.g. a release-retarding material. The barrier material may be a material comprising hydroxypropyl methylcellulose. However, any film-former known in the art may be used. Preferably, the barrier material increases stability during processing and/or shelf-life, without affecting the dissolution rate of the final product.

In order to achieve the desired release characteristics, aripiprazole may be coated with an amount of release-retarding material sufficient to obtain a weight gain level from about 1 to about 80% (e.g. from about 2 to about 40%), although more or less release-retarding material may be used depending, for example, on the desired release-rate. Moreover, there may be more than one release-retarding material used in the coating, as well as various other pharmaceutical excipients.

The release-retarding material may be in the form of a film coating comprising a dispersion of a hydrophobic polymer. Solvents typically used for application of the release-retarding coating include pharmaceutically acceptable solvents, such as water, alcohols (e.g. methanol or ethanol), methylene chloride, and combinations comprising one or more of the foregoing solvents.

The in vivo and/or in vitro release profile of the compositions of the invention may be altered, for example optimized, by using more than one release-retarding material, by varying the thickness of the release-retarding material, by changing the particular release-retarding material used, by altering the relative amounts of release-retarding material, by altering the manner in which any plasticizer present is added, by varying the amount of plasticizer relative to retardant material, by the inclusion of additional ingredients or excipients, by altering the method of manufacture, or by combinations of the foregoing.

In addition to or instead of being present in a matrix, the release-retarding agent can be in the form of coating. Optionally, a core can be coated, or a gelatine capsule can be further coated, with a sustained and/or delayed and/or prolonged release coating such as those described herein. The coatings may include a sufficient amount of a hydrophobic material to obtain increase the weight of the dosage from about 1 to about 80% (e.g. from about 2 to about 40%), although the coating can increase the weight of the dosage form by a larger percent depending on the desired release-rate, among other things.

The compositions of the invention preferably release aripiprazole slowly, e.g., when ingested and exposed to gastric fluids, and then to intestinal fluids. The controlled release profile of the formulations may be altered, for example, by varying the amount of release-retarding agent, e.g. hydrophobic material, by varying the amount any plasticizer present relative to hydrophobic material, by the inclusion of additional ingredients or excipients, by altering the method of manufacture, or combinations of the foregoing.

The compositions of the invention may be prepared in such a way that, substantially all of aripiprazole is present in amorphous form. The term "amorphous" is intended to mean consisting of disordered arrangements of molecules which do not possess a distinguishable crystal lattice. A typical process for forming a composition comprising amorphous aripiprazole comprises mixing aripiprazole with water and a pharmaceutically acceptable polymeric carrier and drying the mixture to form a composition comprising amorphous aripiprazole and the polymeric carrier.

Suitable pharmaceutically acceptable polymeric carriers include, for example, hydroxypropyl cellulose, methyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polypropylene, dextran, dextrins, hydroxypropyl-beta-cyclodextrin, chitosan, lactic/glycolid copolymers, polyorthoester, polyanhydrate, polyvinyl chloride, polyvinyl acetate, ethylene vinyl acetate, lectins, carbopols, silicon elastomers, polyacrylic polymers, maltodextrins, lactose, fructose, inositol, trehalose, maltose, raffinose, polyvinylpyrrolidone (PVP), polyethylene glycol (PEG), and alpha-, beta-, and gamma-cyclodextrins, and combinations of the foregoing carriers.

Preferred polymeric carriers are one or more of polyvinylpyrrolidone, hydroxypropylmetlyl cellulose, hydroxypropyl cellulose, methyl cellulose, block copolymers of ethylene oxide and propylene oxide, and polyethylene glycol. The polyvinylpyrrolidone (PVP) typically has an average molecular weight of from about 2,500 to about 3,000,000, for example from about 10,000 to about 450,000.

The polymeric carrier is preferably (i) miscible with both aripiprazole free base and its pharmaceutically acceptable salts (especially the hydrochloride salt), (ii) capable of keeping the salt in a homogeneous noncrystalline solid state dispersion after the water has been removed by evaporation, (iii) chemically inert with respect to aripiprazole and (iv) at least partially water soluble, and more preferably is fully water soluble.

Aripiprazole, the polymeric carrier, and water may be combined in any order. Typically, they are combined in a manner so as to form a solution of aripiprazole and the polymeric carrier. In forming a solution of the polymeric carrier and water, heating the solution is not generally necessary at lower concentrations but is preferred at higher concentrations, provided that the temperature does not result in decomposition or degradation of any materials. It is preferred to add aripiprazole after dissolving the polymeric carrier in water, suitably at from about 25 to about 100° C., for example from about 45 to about 80° C., in order to form a clear solution.

The ratio of aripiprazole to the polymeric carrier can be varied depending, for example, on the precise release profile required. Typical weight ratios of polymeric carrier to aripiprazole range from about 100:1 to about 0.5:1, preferably from about 50:1 to about 1:1, such as from about 20:1 to about 2:1 (e.g. about 5:1).

Upon formation of the (preferably clear) solution, the process proceeds by recovering the water to form a solid state dispersion of the aripiprazole in the polymeric carrier. Any method of removal of the water which provides a homogeneous solid state dispersion can be used, suitable methods including evaporation under vacuum or spray drying. Methods of evaporation under vacuum include rotary evaporation, static vacuum drying and the combination thereof. One skilled in the art of pharmaceutical formulations can readily determine a reasonable temperature at which water can be removed, provided the temperature is not so high as to cause degradation or decomposition of the materials. Typically, evaporation occurs at from about 25° C. to about 100° C. Evaporation of water should provide a solid state dispersion which is homogeneous and substantially free of water. By substantially free it is meant that the solid state dispersion typically contains less than 20% by weight of residual water, preferably less than 10%, more preferably less than 5%, most preferably less than 1%.

Any suitable pharmaceutically acceptable excipient can be added to the compositions of the invention. Examples of pharmaceutically acceptable excipients include diluents, aripiprazole vehicles, binders, disintegrants, glidants, sweeteners, compression aids, colouring agents, flavoring agents, suspending agents, dispersing agents, film formers, printing inks, lubricants and/or preservatives. These excipients may be used in a conventional manner, and alone or in any combination.

The pharmaceutical composition may be formulated by conventional methods of admixture such as blending, filling, granulation and compressing. Direct compression and wet granulation are two examples of methods which may be used to formulate the compositions of the invention. These and other methods are described and/or exemplified in more detail hereinafter.

Excipients may be added for numerous reasons, for example to facilitate manufacture, enhance stability, control release, enhance product characteristics, enhance bioavailability, enhance patient acceptability and combinations thereof.

Exemplary binders, which may be used to help to hold the dosage form together, include polyvinyl pyrrolidone, hydroxypropyl cellulose, hydroxypropyl methylcellulose, methylcellulose, hydroxyethyl cellulose, sugars, and combinations thereof. Disintegrants (such as croscarmellose sodium) expand when wet causing a tablet to break apart. Lubricants typically aid in the processing of powder materials. Exemplary lubricants include calcium stearate, glycerol behenate, magnesium stearate, mineral oil, polyethylene glycol, sodium stearylfumarate, stearic acid, talc, vegetable oil, zinc stearate, and combinations thereof. An example of a glidant is silicon dioxide.

The formulations described herein may contain a filler, such as a water insoluble or water soluble filler, or combinations thereof. Typical water insoluble fillers include silicon dioxide, titanium dioxide, talc, alumina, starch, kaolin, polacrilin potassium, powdered cellulose, microcrystalline cellulose, and combinations thereof. Typical water-soluble fillers include water soluble sugars and sugar alcohols, preferably lactose, glucose, fructose, sucrose, mannose, dextrose, galactose, the corresponding sugar alcohols and other sugar alcohols, such as mannitol, sorbitol, xylitol, and combinations thereof.

Aripiprazole and any optional additives may be prepared as subunits or as pellets, for example by a melt pelletization technique. In this technique, the aripiprazole in finely divided form is combined with a binder and other optional inert ingredients, and thereafter the mixture is pelletized, e.g. by mechanically working the mixture in a high shear mixer to form the pellets. By the term "pellets" we include pellets, granules, spheres and beads. Thereafter, the pellets can be sieved in order to obtain pellets of the requisite size.

The binder material may also be in particulate form and typically has a melting point above about 40° C. Suitable binder substances include hydrogenated castor oil, hydrogenated vegetable oil, other hydrogenated fats, fatty alcohols, fatty acid esters, fatty acid glycerides, and combinations thereof.

Oral dosage forms may be prepared to include an effective amount of subunits containing aripiprazole and optionally other active agents in the form of multiparticles or multipellets within a capsule. For example, a plurality of multiparticulates may be placed in a gelatin capsule in an amount sufficient to provide a release profile as defined above.

Subunits (e.g. in the form of multiparticulates) may be compressed into an oral tablet using conventional tableting equipment using standard techniques. The tablet formulation may include excipients such as, for example, an inert diluent (e.g. lactose) granulating and disintegrating agents (e.g. a cornstarch), binding agents (e.g. starch) and lubricating agents (e.g. magnesium stearate).

Alternatively, subunits containing aripiprazole and optionally containing additional active agents may be subjected to an extrusion process, the resulting extrudate then being shaped into tablets by methods known in the art. The diameter of the extruder aperture or exit port can be adjusted to vary the thickness of the extruded strands. Furthermore, the exit part of the extruder may have any suitable shape, for example round, oblong or rectangular. The exiting strands can be reduced to particles using any suitable method, for example with a hot wire cutter or a guillotine.

A melt-extruded multiparticulate system can be, for example, in the form of granules, spheroids, pellets, or the like, depending upon the extruder exit orifice. The terms "melt-extruded multiparticulate(s)" and "melt-extruded multiparticulate system(s)" and "melt-extruded particles" are used interchangeably herein and typically include a plurality of subunits, preferably of similar size and/or shape. The melt-extruded multiparticulates are typically from about 0.1 to about 12 mm in length and from about 0.1 to about 5 mm in diameter. In addition, the melt-extruded multiparticulates can be any geometrical shape within this size range. Alternatively, the extrudate can simply be cut into desired lengths and divided into unit doses of aripiprazole without the need of a pelletization step.

Many of the oral dosage forms described herein contain aripiprazole and optionally additional active agents in the form of particles. Such particles may be compressed into a tablet, present in a core element of a coated dosage form, such as a taste masked dosage form, a press coated dosage form, or an enteric coated dosage form, or may be contained in a capsule, osmotic pump dosage form, or other dosage form.

For particles (e.g. powder particles) present in the core element of a coated dosage form, the particles may have a particle size of from about 1 μm to about 250 μm, preferably from about 25 μm to about 200 μm, more preferably from about 35 μm to about 150 μm. The core element typically has a particle size distribution with a median of about 100 μm.

Another parameter to consider is the shape of the particles and/or any core element. For example, particle/core shape can influence the coverage and stability of any coating that may be used. Both the crystallinity of aripiprazole and the aspect ratio of the particles are related to particle/core shape. If the aripiprazole of the coated dosage has a crystalline morphology, sharp angles on the crystal can cause weaknesses (e.g. stress points) in the coat possibly leading to premature release of aripiprazole from the dosage form. Furthermore, areas of thin coating are susceptible to breaking and cracking and hence less effective for sustained release and taste masking. This potential problem may be offset somewhat by the particles/core having a relatively low aspect ratio. The aspect ratio is a measure of the length to breadth. For example, a low aspect ratio of about 1 would be a box or sphere. Crystals with a high aspect ratio are more pointed with needle-like crystals. Crystals with a high aspect ratio may result in a relatively thin coat at the crystal needle tips leading to a more rapid release rate of aripiprazole than is preferred. A low aspect ratio spherical shape of the particle is advantageous for both solubility of the coat and to increase the chance of all the aripiprazole contained in the formulation being released. Therefore, it is most preferable that the aspect ratio is less than about 3, more preferably less than about 2, and most preferably approximately 1 providing a substantially rounded shape. This may be achieved, for example, by spheronization.

Inconsistencies in size and shape can lead to inconsistent coating. Where the particles containing aripiprazole are of different size and shape, polymeric coating materials such as ethyl cellulose may deposit differently on each particle. Therefore it is preferable for coated dosage forms that most if not all particles of the dosage form have substantially the same size and shape so that the coating process is better controlled and maintained.

The compositions described herein may be coated with a coating material. The coating typically comprises from about 0 to about 90% by weight of the composition. The coating material typically includes a polymer, preferably a film-forming polymer, for example, methyl cellulose, ethyl cellulose, hydroxypropyl cellulose, hydroxypropyl methyl cellulose, hydroxybutyl methyl cellulose, cellulose acetate, cellulose propionate, cellulose acetate propionate, cellulose acetate butyrate, cellulose acetate phthalate, carboxymethyl cellulose, cellulose triacetate, cellulose sulphate sodium salt, poly (methyl methacrylate), poly(ethyl methacrylate), poly(butyl methacrylate), poly(isobutyl methacrylate), poly(hexyl methacrylate), poly(phenyl methacrylate), poly(methyl acrylate), poly(isopropyl acrylate), poly(isobutyl acrylate), poly (octadecyl acrylate), high or low density, polyethylene, polypropylene, poly(ethyleneglycol), poly(ethylene oxide), poly(ethylene terephthalate), poly(vinyl alcohol), poly(vinyl isobutyl ether), poly(vinyl acetate), poly(vinyl chloride), polyvinyl pyrrolidone, and combinations thereof.

The coating material may be water soluble or water insoluble. For certain application such a taste-masking, it is preferable to use a water insoluble polymer. Suitable water insoluble polymers include ethyl cellulose or dispersions of ethyl cellulose, acrylic and/or methacrylic ester polymers, cellulose acetates, butyrates or propionates or copolymers of acrylates or methacrylates having a low quaternary ammonium content, and combinations of the foregoing polymers.

Preferred hydrophobic or water insoluble polymers for use in the compositions of the invention include, for example, methacrylic acid esters, ethyl cellulose, cellulose acetate, polyvinyl alcohol-maleic anhydride copolymers, β-pinene polymers, glyceryl esters of wood resins, and combinations of the foregoing.

The coating may also include one or more monomeric materials such as sugars (e.g. lactose, sucrose, fructose and mannitol), salts (e.g. sodium chloride and potassium chloride) and organic acids (e.g. fumaric acid, succinic acid, tartaric acid and lactic acid). The coating may also include a filler such as described earlier herein.

The coating composition may include additives which improve the physical properties of the coating film. For example, the coating composition may comprise a plasticizer. For example, because ethyl cellulose has a relatively high glass transition temperature and does not form flexible films under normal coating conditions, it may be advantageous to add plasticizer to the ethyl cellulose before using it as a coating material. Generally, the amount of plasticizer included in a coating solution is based on the concentration of the polymer, typically ranging from 0 to about 50% by weight of the coating composition. Suitable concentrations of the plasticizer may be determined by routine experimentation.

Examples of plasticizers for ethyl cellulose and other celluloses include plasticizers such as dibutyl sebacate, diethyl phthalate, triethyl citrate, tributyl citrate, triacetin, acetylated monoglycerides, phthalate esters, castor oil, and combinations thereof.

Examples of plasticizers for acrylic polymers include citric acid esters such as triethyl citrate 21, tributyl citrate, dibutyl phthalate, 1,2-propylene glycol, polyethylene glycols, propylene glycol, diethyl phthalate, castor oil, triacetin, acetylated monoglycerides, phthalate esters, castor oil, and combinations thereof.

A typical coating comprises (a) a poorly water-permeable component such as an alkyl cellulose (e.g. ethylcellulose) such as AQUACOAT (a 30% solution) or SURELEASE (a 25% solution) and (b) a water-soluble component, e.g. an agent that can form channels through the poorly water-permeable component upon the hydration or dissolution of the soluble component.

Preferably, the water-soluble component (b) is a low molecular weight, polymeric material, e.g. hydroxyalkylcellulose, hydroxyallyl(alkylcellulose), carboxymethylcellulose, or salts thereof. Particular examples of these water soluble polymeric materials include hydroxyethylcellulose, hydroxypropylcellulose, hydroxyethylmethylcellulose, hydroxypropylmethyl cellulose (e.g. METHOCEL), carboxymethylcellulose, sodium carboxymethyl cellulose, and combinations thereof. The water-soluble component (b) is preferably of relatively low molecular weight, preferably less than about 25,000, preferably less about 21,000.

In the coating, the weight ratio of the water soluble component (b) to the poorly water permeable portion (a) is typically from about 1:4 to about 2:1, such as from about 1:2 to about 1:1, for example about 2:3. The coating typically constitutes from about 1 to about 90% by weight, such as from about 2% to about 50%, for example from about 5 to about 30%, of the weight of the total composition.

Preferably, the coating may be a substantially continuous coat and substantially hole-free. This is particularly advantageous, for example, where the coating provides taste masking. The phrase "substantially continuous coating" is meant to include a coating, which retains a smooth and continuous appearance when magnified 1000 times under a scanning electron microscope and wherein no holes or breakage of the coating are evident. Typically, the coating is from about 0.005 to about 25 μm thick, preferably from about 0.05 to about 5 μm.

One or more of the coatings described herein may be used in the compositions of the subject invention. If two or more coatings are present, the coating material used for each coating may be the same or different.

Any suitable method may be used to apply the coating. Processes which may be used include simple or complex coacervation, interfacial polymerization, liquid drying, thermal and/or ionic gelation, spray drying, spray chilling, fluidized bed coating, pan coating and electrostatic deposition. A substantially continuous coating may be achieved, for example, by spray drying from a suspension or dispersion of aripiprazole in a solution of the coating composition including a polymer in a solvent in a drying gas having a low dew point.

When a solvent is used to apply the coating, the solvent is preferably an organic solvent which is good solvent for the coating material and a poor solvent for aripiprazole. While aripiprazole may partially dissolve in the solvent, it is preferred that the active ingredient will precipitate out of the solvent during the spray drying process more rapidly than the coating material. The solvent may be selected from alcohols such as methanol, ethanol, halogenated hydrocarbons such as dichloromethane (methylene chloride), hydrocarbons such as cyclohexane, and combinations thereof.

The concentration of polymer in the solvent will normally be less than about 75% by weight, typically from about 10 to about 30% by weight. After coating, the coated dosage forms are typically allowed to cure for from about 1 to about 2 hours at a temperature of from about 50° C. to about 60° C.

The dosage form (e.g. a tablet) can be prepared by various conventional mixing, comminution and fabrication techniques readily apparent to those skilled in the chemistry of drug formulations. Examples of such techniques are direct compression (using appropriate punches and dies fitted to a suitable rotary tableting press), injection or compression molding using suitable molds fitted to a compression unit, granulation followed by compression, and extrusion into a mold or to an extrudate to be cut into lengths.

When particles or tablets are made by direct compression, the addition of lubricants to the particles/tablets may be helpful and sometimes important to promote powder flow and to prevent capping of the particle (breaking off of a portion of the particle) when the pressure is relieved. Any of the lubricants previously described herein may be used. Preferred lubricants include magnesium stearate and/or sodium stearyl fumarate (typically in a concentration of from about 0.1 to about 10%, e.g. from about 0.25 to about 3% by weight in the powder mix), and hydrogenated vegetable oil, for example hydrogenated and refined triglycerides of stearic and palmitic acids may be used at from about 1 to about 5% by weight in the powder mix. Additional excipients may be added to enhance powder flowability and reduce adherence. Compositions of the invention made by direct compression are described in more detail in the Examples.

Oral dosage forms may be prepared by including an effective amount of melt-extruded subunits in the form of multiparticles within a capsule. For example, a plurality of the melt-extruded multiparticulates can be placed in a gelatin capsule in an amount sufficient to provide the desired release profile when administered orally. Alternatively, the composition may be in the form of microtablets enclosed inside a gelatin capsule. Microtablets typically have a size of from 0.5 to 7 mm in their largest dimension, such as from 1 to 6 mm, for example 3 to 4 mm.

A number of formulations are described below as having preferred components. It is to be understood that any of the components described as being used in one type of formulation may also be used in another type of formulation, even though such components may not be listed as being used in the other formulation. Moreover, the formulations described below may also contain any of the excipients described above, or indeed any of the excipients known in the art.

The compositions of the invention may be in the form of a wax formulation. A wax formulation is a solid dosage form comprising the aripiprazole in a waxy matrix.

The wax material used in the composition of the invention may be, for example, an amorphous wax, an anionic wax, an anionic emulsifying wax, a bleached wax, a carnauba wax, a cetyl ester wax, a beeswax, a castor wax, an emulsifying wax such as a cationic emulsifying wax, a cetrimide emulsifying wax, or a nonionic emulsifying wax, a glycerol behenate, a microcrystalline wax, a nonionic wax, a paraffin, a petroleum wax, a spermaceti wax, a white wax, and combinations of one or more of the foregoing waxes.

A cetyl ester wax suitable for use in the invention typically has a molecular weight of from about 470 to about 490, and is a mixture containing primarily esters of saturated fatty alcohols and saturated fatty acids. A wax matrix suitable for use in the compositions of the invention contains carnauba wax and no other waxy material. Another suitable wax matrix includes carnauba wax and glycerol behenates. The wax matrices suitable for use in the invention may be used with or without a coating.

The wax material may be used in the range of from about 30 to about 95%, preferably from about 40 to about 85%, more preferably from about 45 to about 80%, most preferably about 50% to about 75% by weight of the total weight of the matrix material. The remainder of the matrix material is typically aripiprazole, although other optional components (e.g. fatty acid soaps, see below) may also be present. When a combination of waxes is used, the component waxes can be used in any suitable ratio. For example, if a combination of carnauba wax and glyceryl behenate is used, the relative amounts of each wax typically is from about 99 to 60 parts carnauba wax (for example from 99 to about 85 parts) and from about 1 to about 40 parts glyceryl behenate (for example from 1 to about 15 parts). In formulations that have a combination of carnauba wax and castor wax, the relative amounts of each wax typically is from about 99 to 60 parts carnauba wax (for example from 99 to about 85 parts) and from about 1 to about 40 parts castor wax (for example from 1 to about 15 parts). When carnauba wax, glyceryl behenate, and castor wax are present, the carnauba wax typically comprises at least about 85% of the waxy material present, the balance being made up of a combination of glyceryl behenate and castor wax.

Fatty acids and fatty acid soaps may be present in the waxy dosage form. In some cases, the fatty acids and/or fatty acid soaps can replace a portion of the wax material. These optional fatty acids and fatty acid soaps can be those that are generally used in the pharmaceutical industry as tableting lubricants. Such fatty acids and fatty acid soaps include solid fatty acids (for example fatty acids having from about 16 to about 22 carbon atoms), the alkaline earth metal salts thereof, (particularly the magnesium and calcium salts) and combinations of the foregoing. For example, the fatty acid can be stearic acid. The optional fatty acids and fatty soaps, when present, are typically used in amounts up to about 10% of the total weight of the matrix material, such as from about 1 to about 9%, for example from about 2 to about 8% or from about 3 to about 6% of the total weight of the matrix material.

To prepare the wax formulation, the wax or waxes may be melted and used to granulate aripiprazole using melt granulation techniques. The granulate may be allowed to cool and then be milled to a proper size. Advantageously, the granulate is milled to an average particle size of about 75 microns to about 850 microns, preferably about 150 microns to about 425 microns. The milled granulate may be mixed with optional processing aids. The processing aids include, for example, hydrophobic colloidal silicon dioxide. Hydrophobic silicon dioxide may typically be used in amounts of less than or equal to about 0.5% by weight of the matrix material, but individual formulations can be varied as required. The blend of the waxy granulate and the processing aids, if any, may be compressed and then optionally coated.

The wax formulation may be formulated into any suitable dosage form, for example, coated (e.g. with a functional coating composition or a non-function related coating composition) or uncoated tablets, compressed pellets contained in capsules, or loose powder or powder filled capsules.

When the coating composition is a functional coating composition, it typically comprises a water insoluble component and a water soluble component. When the coating composition is a non-functional coating composition, it typically comprises a water soluble component, preferably in the absence of a water insoluble component. The coating composition may comprise pharmaceutically acceptable dyes, pigments, or mixtures thereof.

As described above, the compositions of the invention may comprise one or more active agents in addition to aripiprazole. Therefore, the wax formulation may also include an active agent in addition to aripiprazole in the matrix.

The wax formulations described herein may be made by hot melting a waxy material to form a melt and granulating aripiprazole with the melt to form a granulate. The granulate is typically then milled and compressed to form a matrix. The method may further comprise blending the granulate with a processing aid prior to compressing the granulate to form the matrix. The method may further comprise coating the matrix with a functional and/or a non-functional coating.

The compositions of the invention may be in the form of press-coat formulations. Such formulations comprise a core composition containing aripiprazole with a coating composition press-coated on the core. The core composition typically comprises a waxy material containing aripiprazole. The coating composition typically comprises a hydrophilic polymer and optionally aripiprazole.

The waxy material of the core composition is typically a hydrophobic waxy material capable of providing controlled release of aripiprazole. Such waxy materials may be, for example, carnauba wax, tribehenin, fatty alcohols particularly those having 12-24 carbon atoms, such as lauryl alcohol, myristyl alcohol, stearyl alcohol, palmityl alcohol, etc.), fatty acids (particularly those having 12-24 carbon atoms, such as lauric acid, myristic acid, stearic acid, palmitic acid, etc), polyethylenes, castor wax, $C_{16-30}$ fatty acid triglycerides, beeswax, and combinations of one or more of the foregoing waxes.

The hydrophilic polymer of the coating composition is typically chosen so as to aid controlled release of aripiprazole. An example of such a hydrophilic polymer is a film-forming polymer, such as a hydrophilic cellulose polymer, in particular a hydroxyalkyl cellulose polymer. Examples of such hydroxyalkyl cellulose polymers include hydroxyethylcellulose (HEC), hydroxypropylcellulose (HPC), hydroxypropylmethylcellulose (HMPC), hydroxypropylethylcellulose (HPEC), hydroxypropylpropylcellulose (HPPC), hydroxypropylbutylcellulose (HPBC), and combinations of one or more of the foregoing polymers.

Both the core composition and the coating composition may independently include a filler, such as a water soluble or insoluble filler, or a mixture thereof. Examples of water insoluble fillers include talc and calcium salts such as a calcium phosphate, e.g. a dicalcium phosphate. If there is a filler in the coating composition, it can be the same or different as the filler in the core composition, if any. For example, the core composition may include a water-soluble filler while the coating composition may include a water-insoluble filler.

Optional excipients can also be present in the core composition and/or the coating composition. Such excipients include lubricants (such as talc and magnesium stearate), glidants (such as famed or colloidal silica), pH modifiers (such as acids, bases and buffer systems), pharmaceutically useful processing aids, and combinations of one or more of the foregoing excipients. Excipients in the compositions can be the same or different as those in the core compositions.

In order to form the press-coat formulations, the core composition components (aripiprazole, waxy material, and optional excipients) are typically blended together and compressed into suitable cores. The blending can take place in a suitable order of addition. The cores may be blended by starting with the smallest volume component and then successively adding the larger volume components. An alternative process is to melt the wax and to blend aripiprazole and optional excipients into the melted wax. Alternatively, aripiprazole, wax and any optional excipients can be blended together and then subjected to a temperature at which the wax will melt. Once cooled, the solidified mass can be milled into granules for compaction into cores.

Typically, the core composition is press-coated with the coating composition to form a tablet. The tablet may be further coated with optional additional coatings. The additional coatings can be pH-dependent or pH-independent, aesthetic or functional, and can contain aripiprazole or a different active agent.

If aripiprazole is present in the coating composition, the molar ratio of aripiprazole in the core composition to aripiprazole in the coating composition is from about 500:1 to about 1:10, such as from about 100:1 to about 1:5, e.g. from about 10:1 to about 1:1.

A preferred press-coat formulation comprises a core composition comprising aripiprazole coated with a coating composition comprising hydroxypropylmethyl cellulose (HPMC). The core composition optionally comprises one or more waxy materials, e.g. carnauba wax and the coating composition optionally comprises aripiprazole. Such press coat formulations may be prepared by press-coating the coating composition onto the core composition.

The compositions of the invention may be formulated using osmotic pump technology. Osmotic pump technology uses osmotic pressure to deliver aripiprazole at a controlled rate. Osmotic pump dosage formulations typically include a semi-permeable membrane surrounding a core that contains at least two components, one component comprising aripiprazole, the other comprising an osmotic push layer (an osmotically active expandable driving member), such as an osmotically active polymer. After the dosage form is swallowed, water enters the membrane at a rate primarily determined by the nature of the membrane. This causes the push layer to swell, releasing aripiprazole at a controlled rate through an exit means comprising a passageway or orifice (e.g. a laser-drilled hole) by the action of the osmotically active driving member.

The osmotic pump formulation typically comprises a semipermeable membrane, for example a capsule or tablet or other dosage form typically having an outer wall comprising a selectively semipermeable material. The selectively permeable material preferably has the following characteristics: (i) it does not adversely affect a host or animal, (ii) it is permeable to the passage of an external aqueous fluid, such as water or biological fluids while remaining essentially impermeable to the passage of aripiprazole, (iii) it is substantially insoluble in body fluids, (iv) it is non-toxic, and (v) it is non-erodible in the environments to which it is subjected.

Representative materials for forming the selectively semipermeable wall include semipermeable homopolymers and copolymers. Suitable materials include, for example, cellulose esters, cellulose monoesters, cellulose diesters, cellulose triesters, cellulose ethers, cellulose ester-ethers, and combinations thereof. These cellulosic polymers have a degree of substitution (DS) on their anhydroglucose unit from greater than 0 to about 3. The "degree of substitution" is the average number of hydroxyl groups originally present on the anhydroglucose unit that have been replaced by a substituting group, or converted into another group. The anhydroglucose unit can be partially or completely substituted with semipermeable polymer forming groups such as acyl, alkanoyl, aroyl, alkenyl, alkoxy, halogen, carboalkyl, allylcarbamate, alkylcarbonate, alkylsulfonate and alkylsulfamate.

Other selectively semipermeable materials include, for example, cellulose acylate, cellulose diacylate, cellulose triacylate, cellulose acetate, cellulose diacetate, cellulose triacetate, mono-, di- and tri-cellulose alkanylates, mono-, di- and tri-alkenylates, mono-, di- and tri-aroylates, and combinations of the foregoing materials. Exemplary polymers include cellulose acetate having a DS of 1.8 to 2.3 and an acetyl content of about 32 to about 40%, cellulose diacetate having a DS of 1 to 2 and acetyl content of about 21 to about 35%, cellulose triacetate having a DS of 2 to 3 and an acetyl content of about 34 to about 45%. Other examples of cellulosic polymers include cellulose propionate having a DS of 1.8 and a propionyl content of about 38.5%, cellulose acetate propionate having an acetyl content of about 1.5 to about 7% and a propionyl content of about 39 to about 42%, cellulose acetate propionate having an acetyl content of about 2.5% to about 3%, an average propionyl content of about 39 to about 45% and a hydroxyl content of about 2.8% to about 5.4%. Still farther exemplary cellulosic polymers include cellulose acetate butyrate having a DS of 1.8, an acetyl content of about 13 to about 15% and a butyryl content of about 34% to about 39%, cellulose acetate butyrate having an acetyl content of about 2 to about 29.5%, a butyryl content of about 17 to about 53%, and a hydroxyl content of about 0.5% to about 4.7%. Yet further examples of suitable cellulosic polymers include cellulose triacylates have a DS of 2.9 to 3 such as cellulose trivalerate, cellulose trilaurate, cellulose tripalmitate, cellulose trioctanoate, and cellulose tripropionate, cellulose diesters having a DS of 2.2 to 2.6 such as cellulose disuccinate, cellulose dipalmitate, cellulose dioctanoate, cellulose dicarpylate, mixed cellulose esters such as cellulose acetate valerate, cellulose acetate succinate, cellulose propionate succinate, cellulose acetate octanoate, cellulose valerate palmitate, cellulose acetate heptonate, and combinations of the foregoing cellulosic polymers polymers.

Other potentially suitable semipermeable polymers include, for example, acetaldehyde dimethyl cellulose acetate, cellulose acetate ethylcarbamate, cellulose acetate methylcarbamate, cellulose dimethylaminoacetate, semipermeable polyamides, semipermeable polyurethanes, semipermeable polysulfanes, semipermeable sulfonated polystyrenes, cross-linked selectively semipermeable polymers formed by the coprecipitation of a polyanion and a polycation, semipermeable silicon rubbers, semipermeable polystyrene derivatives, semipermeable poly(sodium styrene-sulfonate), semipermeable poly(vinylbenzyltrimethyl) ammonium chloride polymers, and combinations comprising of the foregoing polymers, including combinations with one or more of the selectively permeable materials listed in the preceding paragraph.

The osmotically expandable driving member (or osmotic push layer) of the osmotic pump dosage form is typically a swellable and expandable inner layer. The materials suitable for forming the osmotic push layer, include polymeric materials and/or polymeric materials blended with osmotic agents, both of which typically interact with water or a biological fluid, absorb the fluid, and swell or expand to an equilibrium state in the presence of the fluid without dissolving. Preferably, the polymer should exhibit the ability to retain a significant fraction of absorbed fluid in the polymer molecular structure. Such polymers may be gel polymers that can swell or expand to a very high degree, for example exhibiting from about 2 to about 50-fold volume increase.

Suitable swellable, hydrophilic polymers, also known as osmopolymers, can be non-cross-linked or lightly cross-linked. The cross-links can be covalent or ionic bonds with the polymer. The polymer may be of plant, animal or synthetic origin. Polymeric materials useful for the present purpose include poly(hydroxyalkyl methacrylate) having a molecular weight of from about 5,000 to about 5,000,000, poly(vinylpyrrolidone) having a molecular weight of from about 10,000 to about 360,000, anionic and cationic hydrogels, poly(electrolyte) complexes, poly(vinyl alcohol) having a low acetate residual, a swellable mixture of agar and carboxymethyl cellulose, a swellable composition comprising methyl cellulose mixed with a sparingly crosslinked agar, a water-swellable copolymer produced by a dispersion of finely divided copolymer of maleic anhydride with styrene, ethylene, propylene, or isobutylene, water swellable polymers of N-vinyl lactams, and combinations of the foregoing polymers.

Other gelable, fluid absorbing and retaining polymers useful for forming the osmotic push layer include pectins having a molecular weight ranging from about 30,000 to about 300,000, polysaccharides such as agar, acacia, karaya, tragacanth, algins and guar, poly (carboxylic acids) and their salt derivatives, polyacrylamides, water-swellable indene maleic anhydridge polymers, polyacrylic acid having a molecular weight of from about 80,000 to about 200,000, polyethylene oxide polymers having a molecular weight of from about 100,000 to about 5,000,000 (but may be higher), starch graft copolymers, polyanion and polycation exchange polymers, starch-polyacrylonitrile copolymers, acrylate polymers with water absorbability of from about 100 to about 600 times their original weight, diesters of polyglucan, a mixture of cross-linked polyvinyl alcohol and poly(N-vinyl-2-pyrrolidone), zein (available as prolamine), poly(ethylene glycol) having a molecular weight of from about 4,000 to about 100,000, and combinations of the foregoing polymers.

The osmotically expandable driving layer of the osmotic pump dosage form may further contain an osmotically effective compound (osmagent) that can be used neat or blended homogeneously or heterogeneously with the swellable polymer discussed above. Such osmagents are typically osmotically effective solutes that are soluble in the fluid absorbed into the swellable polymer, and exhibit an osmotic pressure gradient across the semipermeable wall against an exterior fluid.

Suitable osmagents include, for example, solid compounds such as magnesium sulfate, magnesium chloride, sodium chloride, lithium chloride, potassium sulfate, sodium sulfate, mannitol, urea, sorbital, inositol, sucrose, glucose, and combinations thereof. The osmotic pressure of the osmagents is typically from about 0 to about 500 atm, but may be higher.

The swellable, expandable polymer of the osmotically expandable driving layer, in addition to providing a driving source for delivering aripiprazole from the dosage form, may also function as a supporting matrix for an osmotically effective compound (or osmagent). The osmotic compound may be homogeneously or heterogeneously blended with the polymer to yield the desired expandable wall or expandable pocket. A typical osmotic pump dosage form may comprise from about 20 to about 90% by weight of polymer and from about 80 to about 10% by weight of osmotic compound, preferably from about 35 to about 75% by weight of polymer and from about 65 to about 25% by weight of osmotic compound based on the total weight of the formulation.

The aripiprazole in the osmotic pump dosage form may be formulated in any suitable manner, for example as a thermo-responsive formulation in which aripiprazole is dispersed in a thermo-responsive composition. Alternatively, the osmotic pump dosage form may contain a thermo-responsive element comprising a thermo-responsive composition at the interface of the osmotic push layer and aripiprazole composition. Representative thermo-responsive compositions (including their melting points in parentheses) are cocoa butter (32° C.-34° C.), cocoa butter and 2% beeswax (35° C.-37° C.), propylene glycol monostearate and distearate (32° C.-35° C.), hydrogenated oils such as hydrogenated vegetable oil (36° C.-37.5°), 80% hydrogenated vegetable oil and 20% sorbitan monopalmitate (39° C.-39.5° C.), 80% hydrogenated vegetable oil and 20% polysorbate 60, (36° C.-37° C.), 77.5% hydrogenated vegetable oil, 20% sorbitan trioleate, 2.5% beeswax and 5.0% distilled water, (37° C.-38° C.), mono-di, and triglycerides of acids having from 8-22 carbon atoms including saturated and unsaturated acids such as palmitic, stearic, oleic, lineolic and archidonic; triglycerides of saturated fatty acids with mono- and diglycerdies (34° C.-35.5° C.), propylene glycol mono- and distearates (33° C.-34° C.), partially hydrogenated cottonseed oil (35° C.-39° C.), block copolymers of polyoxyalkylene and propylene glycol, block copolymers of 1,2-butylene oxide and ethylene oxide, block copolymers of propylene oxide and ethylene oxide, hardened fatty alcohols and fats (33° C.-36° C.), hexadienol and hydrous lanolin triethanolamine glyceryl monostearate (38° C.), eutectic mixtures of mono-, di-, and triglycerides (35° C.-39° C.), WITEPSOL#15, triglyceride of saturated vegetable fatty acid with monoglycerides (33.5° C.-35.5° C.), WITEPSOL H32 free of hydroxyl groups (31° C.-33° C.), WITEPSOL W25 having a saponification value of 225-240 (33.5° C.-35.5° C.), WITEPSOL E75 having a saponification value of 220-230 (37° C.-39° C.), a polyalkylene glycol such as polyethylene glycol 1000, a linear polymer of ethylene oxide (38° C.-41° C.), polyethylene glycol 1500 (38° C.-41° C.), polyethylene glycol monostearate (39° C.-42.5° C.), 33% polyethylene glycol 1500, 47% polyethylene glycol 6000 and 20% distilled water (39° C.-41° C.), 30% polyethylene glycol 1500, 40% polyethylene glycol 4000 and 30% polyethylene glycol 400, (33° C.-38° C.), mixtures of mono-, di- and triglycerides of saturated fatty acids having 11 to 17 carbon atoms, (33° C.-35° C.), and mixtures of the foregoing.

The thermo-responsive compositions, including thermo-responsive carriers, are thought to be useful for storing aripiprazole in a solid composition at a temperature of about 20° C. to about 33° C., maintaining an immiscible boundary at the swelling composition interface, and for dispensing the agent in a flowable composition at a temperature greater than about 33° C. and preferably from about 33° C. to about 40° C.

When the aripiprazole containing thermo-responsive formulations described above are used, the integrity of the semi-permeable membrane which is also present in such osmotic pump formulations is preferably not compromised (e.g. melted or eroded) by the presence of the thermo-responsive formulations.

Aripiprazole in the osmotic pump dosage form may be formulated by any suitable techniques known in the art, for example by wet granulation or fluid bed granulation, as described in more detail below.

Firstly, aripiprazole and the ingredients comprising the aripiprazole layer are blended using an organic solvent, such as isopropyl alcohol-ethylene dichloride 80:20 v/v (volume:volume) as the granulation fluid. Other granulating fluid such as denatured alcohol 100% may be used for this purpose. The ingredients forming the aripiprazole layer are individually passed through a screen such as a 40-mesh screen and then thoroughly blended in a mixer. Next, other ingredients comprising the aripiprazole layer are dissolved in a portion of the granulation fluid. Then the latter prepared wet blend is slowly added to the aripiprazole blend with continual mixing in the blender. The granulating fluid is added until a wet blend is produced, which wet mass then is forced through a screen such as a 20-mesh screen and onto oven trays. The blend is dried for about 18 to about 24 hours at about 30° C. to about 50° C. The dry granules are sized then with a screen such as a 20-mesh screen. Next, a lubricant is passed through a screen such as an 80-mesh screen and added to the dry granule blend. The mixture is put into milling jars and mixed on a jar mill for about 1 to about 15 minutes. The push layer may also be made by the same wet granulation techniques. The compositions are pressed into their individual layers in a KILIAN press-layer press.

Another manufacturing process that can be used for providing the aripiprazole layer and the osmotically expandable driving layer comprises blending the powered ingredients for each layer independently in a fluid bed granulator. After the powered ingredients are dry blended in the granulator, a granulating fluid (e.g. poly(vinyl-pyrrolidone) in water, denatured alcohol, 95:5 ethyl alcohol/water, or blends of ethanol and water) is sprayed onto the powders. Optionally, the ingredients can be dissolved or suspended in the granulating fluid. The coated powders are then typically dried in a granulator. This process granulates the ingredients present therein while adding the granulating fluid. After the granules are dried, a lubricant such as stearic acid or magnesium stearate is added to the granulator. The granules for each separate layer may then be pressed in the manner described above for the wet granulation method.

The osmotic push aripiprazole formulation and osmotic push layer of the osmotic push dosage form may also be manufactured by mixing aripiprazole with composition forming ingredients and pressing the composition into a solid lamina. In a further alternative method of manufacture, aripiprazole, any other composition-forming ingredients and a solvent are typically mixed into a solid, or a semisolid, by methods such as ballmilling, calendaring, stirring or rollmilling, and then pressed into a preselected layer forming shape. Next, a layer of composition comprising an osmopolymer and an optional osmagent are typically placed in contact with the layer comprising aripiprazole. The layering of the first layer comprising aripiprazole and the second layer comprising the osmopolymer and optional osmagent composition may be accomplished by using a conventional layer press technique.

The semipermeable wall can be applied by molding, spraying or dipping the pressed bilayer's shapes into wall forming materials. An air suspension coating procedure which includes suspending and tumbling the two layers in a current of air until the wall forming composition surrounds the layers may also be used to form the semi-permeable wall of the osmotic formulations.

The dispenser of the osmotic pump dosage form may be, for example, in the form of a hard or soft capsule. The capsule may also be osmotic.

The hard capsule may be composed of two parts, a cap and a body, which are typically fitted together after the body (which is generally larger than the cap) is filled with aripiprazole. The hard capsule may be fitted together by slipping or telescoping the cap section over the body section, thus completely surrounding and encapsulating aripiprazole.

The soft capsule of the osmotic pump dosage form may be a one-piece soft capsule. Typically, the soft capsule comprises a sealed construction encapsulating aripiprazole. The capsule may be made by various processes, such as the plate process, the rotary die process, the reciprocating die process, and the continuous process.

Materials useful for forming the capsule of the osmotic pump dosage form may be commercially available materials including gelatin (typically having a viscosity of about 5 to about 30 millipoises and a bloom strength up to about 150 grams or gelatin having a bloom value of about 150 to about 250), a composition comprising gelatin, glycerine, water and titanium dioxide, a composition comprising gelatin, erythrosine, iron oxide and titanium dioxide, a composition comprising gelatin, glycerine, sorbitol, potassium sorbate and titanium dioxide, a composition comprising gelatin, acacia, glycerine, and water and combinations thereof. Commercially available gelatin capsules (e.g. CAPSUGEL) may also be used.

The semipermeable wall forming composition may be applied to the aripiprazole containing component and/or to the exterior surface of the capsule in laminar arrangement by molding, forming, air spraying, dipping or brushing. Alternative techniques that can be used for applying the semipermeable wall include air suspension procedures and pan coating procedures. For example, an air suspension procedure includes suspending and tumbling the capsule arrangement in a current of air and a semipermeable wall forming composition until the wall surrounds and coats the capsule. The procedure can be repeated with a different semipermeable wall forming composition to form a semipermeable laminated wall.

Exemplary solvents suitable for manufacturing the semipermeable wall include inert inorganic and organic solvents that do not adversely harm the materials used in the osmotic pump formulations, e.g. the capsule wall, aripiprazole, the thermo-responsive composition, the expandable member, or the final dispenser. Such solvents include aqueous solvents, alcohols, ketones, esters, ethers alipathics hydrocarbons, halogenated solvents, cycloaliphatics, aromatics, heterocyclic solvents, and combinations thereof. Particular solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyloocatane, benzene, toluene, naphtha, 1,4-dioxane, tetrahydrofuran, water, and mixtures thereof such as acetone and water, acetone and methanol, acetone and ethyl alcohol, methylene dichloride and methanol, and ethylene dichloride, methanol, and combinations of the foregoing.

The exit means or hole in the osmotic pump formulations for releasing aripiprazole may be produced during manufacture or in use. For example, the exit means or hole can be formed by mechanical or laser drilling, or by eroding an erodible element in the wall, such as a gelatine plug. The orifice can be a polymer inserted into the semipermeable wall, which polymer is a (micro)porous polymer which typically has at least one (micro)pore.

An example of a formulation for the controlled release of aripiprazole in the stomach and gastrointestinal tract is one in which aripiprazole is dispersed in a polymeric matrix that is water-swellable rather than merely hydrophilic. Such water-swellable matrices typically also have an erosion rate that is substantially slower than their swelling rate, and release aripiprazole primarily by diffusion.

The rate of diffusion of aripiprazole from the matrix can be modified by varying numerous characteristics of the formulation. For example, the rate of diffusion of aripiprazole can be slowed by increasing aripiprazole particle size, by the choice of polymer used in the matrix, and/or by the choice of molecular weight of the polymer. The matrix is typically a relatively high molecular weight polymer that swells upon ingestion, preferably to a size that is at least about twice its unswelled volume, and that might in addition promote gastric retention. Upon swelling, the matrix may convert over a prolonged period of time (such as from about 1 to about 48 hours, e.g. from about 2 to about 24 hours or from about 3 to about 12 hours) from a glassy or crystalline polymer to a polymer this rubbery in consistency.

Typically, penetrating fluid causes release of aripiprazole in a gradual and prolonged manner by the process of solution diffusion, i.e. dissolution of aripiprazole in the penetrating fluid and diffusion of the dissolved drug backed out of the matrix.

Typically, the matrix itself is solid prior to administration, and once administered, remains undissolved in (i.e. is not eroded by) the gastric fluid for a period of time sufficient to permit the majority of aripiprazole to be released in a controlled manner (as defined by the release profiles described above) by solution diffusion. Therefore, the rate-limiting factor in the release of aripiprazole is believed to be controlled diffusion of aripiprazole from the matrix rather than erosion, dissolving or chemical decomposition of the matrix.

The water-swellable polymer which forms the matrix is a polymer that is non-toxic, that swells in a dimensionally unrestricted manner upon absorption of water (and/or other fluids) and that provides for sustained release of incorporated aripiprazole. Examples of suitable polymers include, for example, cellulose polymers and their derivatives (such as hydroxyethylcellulose, hydroxypropylcellulose, carboxymethylcellulose, and microcrystalline cellulose), polysaccharides and their derivatives, polyalkylene oxides, polyethylene glycols, chitosan, poly(vinyl alcohol), polysaccharide gums, maleic anhydride copolymers, poly(vinyl pyrrolidone), starch and starch-based polymers, poly(2-ethyl-2-oxazoline), poly(ethyleneimine), polyurethane hydrogels, crosslinked polyacrylic acids and their derivatives, copolymers of the foregoing polymers, including block copolymers and grafted polymers (e.g. PLURONIC and TECTONIC, which are polyethylene oxide-polypropylene oxide block copolymers) and mixtures thereof.

As used herein, unless otherwise stated, the terms "cellulose" and "cellulosic" denote a linear polymer of anhydroglucose. Suitable cellulosic polymers include, for example, alkyl-substituted cellulosic polymers that ultimately dissolve in the gastrointestinal (GI) tract in a predictably delayed manner. Specific examples are methylcellulose, hydroxymethyl-cellulose, hydroxyethylcellulose, hydroxypropylcellulose, hydroxypropylmethylcellulose, and carboxymethylcellulose. The viscosity of suitable alkyl-substituted cellulosic polymers is typically from about 100 to about 110,000 centipoise as a 2% aqueous solution at 20° C. or from about 1,000 to about 4,000 centipoise as a 1% aqueous solution at 20° C. Exemplary alkyl-substituted celluloses are hydroxyethylcellulose and hydroxypropylmethylcellulose. A specific example of a hydroxyethylcellulose is NATRASOL 250HX NF.

Suitable polyalkylene oxides are those having the properties described above for alkyl-substituted cellulose polymers. An example of a polyalkylene oxide is poly(ethylene oxide) (PEO), which term is used herein to denote a linear polymer of unsubstituted ethylene oxide. Suitable PEO polymers typically have molecular weights of greater than about 4,000,000, preferably from about 4,500,000 to about 10,000,000, more preferably about from 5,000,000 to about 8,000,000. Preferred polyethylene oxides are those with a weight-average molecular weight ranging from about $1 \times 10^5$ to about $1 \times 10^7$, preferably from about $9 \times 10^5$ to about $8 \times 10^6$. Suitable PEOs typically have a viscosity of from about 50 to about 2,000,000 centipoise as a 2% aqueous solution at 20° C. Two specific example of PEOs are POLYOX NF, grade WSR Coagulant, molecular weight 5 million, and grade WSR 303, molecular weight 7 million.

Examples of suitable polysaccharide gums are natural and modified (semi-synthetic) polysaccharide gums such as dextran, xanthan gum, gellan gum, welan gum and rhamsan gum.

Suitable crosslinked polyacrylic acids include those whose properties are the same as or similar to those described above for alkyl-substituted cellulose and polyalkylene oxide polymers. Typically, such crosslinked polyacrylic acids have a viscosity of about 4,000 to about 40,000 centipoise as a 1% aqueous solution at 25° C. Three specific examples are CARBOPOL NF grades 971P, 974P and 934P. Further examples include polymers known as WATER LOCK, which are starch/acrylates/acrylamide copolymers.

As mentioned above, the hydrophilicity and water-swellability of the polymers discussed above cause aripiprazole-containing matrices to swell in size in the gastric cavity due to ingress of water and/or other fluids. This swelling promotes retention of the matrices in the stomach during the fed phase. The hydrophilicity and water-swellability also cause the matrices to become slippery, which provides resistance to peristalsis and further promotes their retention in the stomach.

The release rate of aripiprazole from the matrix is primarily dependent upon the rate of water absorption and the rate at which aripiprazole dissolves and diffuses from the swollen polymer, which in turn is related to the solubility and dissolution rate of aripiprazole, aripiprazole particle size and aripiprazole concentration in the matrix. Also, because these matrix-forming polymers typically dissolve very slowly in gastric fluid, the matrix maintains its physical integrity over at least a substantial period of time, typically for at least 70 or 80% of the dosing period, and in many cases at least 90% and even over 100% of the dosing period. Generally, the particles then slowly dissolve or decompose. Complete dissolution or decomposition may not occur until 24 hours or more after administration, although in many cases, complete dissolution or decomposition will occur within 10 to 24 hours after the dosing period.

The swellable matrix dosage forms may include additives that impart a small degree of hydrophobic character, to further retard the release rate of aripiprazole into the gastric fluid. Examples of such release rate retardants are glyceryl monostearate, fatty acids and salts of fatty acids, (e.g. sodium myristate). Typically, the weight ratio of additive to aripiprazole is in the range of from about 1:10 to about 10:1, for example from about 1:5 to about 5:1.

The amount of polymer relative to aripiprazole may vary, depending on the precise nature of the desired release profile, its molecular weight, and excipients that may be present in the formulation. However, the amount of polymer will be sufficient so that the polymeric matrix will remain substantially intact until all of aripiprazole is released. The term "substantially intact" is used herein to denote a polymeric matrix in which the polymer portion substantially retains its size and shape without deterioration due to becoming solubilized in the gastric fluid or due to breakage into fragments or small particles.

The water-swellable polymers can be used individually or in combination. Certain combinations will often provide a more controlled release of aripiprazole than their components when used individually. Such combinations include cellulose-based polymers (e.g. hydroxyethyl cellulose or hydroxypropyl cellulose) or poly(ethylene oxide) combined with gums, (e.g. xanthan gum).

The benefits of the swellable matrix dosage form are typically achieved over a wide range of aripiprazole loadings, for example weight ratios of aripiprazole to polymer of from about 0.001:1 to about 10:1. Typical loadings (expressed in terms of the weight percent of aripiprazole relative to aripiprazole and polymer combined) are from about 0.001% to about 50%, preferably from about 0.01% to about 40%, such as from about 0.1% to about 30%, for example from about 1% to about 20%.

The swellable matrix formulations also find significant utility when administered to a subject who is in the digestive state (also referred to as the postprandial or "fed" mode). The postprandial mode is distinguishable from the interdigestive (or "fasting") mode by distinct patterns of gastroduodenal motor activity, which determine the gastric retention or gastric transit time of the stomach contents.

Thus, administration of the formulation during the digestive state results in localization of aripiprazole release in the stomach and small intestine reduces and/or prevents substantial colonic degradation, inactivation, or loss of bioavailability.

Juvenile and elderly patients often require dosage forms that are easy to swallow, for example to reduce the risk of choking upon administration, and/or to improve patient compliance. The compositions of the invention may be in the form of easily administerable dosage forms, making them more suitable for patient compliance. Such easily administerable formulations include, for example, sprinkle dosage forms, taste-masked liquid dosage forms, fast-dissolve dosage forms and chewable dosage forms.

It is to be understood that any of the easily administerable dosage forms described below may comprise any of the formulations described above in order to provide a composition which has the desired release profile of aripiprazole according to the subject invention.

An example of a chewable dosage form is a aripiprazole-containing chewable tablet. Such a chewable tablet comprises a chewable base and optionally a sweetener. The chewable base typically comprises an excipient such as mannitol, sorbitol, lactose, or a combination thereof. The optional sweetener used in the chewable dosage form may be, for example, sucrose, liquid glucose, sorbitol, dextrose, isomalt, liquid maltitol, aspartame, lactose, or a combination thereof. In certain cases, the chewable base and the sweetener may be the same component. The chewable base and optional sweetener typically comprise about 50% to about 90% by weight of the total weight of the chewable dosage form.

The chewable dosage form may additionally contain preservatives, agents that retard and/or prevent adhesion to the oral cavity and crystallization of sugars, flavouring agents, souring agents, colouring agents, and combinations of one or more of the foregoing. Glycerin, lecithin, hydrogenated palm oil or glyceryl monostearate may be used as a protecting agent of crystallization of the sugars, typically in an amount of from about 0.01 to about 2% by weight of the total weight of the ingredients. Such protecting agents help to prevent adhesion to oral cavity and improve the soft property or chewability of the dosage form. Additionally or alternatively, isomalt or liquid maltitol may be used to enhance the chewing properties of the chewable dosage form.

The method for making the chewable dosage form comprising aripiprazole described above is similar to the method used to make soft confectionary. Such a method typically involves the formation of a boiled sugar-corn syrup blend to which is added a frappe mixture. The boiled sugar-corn syrup blend may be prepared from sugar and corn syrup blended in parts by weight ratio of 90:10 to 10:90. This blend may be heated to temperatures above 120° C. to remove water and to form a molten mass. The frappe mixture may be prepared from gelatine, egg albumen, milk proteins such as casein, and vegetables proteins such as soy protein, and the like which are added to a gelatine solution and rapidly mixed at ambient temperature to form an aerated sponge like mass. The frappe mixture is then added to the molten candy base and mixed until homogenous, typically at temperatures between 60° C. to about 120° C. A matrix, tablet or other formulation containing aripiprazole may then be added to the mix at a temperature of from about 60° C. to about 90° C., whereupon additional ingredients such as flavours, colourants, and preservatives may be added. The formulation is then typically cooled and formed to pieces of desired dimensions.

Fast-dissolving dosage forms may comprise microparticles and one or more effervescent agents, enabling the dosage forms to rapidly disintegrate in the mouth whilst providing adequate taste-masking. Alternatively, rapidly dissolving dosage forms may contain an active agent and a matrix that includes a nondirect compression filler and a lubricant. U.S. Pat. No. 5,178,878 and U.S. Pat. No. 6,221,392 provide teachings regarding fast-dissolve dosage forms.

Typical fast dissolve dosage forms for use in the subject invention include a mixture incorporating a water and/or saliva activated effervescent agent, a disintegration agent, and microparticles. The microparticles typically incorporate aripiprazole together with a protective material substantially encompassing the aripiprazole. The term "substantially encompassing" includes the meaning that, the protective material substantially shields aripiprazole from contact with the environment outside the microparticle. Thus, each microparticle may incorporate a discrete mass of aripiprazole covered by a coating of the protective material, in which case the microparticle can be referred to as a "microcapsule" or a "microtablet". Alternatively or additionally, each microparticle may have aripiprazole dispersed or dissolved in a matrix of the protective material, optionally coated by a coating composition as described herein.

The mixture including the microparticles and an effervescent agent is typically present as a tablet of a size and shape adapted for direct oral administration to a patient. The tablet is substantially completely disintegrable upon exposure to water and/or saliva. The effervescent disintegration agent is present in an amount effective to aid disintegration of the tablet, and to provide a distinct sensation of effervescence when the tablet is placed in the mouth of a patient.

The effervescent sensation is typically not only pleasant to the patient but also tends to stimulate saliva production, thereby providing additional water to aid in further effervescent action. Thus, once the tablet is placed in the patient's mouth, it will generally disintegrate rapidly and substantially completely without any voluntary action by the patient. Thus, even if the patient does not chew the tablet, disintegration should proceed rapidly. Upon disintegration of the tablet, the microparticles are released and can be swallowed as a slurry or suspension of the microparticles. The microparticles are thus transferred to the patient's stomach for dissolution in the digestive tract and systemic distribution of the aripiprazole.

The terms "effervescent agent" and "disintegration agent" includes compounds which evolve gas. Such agents may evolve gas by means of chemical reactions which take place upon their exposure to water and/or to saliva in the mouth. The bubble or gas generating reaction is most often the result of the reaction of a soluble acid source and an (alkali metal) carbonate source. The reaction of these two general classes of compounds produces carbon dioxide gas upon contact with the water in saliva.

Such saliva/water-activated materials should be kept in a generally anhydrous state with little or no absorbed moisture or in a stable hydrated form since exposure to water will prematurely disintegrate the tablet. For example, the dosage form may be stored in substantially air-tight packaging prior to administration.

The acid source may be any which is safe for human consumption and may generally include food acids, acid anhydrides and acid salts. Food acids include citric acid, tartaric acid, malic acid, fumaric acid, adipic acid, and succinic acids, etc. Because these acids are directly ingested, their overall solubility in water is less important than it would be if the formulations were intended to be dissolved in a glass of water. Acid anhydrides and acid salts of the above-described acids may also be used. Acid salts may include sodium, dihydrogen phosphate, disodium dihydrogen pyrophosphate, acid citrate salts and sodium acid sulfite.

The carbonate source includes dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate, amorphous calcium carbonate, and combinations thereof.

While the effervescent disintegration agent is typically one which upon a reaction which forms carbon dioxide, this is not essential. Effervescent disintegration agents which evolve oxygen or other gasses which are safe for human patients may also be used.

Where the effervescent agent included two mutually reactive components, such as an acid source and a carbonate source, it is preferred that both components react substantially completely. Therefore, an equimolar ratio of acid and carbonate sources is preferred. For example, if the acid used is diprotic, then either twice the molar amount of a mono-reactive carbonate base, or an equal molar amount of a di-reactive base should be used for complete neutralization to be realized. However, the amount of either acid or carbonate source may exceed the amount of the other component. This may be useful to enhance taste and/or performance of a tablet containing an excess of either component. In such cases, it is acceptable that the additional amount of either component may remain unreacted.

The fast-dissolving dosage forms (e.g. tablets) typically contain an amount of effervescent disintegration agent effective to aid rapid and complete disintegration of the tablet when orally administered. By "rapid", it is understood that the tablets should disintegrate in the mouth of a patient in less than 10 minutes, such as from about 15 seconds and about 7 minutes, for example from about 30 seconds and about 5 minutes. Disintegration time in the mouth can be measured by observing the disintegration time of the tablet in water at about 37° C. The tablet is immersed in the water without forcible agitation. The disintegration time is the time from immersion for substantially complete dispersion of the tablet as determined by visual observation. As used herein, the term "complete disintegration" of the tablet does not require dissolution or disintegration of the microcapsules or other discrete inclusions.

In order to achieve such disintegration, the amount of effervescent agent or disintegration agent typically used in the fast-dissolve dosage forms is from about 5% to about 50% by weight of the final composition, preferably from about 15% to about 40% by weight, more preferably about 20% to about 30% by weight.

The tablets described above can be manufactured by well-known tableting procedures.

As mentioned above, each microparticle typically incorporates aripiprazole in conjunction with a protective material. The microparticle may be provided as a microcapsule, microtablet or as a matrix-type microparticle. Microcapsules may incorporate a discrete mass of aripiprazole surrounded by a discrete, separately observable coating of the protective material. Conversely, in a matrix-type particle, aripiprazole is dissolved, suspended or otherwise dispersed throughout the protective material. Certain microparticles may include attributes of both microcapsules and matrix-type particles. For example, a microparticle may incorporate a core incorporating a dispersion of aripiprazole in a first protective material and a coating of a second protective material, which may be the same as or different from the first protective material surrounding the core. Alternatively, a microparticle may incorporate a core consisting essentially of aripiprazole and a coating incorporating the protective material, the coating itself having some aripiprazole dispersed within it. The microparticles typically have a mean diameter of from about 75 to about 600 microns, preferably from about 150 to about 500 microns, for example from about 200 to about 450 microns. The microparticles may be from about 200 to about 30 mesh (US standard size), for example from about 100 to about 35 mesh.

The protective materials suitable for use in the fast dissolve dosage forms described above typically include polymers which are conventionally utilized in the formation of microparticles such as matrix-type microparticles, microtablets and microcapsules. Among these are cellulosic materials such as naturally occurring cellulose, synthetic cellulose derivatives, acrylic polymers and vinyl polymers. Other simple polymers including may also be used, such as proteinaceous materials (e.g. gelatine, polypeptides) and natural and synthetic shellacs and waxes. Protective polymers may also include ethylcellulose, methylcellulose, carboxymethyl cellulose and acrylic resin material.

When a coating is used in the above fast dissolve dosage forms, it typically comprises at least about 5% by weight based on the total weight of the resulting particles, preferably at least about 10% by weight. The upper limit of protective coating material used is generally less critical. In certain embodiments it is possible to use a coating that is greater than 100 percent of weight of the core, providing a relatively thick coating. However, the amount of coating material should not be so great that it impedes the release of a therapeutically effective amount aripiprazole before defecation of the dosage form.

An example of a fast-dissolve dosage form is a hard, compressed, rapidly dissolvable dosage form adapted for direct oral dosing. Such a dosage form typically includes aripiprazole, often in the form of a protected particle, and a matrix. The matrix typically includes a filler and a lubricant, although it may include other additional ingredients. The dosage form is adapted to rapidly dissolve in the mouth of a patient, yet it has a friability of about 2% or less when tested according to the USP. Generally, the dosage form will also have a hardness of at least about 1.5 or 2.0 kP. Not only does the dosage form dissolve quickly, it does so in a way that provides a positive organoleptic sensation to the patient. In particular, the dosage form dissolves with a minimum of unpleasant grit, which is tactilely very inconsistent with organoleptic sensation of the dosage form.

The filler typically comprises a non-direct compression filler. Exemplary fillers include, for example, nondirect compression sugars and sugar alcohols. Such sugars and sugar alcohols include dextrose, mannitol, sorbitol, lactose, and sucrose. Dextrose, for example, can exist as either a direct compression sugar, i.e., a sugar that has been modified to increase its compressibility or a nondirect compression sugar. The percentage of filler is typically in the range of from about 25 to about 98% by weight of the microparticles, preferably from about 50 to about 95%, for example from about 60 to about 90%.

In the fast-dissolve dosage forms discussed above, a relatively high proportion of lubricant is typically used. Lubricants, and in particular, hydrophobic lubricants such as magnesium stearate, may be used in an amount of from about 0.25 to about 5% by weight of the formulation, preferably from about 1 to about 3% by weight, for example from about 1.5 to about 2% by weight. Despite the use of this relatively high percentage weight of lubricant, the formulations typically exhibit excellent compressibility, hardness, and rapid dissolution within the mouth.

Hydrophobic lubricants include, for example, alkaline earth metal stearates, stearic acid, mineral and vegetable oils, glyceryl behenate, sodium stearyl fumarate, and combinations thereof. Hydrophilic lubricants may be also be used.

The hard, compressed fast-dissolve dosage forms typically have a hardness of at least about 1.5 kP and are designed to dissolve spontaneously and rapidly in the mouth of a patient in less than about 90 seconds to thereby liberate the particles. Preferably the dosage form will dissolve in less than about 60 seconds and even more preferably in about 30 to about 45 seconds. This measure of hardness is based on the use of small tablets of less than about 0.25 inches in diameter. A hardness of at least about 2.0 kP is preferred for larger tablets. Direct compression techniques are preferred for the formation of these tablets.

Sprinkle dosage forms are another form of easily administered formulations that may be used in the compositions of the invention. Sprinkle dosage forms typically comprise aripiprazole in the form of pellets, granules, microtablets or microcapsules, optionally having functional or non-functional coatings. In use, the patient or caregiver can sprinkle the particulate/pelletized dose into drink or onto soft food. A sprinkle dosage form may comprise particles having a mean diameter of from about 10 to about 100 μm in their major dimension, for example from about 50 to 70 μm.

An example of a sprinkle dosage form is an easily openable capsule enclosing a plurality of aripiprazole-containing micropellets. Each of the micropellets typically comprises a seed coated with a first coating mixture of aripiprazole and polyvinylpyrrolidone and a second coating mixture of from about 90 to about 70% by weight of the mixture of a non-hydrophilic polymer (e.g. ethyl cellulose) and from about 10 to about 30% by weight of the mixture of a hydrophilic polymer (e.g. hydroxypropyl methyl cellulose). For example, the second coating mixture may comprise about 3 parts ethylcellulose to about 1 part hydroxypropylcellulose. The weight of the second coating mixture is about 5-10% of the weight of the micropellets before the second coating is applied. Optionally, the second coating contains aripiprazole.

The polyvinylpyrrolidone used in the first coating typically has a molecular weight of from about 30,000 to about 50,000, e.g. about 40,000. The seed of the sprinkle dosage form may be a sugar seed and have a mesh size of 60/80.

Taste-masked dosage forms are another form of easily administered formulations that may be used in the compositions of the invention. The taste-masked dosage form may be liquid or solid.

A solid taste masked dosage form typically comprises a core element comprising aripiprazole and a coating material surrounding the core element. The core element comprising aripiprazole is typically in the form of a (micro)particle, (micro)tablet, (micro)capsule, amorphous solid, pellet, granule, powder or a matrix. The core element may include carriers or excipients, fillers, flavouring agents, stabilizing agents and/or colourants in addition to aripiprazole.

The taste-masked dosage form typically includes from about 50 to about 99% by weight, preferably from about 65 to about 95% by weight, for example from about 80 to about 90% by weight of the aripiprazole-containing core element, based on the total weight of the dosage form. The taste-masked dosage form typically includes from about 1 to about 50% by weight, preferably from about 5 to about 35% by weight, for example from about 10 to about 20% by weight of the coating material surrounding the core element, based on the total weight of the dosage form.

The core element typically includes from about 20 to about 90% by weight of a supplementary component selected from waxes, water insoluble polymers, enteric polymers, and partially water soluble polymers, other suitable pharmaceutical excipients, and combinations thereof.

The core element optionally includes carriers or excipients, fillers, flavouring agents, stabilizing agents, colorants, and combinations thereof. Suitable fillers include, for example, insoluble materials such as silicon dioxide, titanium dioxide, talc, alumina, starch, kaolin, polacrilin potassium, powdered cellulose, and microcrystalline cellulose, and combinations comprising one or more of the foregoing fillers. Soluble fillers include, for example, mannitol, sucrose, lactose, dextrose, sodium chloride, sorbitol, and combinations comprising one ore more of the foregoing fillers. The filler may be present in amounts of up to about 75% by weight based on the total weight of the dosage form.

The core element may be in the form of a powder, for example, having a particle size range of about 35 μm to about 125 μm. Such small particle size facilitates a substantially non-gritty feel in the mouth. Small particle size also minimizes break-up of the particles in the mouth, e.g. by the teeth. When in form of a powder, the taste masked dosage form may be administered directly into the mouth or mixed with a carrier such as water, or semi-liquid compositions such as syrups, yogurt, and the like. However, the taste-masked aripiprazole may be provided in any suitable unit dosage form.

The coating material of the taste-masked formulation may take a form that provides a substantially continuous coating and provides taste masking. The coating may also provide controlled release of aripiprazole. The polymer used in taste masked dosage form coating may be a water insoluble polymer such as, for example, ethyl cellulose. The coating material of the taste masked dosage form may further include a plasticizer.

A method of preparing taste-masked pharmaceutical formulations such as powdered formulations typically includes mixing a core element and a coating material in a diluent and spray drying the mixture to form a taste-masked formulation. Spray drying of the pharmaceutically active ingredient and polymer in the solvent typically involves spraying a stream of air into an atomized suspension, optionally in a drying chamber, so that solvent is caused to evaporate leaving aripiprazole coated with the polymer coating material.

For a solvent such as methylene chloride, the solvent concentration in the drying chamber is typically maintained at from about 40,000 to about 100,000 parts per million of organic solvent. The spray-drying process for such solvents may be conducted at a process temperature of about 5° C. to about 35° C. Spray drying of the dosage forms may be undertaken utilizing either rotary, pneumatic or pressure atomizers located in either a co-current or mixed-flow spray dryer or variations thereof. The drying gas may be heated or cooled to control the rate of drying. A temperature below the boiling point of the solvent may be used. Inlet temperatures may be from about 40 to about 120° C. and outlet temperatures from about 5° C. and 35° C.

The coat formation may be optimized to meet the needs of the material or application. Controlling the process parameters such as temperature, solvent concentration, spray dryer capacity, atomizing air pressure, droplet size, viscosity, total air pressure in the system and the solvent system, allows the formation of a range of coats, ranging from dense, continuous, non-porous coats through to more porous microcapsule/polymer matrices.

A post-treatment step may be used to remove any residual solvent. The post treatment may include a post drying step including drying the final product on a tray and/or at a bed temperature sufficient to remove excess solvent, but not degrade the aripiprazole. Preferably the drying temperature is in the range of from about 35° C. to about 40° C. Once completed, the product may be collected by a suitable method, such as collection by sock filters or cyclone collection.

An exemplary chewable taste-masked dosage form comprises a microcapsule of about 10 μm to about 1.5 mm in diameter having a core comprising aripiprazole and a polymer mixture coating having sufficient elasticity to withstand chewing. The polymeric mixture coating typically comprises from about 30 to about 70% by weight of a polymer that forms a polymeric film at temperatures of at least about 30° C. (e.g. ethylcellulose) and from about 30 to about 70% by weight of a copolymer that forms a polymeric film at temperatures less than about 25° C. The polymeric mixture coating is adapted so that the dosage form exhibits the release profiles discussed earlier in this specification.

The copolymer that forms a polymeric film at temperatures less than about 25° C. is typically a methacrylic acid ester copolymer (having, for example, a weight average molecular weight of about 800,000) or a styrene acrylate copolymer.

The core of the taste-masked aripiprazole dosage form described above may comprise a diluent and/or a plasticizer. Suitable plasticizers, include, but are not limited to polyethylene glycol, triacetin, vinylpyrrolidone, diethyl phthalate, dibutylsebacate, a citric acid ester, and combinations thereof.

Solid taste-masked dosage forms (e.g. polymer coated aripiprazole powder) may be reconstituted as suspensions in a liquid vehicle such as water before usage. This has the advantage that the reconstitutable solid taste-masked dosage forms typically have a longer shelf life than many liquid taste-masked dosage forms and the suspensions, once reconstituted, have adequate taste masking.

Aripiprazole is considered to impart its clinical activity via its partial agonist properties on post-synaptic dopamine receptors in several dopamine pathways in the brain. It is currently used for the treatment of both positive and negative symptoms of all forms of schizophrenia and has an indication for use as a short treatment of acute mania, or manic symptoms associated with bipolar disorders. The subject invention seeks to address the deficiencies of known aripiprazole-containing formulations for the treatment of schizophrenia and bipolar disorders by providing the orally deliverable pharmaceutical compositions described herein. However, these compositions may be used in the treatment of numerous other medical indications in addition to schizophrenia and bipolar disorders, as described in more detail below.

Partial agonism is an unusual mechanism of action, but not unique to aripiprazole regarding neuromodulation of neurotransmitter activity in the brain. Aripiprazole competes for and binds to post synaptic receptors, mainly on the dopamine pathways in the mammalian brain. The resultant effect of partial agonism is a 'dampening down' of the extremes of activation of neuronal pathways—in a pathway where the neurones are not being stimulated enough, the partial agonist acts as an agonist ('stimulant'); in a pathway where there is over-activation, the partial agonist acts as an antagonist ('inhibitory agent'). Aripiprazole acts mainly on the dopamine pathways in the brain, in particular those involved in reward mechanisms. It works on both the positive and negative symptoms of schizophrenia due to its balancing effect, and to date has also achieved an indication for the control of acute mania as part of bipolar I disorder. Anecdotal evidence exists of its utility in treating the depressive symptoms of both schizophrenia and bipolar I disorder, this is predictable by its mode of action. Clinical trials are ongoing and are expected to result in farther indications for long term use as a mood stabilizer in bipolar disorders and as an antidepressant product.

The subject invention provides the use of an orally deliverable pharmaceutical composition as defined in the claims for the treatment of a neurological and/or a psychiatric condition.

By the term "a neurological and/or a psychiatric condition", we include all conditions deriving from a pathology of the nervous system. Particular examples of such conditions are described in more detail below.

The phrase "the treatment of a neurological and/or a psychiatric condition" is intended to include use for the acute, chronic and/or prophylactic treatment of neurological, neuropsychiatric, psychiatric and neurodegenerative disease.

Accordingly, there are numerous conditions which may be treated by administering or using the compositions of the invention. The invention is particularly suited to all conditions involving two extremes of activation of the dopamine pathways in the brain. These include all bipolar disorders, schizoaffective disorders, Generalized Anxiety disorder, obsessive compulsive disorder, Post Traumatic Stress Disorder, Personality Disorder and Borderline Personality Disorder, all types of cognitive impairment (e.g. mild cognitive impairment of the elderly); psychiatric complications of stroke (including haemorrhagic and ischaemic and sequelae), epilepsy, transient ischaemic attacks, traumatic brain injury, Parkinsons disease, Huntingtons disease, amytrophic lateral sclerosis; neuropathic pain, idiopathic pain, all psychoses (such as degenerative schizophrenia and catatonia), all addictions, (e.g. addiction to alcohol, nicotine and opiates), all eating disorders including bulimia and anorexia, affective disorders including ADHD (attention deficit hyperactivity disorder), all depressive disorders, personality disorders (including borderline personality disorders), sleep disorders (including jet lag and insomnia), Downs syndrome, meningitis, central nervous system vasculitis, leukodystrophies and adrenoleukodystrophies (including Alexander's disease, Canavan's disease, cerebrotendinous xanthomatosis, Krabbes and metachromatic LD), fatigue, hypoglycaemia, encephalopathy, (such as hepatic and septic encephalopathy), tumours of the brain and spinal cord (including primary tumours of glial, neuronal, schwann cell, pinealcyte, meningioma, melanoma, sarcoma, lymphoma and multiple systemic systemic malignancies which metasize), cerebellar degeneration and ataxias (e.g. Friedrich's ataxia, cerebellar cortical atazia, complicated cerebellar ataxia, which includes olivopontocerebellar degeneration, spinocerebellar disease, dentatorubral degeneration and autosomal dominant ataxias) vertigo, vestibular system damage, cochlear disorders such as tinnitus, nystagmus, peripheral neuropathy, (e.g. polyneuropathy, polyradiculopathy, motor neuronopathy, sensor neuronopathy, multiple mononeuropathy and plexopathies), metabolic bone diseases, osteoporosis, pulmonary disorders, (such as pulmonary edema, neurogenic pulmonary edema, bronchial asthma, adult respiratory distress syndrome (ARDS) and pulmonary cell death by apoptosis or necrosis), obesity and complications thereof, diabetes and prediabetes, and combinations thereof.

The compositions of the invention may comprise one or more active agents in addition to aripiprazole.

For example, the compositions of the invention may comprise another atypical antipsychotic agent (e.g. olanzapine, quetiapine, risperidone, amisulpride, clozepine, chlorpromazine, or haloperidol decanoate), antiparlinsonian agents (e.g. L-DOPA, Dopamine Agonists), sedatives (e.g. a benzodiazepine sedative or non-barbituate sedative), anxiolytics (e.g. benzodiazepines such as lorazepam, chlordiazepoxide, oxazepam, clorazepate, diazepam, and alprazolam), antidepressants, and mood stabilizers (e.g. lamotrigine, lithium, valproate, carbamazepine, oxcarbazepine).

The antiparkinsonian agents may be used to treat the tardive dyskinesia associated with neuroleptic use. Also called "side-effect medication" antiparkinsonians are indicated when muscle side-effects of the atypical antipsychotics make patients uncomfortable. Antiparkinsonian agents are typically anticholinergic drugs, examples including benztropine mesylate, trihexyphenidyl, procyclidine, and amantadine.

Suitable antidepressents include tricyclic antidepressants (such as amitriptyline, imipramine, doxepin, and clomipramine), monoamine oxidase A or B inhibitors (such as phenelzine andtranylcypromine), tetracyclic antidepressants (e.g. maprotiline), and serotonin re-uptake inhibitors such as fluoxetine, cipramil, S-cipramil, paroxetine, and sertraline hydrochloride, serotonin and nor adrenaline reuptake inhibitors such as venlafaxine and duloxetine, nor adrenaline reuptake inhibitors such as reboxetine and viloxazine and all other classes of antidepressants.

Compositions of the invention including one or more of the compounds listed above in addition to aripiprazole are particularly suitable for the treatment of certain patients suffering from schizophrenia, such as those suffering from severe or unresponsive symptoms of schizophrenia.

Of course, the aripiprazole formulations described herein may be used for the treatment of numerous other conditions in addition to Schizophrenia. Such conditions may require treatment by different additional active agents (in addition to aripiprazole) than those described above in relation to the treatment of Schizophrenia.

The invention will now be illustrated by the following non-limiting Examples.

EXAMPLE 1

Aripiprazole Compositions 30 mg direct compression (DC) and wet granulation (WG) controlled release tablets were manufactured as described below.

Direct Compression Tablets

The ingredients set out in Table 1 below were blended together in a planetary mixer for 5 minutes. The blend was compressed on a rotary tabletting machine, using 7.0 mm diameter round n/c punches. The tablet breaking strength was 2.5 kp to 3.5 kp.

TABLE 1

| Direct Compression Composition DJ/1/27/A DC | | | |
|---|---|---|---|
| Ingredient | % | tablet mg | batch g |
| Aripiprazole | 20 | 30 | 100 |
| Methocel K4M | 35 | 52.5 | 175 |
| Avicel PH 200 | 44 | 66 | 220 |
| Sodium Stearyl Fumarate | 1 | 1.5 | 5 |
|  | 100 | 150 | 500 |

Wet Granulation Tablets

The ingredients set out in Table 2 below except for sodium stearyl fumarate were blended together in planetary mixer for 5 minutes prior to wet granulation with purified water. The moist powders were dried in a fluid bed drier at an inlet temperature of 70° C. for 15 minutes. The dried granule had a loss on drying value of 2.5% w/w. The granules were sieved through an 850 μm screen and blended for 1 minute with the Sodium Stearyl Fumarate. The blend was compressed at 150 mg on a rotary tabletting machine, using 7.0 mm diameter round n/c punches. The tablet breaking strength was 5.0 kp to 6.0 kp.

TABLE 2

| Wet Granulation Composition DJ/1/27/C WG | | | |
|---|---|---|---|
| Ingredient | % | tablet mg | batch g |
| Aripiprazole | 20 | 30 | 100 |
| Methocel K4M | 35 | 52.5 | 175 |
| Avicel PH 200 | 39 | 58.5 | 195 |
| PVPK30 | 5 | 7.5 | 25 |
| Sodium Stearyl Fumarate | 1 | 1.5 | 5 |
|  | 100 | 150 | 500 |

In the above tablets, the aripiprazole was obtained from LGM Pharmaceuticals (US). The methocel K4M ((hydroxypropyl methylcellulose 2208 (hypromellose)) was obtained from Colorcon Limit (UK). Avicel PH 200 (microcrystalline cellulose) was obtained from FMC BioPolymer (Ireland). PVPK30 (polyvinylpyrrolidine) was obtained from Shanghai WellTone Material Co., Ltd, China. Sodium Stearyl Fumarate, under the trade mark PRUV, was obtained from JRS Pharma GMBH (Germany).

EXAMPLE 2

In Vitro Release Experiments

The release profiles of Aripiprazole from the DC and WG tablets described in Example 1 were studied in pH 4.0 phosphate buffer and 0.1M HCl, as described in more detail below.

Dissolution System

| | |
|---|---|
| Dissolution medium | 0.05M Phosphate Buffer (pH 4.0) or 0.1M Hydrochloric Acid |
| Apparatus | USP II (Paddles) |
| Volume | 900 ml |
| Speed | 100 rpm |
| Temperature | 37° C. |

7 liters 0.05M Phosphate buffer (pH 4.0) was prepared by dissolving 47.8 g potassium phosphate in 6.75 liters of water, then adding portions of 60% orthophosphoric acid solution to obtain a pH of 4.0 (±0.05). The solution was made up to 7 liters with water and the pH adjusted as necessary with sodium hydroxide or phosphoric acid).

The 0.1M HCl was prepared by diluting 3.5 liters of 0.2M hydrochloric acid to 7 liters with purified water.

Dissolution Procedure

Aliquots were taken from each dissolution vessel at the indicated (e.g hourly) hourly intervals. The UV absorbance of each aliquot at 215 nm was measured against a blank solution of 0.05M phosphate buffer and calibrated against three reference standards (0.03, 0.0012 and 0.0006 mg/ml aripiprazole). The % aripiprazole dissolved is calculated using the calibration curve created from the reference standards:

p=purity of reference standard as % w/w (not required when the input batch of drug substance is used as the reference standard)

X=value obtained from graph in mg/ml $$\% \text{ dissolved} = \frac{X \times 900 \times p \times 100\%}{\text{Label claim (mg)} \times 100}$$

Table 3 below shows the averaged hourly Aripiprazole release percentages over 23 hours from the DC tablet of Example 1 in pH 4.0 phosphate buffer. The corresponding graph of Aripiprazole release over time is shown in FIG. 1.

TABLE 3

% Aripiprazole (DC) release in pH 4.0 phosphate buffer over 23 hours

| | Time/h | | | | | | | | | | |
|---|---|---|---|---|---|---|---|---|---|---|---|
| | 0 | 1 | 2 | 3 | 4 | 5 | 6 | 7 | 8 | 9 | 10 |
| % Release | 0.0 | 10.4 | 14.6 | 20.6 | 26.3 | 32.4 | 38.3 | 43.7 | 48.1 | 52.9 | 56.5 |

| | Time/h | | | | | | | | | | |
|---|---|---|---|---|---|---|---|---|---|---|---|
| | 13 | 14 | 15 | 16 | 17 | 18 | 19 | 20 | 21 | 22 | 23 |
| % Release | 69.7 | 75.5 | 78.9 | 82.2 | 84.1 | 85.8 | 87.8 | 89.2 | 91.1 | 91.7 | 92.7 |

Table 4 below shows the averaged hourly Aripiprazole release percentages over 20 hours from the direct compression tablet of Example 1 in 0.1M HCl. The corresponding graph of Aripiprazole release over time is shown in FIG. 2.

The published model (Mallikaarjun et al, see above) was used to simulate plasma concentrations of aripiprazole after various dose regimens of the IR formulation. In addition, various dose regimens of a sustained-release (SR) formula-

TABLE 4

Aripiprazole (DC) release in 0.1M HCl over 20 hours

| | Time/h | | | | | | | | | | | | | | | | | | |
|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 16 | 17 | 19 | 20 |
| % Release | 0.0 | 6.5 | 10.7 | 15.8 | 21.5 | 27.4 | 33.9 | 40.4 | 46.7 | 54.0 | 60.7 | 67.6 | 71.5 | 80.4 | 81.4 | 89.5 | 90.1 | 91.1 | 95.8 |

Table 5 below shows the averaged hourly Aripiprazole release percentages over 23 hours from the WG tablet of Example 1 in 0.1M HCl. The corresponding graph of Aripiprazole release over time is shown in FIG. 3.

tion were simulated assuming that the release was zero-order for examples ranging from 10 h to 18 h. The simulated plasma profiles of aripiprazole from the new SR formulations were compared to modelling of the currently utilized IR regimen.

TABLE 5

Aripiprazole (WG) release in 0.1M HCl over 23 hours

| | Time/h | | | | | | | | | | |
|---|---|---|---|---|---|---|---|---|---|---|---|
| | 0 | 1 | 2 | 3 | 4 | 5 | 6 | 7 | 8 | 9 | 10 |
| % Release | 0.0 | 6.7 | 12.5 | 17.1 | 24.3 | 32.0 | 40.0 | 45.9 | 52.9 | 60.7 | 65.1 |

| | Time/h | | | | | | | | | | |
|---|---|---|---|---|---|---|---|---|---|---|---|
| | 13 | 14 | 15 | 16 | 17 | 18 | 19 | 20 | 21 | 22 | 23 |
| % Release | 79.5 | 86.4 | 89.4 | 91.7 | 94.4 | 95.4 | 96.2 | 97.1 | 96.0 | 99.1 | 96.1 |

Table 6 below shows the averaged hourly Aripiprazole release percentages over 15 hours from the WG tablet of Example 1 in pH 4.0 phosphate buffer. The corresponding graph of Aripiprazole release over time is shown in FIG. 4.

Plasma aripiprazole plasma concentration profiles after repeated dosing were simulated, using the prescribed model, by means of WinNonLin Pro Version 5.2 (Pharsight Corporation Inc., Mountain View, Calif., USA, 2006). 15 mg arip-

TABLE 6

% Aripiprazole (WG) release in pH 4.0 phosphate buffer over 15 hours

| | Time/h | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| % Release | 0.0 | 14.4 | 20.4 | 25.1 | 29.7 | 34.0 | 37.5 | 40.9 | 45.2 | 47.5 | 51.0 | 53.6 | 56.6 | 58.8 | 61.1 | 62.9 |

EXAMPLE 3

Pharmacokinetic Modelling

Multiexponential functions were fitted to the published plasma concentration-time profiles of immediate-release (IR) aripiprazole after repeated once-daily oral doses of 5, 10, 15 and 20 mg (Mallikaarjun S, Salazar D, Braner S, "Pharmacokinetics, tolerability and safety of aripiprazole following multiple oral dosing in normal healthy volunteers", *J. Clin. Pharmacol.*, 2004; 44:179-187).

The function (representing first-order absorption with two-compartment disposition) was of the form:

$$C(t) = A \cdot e^{-\alpha(t)} + B \cdot e^{-\beta(t)} + C \cdot e^{-01(t)}$$

where A, B, $\alpha$, $\beta$ and $k_{01}$ are constants, $C = -(A+B)$ and $C(t)$ is the plasma concentration at time, t.

iprazole was the most commonly used dose (Molden E, Lunde H, Lunder N, Refsum H, "Pharmacokinetic variability of aripiprazole and the active metabolite dehydroaripiprazole in psychiatric patients", *Ther. Drug Monit.*, 2006; 28:744-749). Therefore, the multiexponential function fitted to the 15 mg IR data was selected as the comparative IR dose. Linear kinetics were assumed for this analysis, consistent with the dose-proportional kinetics observed (Mallikaarjun et al). The SR formulation was represented by the multi-exponential function fitted to the 5 mg IR data and assuming zero-order input (absorption) for 10 or 14 h.

The prescribed mean functions fitted to the plasma concentrations of aripiprazole following once-daily oral dosing of 5, 10, 15 and 20 mg of the IR formulation (Mallikaarjun et al) are presented in Table 7.

TABLE 7

Mean parameters of the multi-exponential model fitted to the plasma concentration profiles of aripiprazole following administration of an IR formulation

| Parameter | Dose (mg) | | | |
|---|---|---|---|---|
| | 5 | 10 | 15 | 20 |
| Parameters published for IR formulation | | | | |
| A (ng/mL) | 79.3 | 117 | 183 | 191 |
| B (ng/mL) | 15.8 | 35.5 | 48.6 | 63.1 |
| $t_{1/2}$ (ABS) (h) | 1.50 | 1.20 | 1.20 | 1.60 |
| $t_{1/2}$ ($\alpha$) (h) | 2.60 | 2.10 | 4.50 | 2.40 |
| $t_{1/2}$ ($\beta$) (h) | 71.1 | 58.0 | 58.7 | 78.6 |
| Parameters used for IR formulation | | | | |
| A (ng/mL) | 79.3 | 117 | 183 | 191 |
| B (ng/mL) | 15.8 | 35.5 | 48.6 | 63.1 |
| $k_{01}$ (/h) | 0.462 | 0.578 | 0.578 | 0.433 |
| $\alpha$ (/h) | 0.267 | 0.330 | 0.154 | 0.289 |
| $\beta$ (/h) | 0.00975 | 0.0120 | 0.0118 | 0.00882 |

| Parameter | Value |
|---|---|
| Parameters published for IR formulation (5 mg) | |
| V (L) | 116 |
| $k_{21}$ (/h) | 0.104 |
| $t_{1/2}$ ($\alpha$) (h) | 2.60 |
| $t_{1/2}$ ($\beta$) (h) | 71.1 |
| Parameters used for SR formulation (5 mg) | |
| V (mL) | 0.116 |
| $k_{21}$ (/h) | 0.104 |
| $\alpha$ (/h) | 0.267 |
| $\beta$ (/h) | 0.00975 |
| Input duration (h) | 10 or 14 |

The simulated concentrations of aripiprazole are illustrated in FIG. 5. The simulated profiles are similar to those published (Mallikaarjun et al).

Steady-state simulations of aripiprazole following 30 mg IR administered every other day are compared to simulations after once-daily dosing of 15 mg IR in FIG. 6.

Steady-state simulations of aripiprazole following 15 mg IR administered every other day are compared to simulations after once-daily dosing of 15 mg IR in FIG. 7.

Steady-state simulations of aripiprazole following 30 mg 14-h SR form administered every other day are compared to simulations after once-daily dosing of 15 mg IR in FIG. 8.

Steady-state simulations of aripiprazole following 60 mg 14-h SR form administered weekly are compared to simulations after once-daily dosing of 15 mg IR in FIG. 9.

Steady-state simulations of aripiprazole following 30 mg 14-h SR form administered twice-weekly (e.g. every Wednesday and Sunday) are compared to simulations after once-daily dosing of 15 mg IR in FIG. 10.

Steady-state simulations of aripiprazole following 45 mg 14-h SR form administered twice-weekly (e.g. every Wednesday and Sunday) are compared to simulations after once-daily dosing of 15 mg IR in FIG. 11.

Steady-state simulations of aripiprazole following 60 mg. 14-h SR form administered twice-weekly (e.g. every Wednesday and Sunday) are compared to simulations after once-daily dosing of 15 mg IR in FIG. 12.

Steady-state simulations of aripiprazole following 30 mg 10-h SR form administered every other day are compared to simulations after once-daily dosing of 15 mg IR in FIG. 13.

Steady-state simulations of aripiprazole following 30 mg 18-h SR form administered every other day are compared to simulations after once-daily dosing of 15 mg IR in FIG. 14.

Steady-state simulations of aripiprazole following 60 mg 10-h SR form administered weekly are compared to simulations after once-daily dosing of 15 mg IR in FIG. 15.

Steady-state simulations of aripiprazole following 60 mg 18-h SR form administered weekly are compared to simulations after once-daily dosing of 15 mg IR in FIG. 16.

Steady-state simulations of aripiprazole following 45 mg 10-h SR form administered twice-weekly (e.g. every Wednesday and Sunday) are compared to simulations after once-daily dosing of 15 mg IR in FIG. 17.

Steady-state simulations of aripiprazole following 45 mg 18-h SR form administered twice-weekly (e.g. every Wednesday and Sunday) are compared to simulations after once-daily dosing of 15 mg IR in FIG. 18.

Steady-state simulations of aripiprazole following 15 mg 14-h SR administered once daily are compared to simulations after once-daily dosing of 15 mg IR in FIG. 19.

Steady-state simulations of aripiprazole following 15 mg 10-h SR administered once daily are compared to simulations after once-daily dosing of 15 mg IR in FIG. 20.

The results in FIG. 6 suggest that the 30 mg IR dosed every two days would have a significantly greater chance of adverse events (due to the high Cmax) compared to the OD 15 mg IR regimen. On the other hand, FIG. 7 shows that the aripiprazole plasma concentrations of the 15 mg IR every other day regimen are lower than the OD 15 mg IR regimen.

The results shown in FIGS. 8, 13 and 14 show that the 30 mg SR formulation dosed every two days has very similar peak to trough properties compared to 15 mg IR dosed daily. This suggests the potential for comparable efficacy but with an improved dosing schedule.

The 45 mg SR formulation dosed twice weekly (see FIGS. 11, 17 and 18) has similar peak to trough properties compared to 15 mg IR dosed daily, which given the current lack of understanding in the relationship between plasma exposure and drug effects (Drugs at FDA; Abilify (NDA#021436 Tablet Oral)) suggests the potential for comparable efficacy but with an improved dosing schedule. Similarly, the aripiprazole plasma concentration profile for the 60 mg SR formulation dosed weekly (see FIGS. 9, 15 and 16) is believed to fall within tolerated and efficacious levels.

The results in FIGS. 19 and 20 also suggest that the once daily 15 mg SR formulation would have a significantly decreased chance of adverse events (due to the low Cmax) compared to the analogous 15 mg IR regimen.

The invention claimed is:

1. A method of treating a patient with one or more of a neurological and a psychiatric condition selected from the group consisting of schizophrenia, bipolar disorder, schizoaffective disorders, and combinations thereof, the method comprising orally administering to the patient once weekly a pharmaceutical composition for the controlled release of aripiprazole, the pharmaceutical composition comprising a therapeutically effective amount of aripiprazole and at least one release-retarding material comprising a water-swellable polymer that forms a matrix that retards the release of the aripiprazole such that the aripiprazole released from the composition is effective in treating the neurological or psychiatric condition for a period of one week.

2. The method of claim 1, wherein the treatment is associated with the partial agonist properties of aripiprazole on neurotransmitter pathways in the brain.

3. The method of claim 1, wherein one or more of the neurological and a psychiatric condition is associated with Dopamine receptors.

4. The method of claim 1, wherein the water-swellable polymer comprises a cellulose polymer.

5. The method of claim 4, wherein the cellulose polymer comprises an alkyl-substituted cellulosic polymer.

6. The method of claim 5, wherein the alkyl-substituted cellulosic polymer is methylcellulose, hydroxymethylcellulose, hydroxyethylcellulose, hydroxypropylcellulose, hydroxypropylmethylcellulose or carboxymethylcellulose.

7. The method of claim 6, wherein the alkyl-substituted cellulosic polymer is hydroxypropylmethylcellulose.

8. The method of claim 1, wherein the composition further comprises a filler.

9. The method of claim 8, wherein the filler is silicon dioxide, titanium dioxide, talc, alumina, starch, kaolin, polacrilin potassium, powdered cellulose, or microcrystalline cellulose, or any combinations thereof.

10. The method of claim 9, wherein the filler comprises microcrystalline cellulose.

11. The method of claim 1, wherein the composition further comprises a lubricant.

12. The method of claim 11, wherein the lubricant is calcium stearate, glycerol behenate, magnesium stearate, mineral oil, polyethylene glycol, sodium stearylfumarate, stearic acid, talc, vegetable oil, or zinc stearate, or any combinations thereof.

13. The method of claim 12, wherein the lubricant comprises sodium stearylfumarate.

* * * * *